United States Patent
Ito et al.

(10) Patent No.: US 10,688,031 B2
(45) Date of Patent: Jun. 23, 2020

(54) LOW-TOXICITY SOPHOROLIPID-CONTAINING COMPOSITION AND USE THEREFOR

(71) Applicant: Saraya Co., Ltd., Osaka-Shi, Osaka (JP)

(72) Inventors: Hitoshi Ito, Kashiwara (JP); Michiaki Araki, Kashiwara (JP); Yoshihiko Hirata, Kashiwara (JP)

(73) Assignee: Saraya Co., Ltd., Osaka-Shi (JP)

( * ) Notice: Subject to any disclaimer, the term of this patent is extended or adjusted under 35 U.S.C. 154(b) by 0 days.

(21) Appl. No.: 15/061,330

(22) Filed: Mar. 4, 2016

(65) Prior Publication Data

US 2016/0324747 A1    Nov. 10, 2016

Related U.S. Application Data

(63) Continuation-in-part of application No. PCT/JP2014/073356, filed on Sep. 4, 2014.

(30) Foreign Application Priority Data

Sep. 4, 2013  (JP) .................................. 2013-183463

(51) Int. Cl.

| | |
|---|---|
| *A61K 8/60* | (2006.01) |
| *A61K 9/00* | (2006.01) |
| *A61K 8/36* | (2006.01) |
| *A61K 8/365* | (2006.01) |
| *A61K 8/99* | (2017.01) |
| *A61K 8/34* | (2006.01) |
| *A61K 47/12* | (2006.01) |
| *A61K 47/26* | (2006.01) |
| *A61L 15/20* | (2006.01) |
| *A61L 15/42* | (2006.01) |
| *A61Q 5/00* | (2006.01) |
| *A61Q 5/02* | (2006.01) |
| *A61Q 11/00* | (2006.01) |
| *A61Q 19/00* | (2006.01) |
| *A61Q 19/02* | (2006.01) |
| *A61Q 19/10* | (2006.01) |
| *A61K 31/27* | (2006.01) |
| *A61K 31/4174* | (2006.01) |
| *A61K 31/4415* | (2006.01) |
| *A61K 31/7028* | (2006.01) |

(52) U.S. Cl.

CPC .............. *A61K 8/602* (2013.01); *A61K 8/342* (2013.01); *A61K 8/361* (2013.01); *A61K 8/365* (2013.01); *A61K 8/60* (2013.01); *A61K 8/99* (2013.01); *A61K 9/0048* (2013.01); *A61K 31/27* (2013.01); *A61K 31/4174* (2013.01); *A61K 31/4415* (2013.01); *A61K 31/7028* (2013.01); *A61K 47/12* (2013.01); *A61K 47/26* (2013.01); *A61L 15/20* (2013.01); *A61L 15/42* (2013.01); *A61Q 5/002* (2013.01); *A61Q 5/02* (2013.01); *A61Q 11/00* (2013.01); *A61Q 19/00* (2013.01); *A61Q 19/007* (2013.01); *A61Q 19/02* (2013.01); *A61Q 19/10* (2013.01); *A61K 2800/42* (2013.01); *A61K 2800/592* (2013.01); *A61K 2800/74* (2013.01)

(58) Field of Classification Search

CPC ................ A61K 2300/00; A61K 31/27; A61K 31/4174; A61K 31/4415; A61K 31/7028; A61K 2800/42; A61K 2800/592; A61K 2800/74; A61K 47/12; A61K 47/26; A61K 8/342; A61K 8/361; A61K 8/365; A61K 8/60; A61K 8/602; A61K 8/99; A61K 9/0048; A61L 15/20; A61L 15/42; A61Q 5/02; A61Q 19/007; A61Q 19/02; A61Q 5/002; A61Q 11/00; A61Q 19/00; A61Q 19/10

See application file for complete search history.

(56) References Cited

U.S. PATENT DOCUMENTS

| | | |
|---|---|---|
| 5,756,471 A | 5/1998 | Hillion et al. |
| 5,981,497 A | 11/1999 | Maingault |
| 6,057,302 A | 5/2000 | Borzeix |
| 10,065,982 B2 | 9/2018 | Hirata et al. |
| 2004/0171512 A1 | 9/2004 | Furuta et al. |

(Continued)

FOREIGN PATENT DOCUMENTS

| | | |
|---|---|---|
| EP | 2351847 A1 | 8/2011 |
| JP | H07-11/82874 A | 5/1995 |

(Continued)

OTHER PUBLICATIONS

International Search Report and Written Opinion dated Nov. 11, 2014 for Application No. PCT/JP2014/070788.

(Continued)

*Primary Examiner* — Snigdha Maewall
(74) *Attorney, Agent, or Firm* — Wolf, Greenfield & Sacks, P.C.

(57) ABSTRACT

The present invention provides a low-toxicity sophorolipid-containing composition. The low-toxicity sophorolipid-containing composition contains at least a coloring component, an acidic sophorolipid, a fatty acid, and a hydroxy fatty acid that are derived from an SL-producing yeast culture. The composition contains the following components in the following proportions, in terms of dry weight, based on the total amount of the acidic sophorolipid, a lactonic sophorolipid, the fatty acid, and the hydroxy fatty acid in the composition taken as 100 mass %:

(1) acidic sophorolipid: 94 to 99.99 mass %,
(2) lactonic sophorolipid: 0 to 2 mass %,
(3) total amount of fatty acid and hydroxy fatty acid: 0.01 to 4 mass %.

18 Claims, 3 Drawing Sheets

(56) References Cited

U.S. PATENT DOCUMENTS

| | | |
|---|---|---|
| 2011/0237531 A1 | 9/2011 | Yanagisawa et al. |
| 2012/0142621 A1 | 6/2012 | Falus et al. |
| 2012/0220464 A1 | 8/2012 | Giessler-Blank et al. |
| 2013/0035403 A1 | 2/2013 | Schaffer et al. |
| 2015/0112049 A1 | 4/2015 | Hirata et al. |
| 2016/0280733 A1 | 9/2016 | Araki et al. |

FOREIGN PATENT DOCUMENTS

| | | |
|---|---|---|
| JP | H10-501260 A | 2/1998 |
| JP | H11-508549 A | 7/1999 |
| JP | 2002-045195 A | 2/2002 |
| JP | 2003-009896 A | 1/2003 |
| JP | 2003-013093 A | 1/2003 |
| JP | 2006-070231 A | 3/2006 |
| JP | 2006-083238 A | 3/2006 |
| JP | 2008-247845 A | 10/2008 |
| JP | 2009-062288 A | 3/2009 |
| JP | 2009-531310 A | 9/2009 |
| JP | 2009-275145 A | 11/2009 |
| JP | 2006-212086 A | 11/2012 |
| JP | 2013-511266 A | 4/2013 |
| WO | WO 2007/130738 A1 | 11/2007 |
| WO | WO 2010/050413 A1 | 5/2010 |
| WO | WO 2011/061032 A2 | 5/2011 |
| WO | WO 2011/127101 A1 | 10/2011 |
| WO | WO 2013/129667 A1 | 9/2013 |

OTHER PUBLICATIONS

International Search Report and Written Opinion dated Dec. 2, 2014 for Application No. PCT/JP2014/073356.

[No Author Listed] Altern. Animal Test. Experiment, Guideline Draft. Dec. 1998 Dec;(Supplement):1-3.

Ashby et al., Property control of sophorolipids: influence of fatty acid substrate and blending. Biotechnol Lett. Jun. 2008;30(6):1093-100. doi: 10.1007/s10529-008-9653-1. Epub Feb. 9, 2008.

Asmer et al., Microbial production, structure elucidation and bioconversion of sophorose lipids. J American Oil Chem Soc. Sep. 1988;65(9):1460-6.

Brakemeier et al., *Candida bombicola*: production of novel alkyl glycosides based on glucose/2-dodecanol. Appl Microbiol Biotechnol. 1998;50:161-6.

Cavalero et al., The effect of medium composition on the structure and physical state of sophorolipids produced by *Candida bombicola* ATCC 22214. J Biotech. 2003;103:31-41.

Cooper et al., Production of a Biosurfactant from Torulopsis bombicola. Appl Environ Microbiol. Jan. 1984;47(1):173-6.

Daverey et al. Production, characterization, and properties of sophorolipids from the yeast *Candida bombicola* using a low-cost fermentative medium. Appl Biochem Biotechnol. Sep. 2009;158(3):663-74. doi: 10.1007/s12010-008-8449-z. Epub Dec. 10, 2008.

Davila et al., Kinetics and balance of a fermentation free from product inhibition: sophorose lipid production by Candida bombicola. Appl Microbil Biotechnol. 1992;38:6-11.

Davila et al., Identification and determination of individual sophorolipids in fermentation products by gradient elution high-performance liquid chromatography with evaporative light-scattering detection. J Chromatogr. Oct. 1, 1993;648(1):139-49.

Deshpande et al., Evaluation of sophorolipid biosurfactant production by Candida bombicola using animal fat. Bioresource Tech. 1995;54(2):143-150.

Gorin et al., Hydroxy Fatty Acid Glycosides of Sophorose from Torulopsis Magnoliae. Can. J. Chem. 1961;39(4):846-55. doi:10.1139/v61-104.

Hirata et al., Natural synergism of acid and lactone type mixed sophorolipids in interfacial activities and cytotoxicities. Journal of Oleo Science, 2009;58(9):565-72.

Hommel, Formation and physiological role of biosurfactants produced by hydrocarbon-utilizing microorganisms. Biosurfactants in hydrocarbon utilization. Biodegradation. 1990;1(23):107-19. Review.

Nuñez et al., LC/MS analysis and lipase modification of the sophorolipids produced by Rhodotorula bogoriensis. Biotechnol Lett. Jul. 2004;26(13):1087-93.

Okamoto, Recent developments of Draize eye test alternative in Japan. Fragrance Journal 2005-2;67-71.

Tulloch et al., A new hydroxy fatty acid sophoroside from *Candida bogoriensis*. Can J Chem. Feb. 1, 1968;46(3):345-8.

Saerens et al., One-step production of unacetylated sophorolipids by an acetyltransferase negative Candida bombicola. Biotechnol Bioeng. Dec. 2011;108(12):2923-31. doi:10.1002/bit.23248. Epub Jul. 12, 2011.

Shah et al., Sophorolipids, microbial glycolipids with anti-human immunodeficiency virus and sperm-immobilizing activities. Antimicrob Agents Chemother. Oct. 2005;49(10):4093-100.

Van Bogaert et al., Microbial production and application of sophorolipids. Appl Microbiol Biotechnol. Aug. 2007;76(1):23-34. Epub May 3, 2007. Review.

Zhou et al., Production of sophorose lipids by Torulopsis bombicola from safflower oil and glucose. J American Oil Chem Soc. Jan. 1992;69(1):89-91.

Zhou et al., Supramolecular assemblies of a naturally derived sophorolipid. Langmuir. Sep. 14, 2004;20(19):7926-32.

Extended European Search Report dated Nov. 16, 2016 for Application No. EP 14834955.8.

Ma et al., Effects of nitrogen sources on production and composition of sophorolipids by *Wickerhamiella domercqiae* var. *sophorolipid* CGMCC 1576. Appl Microbiol Biotechnol. Sep. 2011;91(6):1623-32. doi: 10.1007/s00253-011-3327-y.

Tulloch et al., Structure and reactions of lactonic and acidic sophorosides of 17-hydroxyoctadecanoic acid. Can J Chem. Feb. 1, 1968;46:3337-51.

EP 14843085.3, Feb. 23, 2017, Extended European Search Report.

Gu et al., A study of the scale-up of reversed-phase liquid chromatography. Separation Purification Tech. Jan. 4, 1999;15:41-58.

Rau et al., Sophorolipids: a source for novel compounds. Industrial Crops Products. Mar. 2001;13(2):85-92.

U.S. Appl. No. 14/382,480, filed Sep. 2, 2014, Hirata et al.

U.S. Appl. No. 14/911,174, filed Feb. 9, 2016, Araki et al.

Daniel et al., Sophorolipid Production with High Yields on Whey Concentrate and Rapeseed Oil without Consumption of Lactose. Biotech Lett. Aug. 1998;20(8):805-807.

Examination Report for EP Application No. 148349558 dated Jul. 21, 2017.

Shah et al., Utilization of restaurant waste oil as a precursor for sophorolipid production. Biotechnol Prog. Mar.-Apr. 2007;23(2):512-5. Epub Feb. 8, 2007.

Chinese Office Action dated Oct. 29, 2018 for Application No. CN 201480054091.5.

Liu et al., Progress on biosynthesis and application of sophorolipids. Food Drug. Nov. 2009;11(11):51-5.

Song et al., Structure characterization and physi-chemical properties of sophorolipid biosurfactants. Environmental Chemistry. Aug. 2011;30(8):1474-79.

U.S. Appl. No. 14/911,174, filed May 23, 2016, Araki et al.

2018-568976, dated Jan. 22, 2019, Japanese Notice of Reasons for Refusal.

Notice of Reasons for Refusal for Japanese Application No. 2018-568976 dated Jan. 22, 2019.

[Fig. 2]
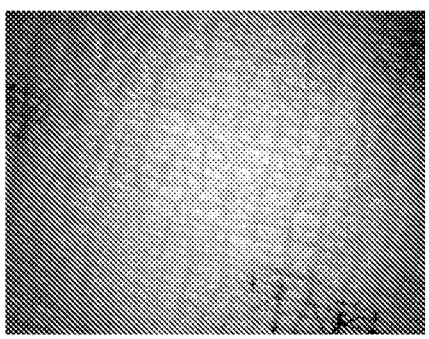 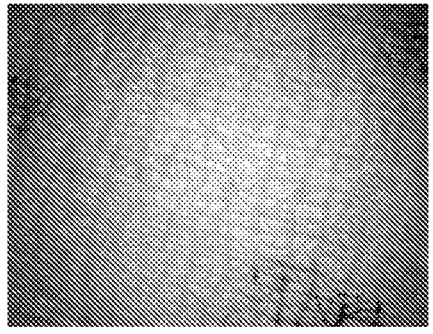
After treatment with 5% SDS     Low toxicity SL (after 4 days)

[Fig. 3]
(A)
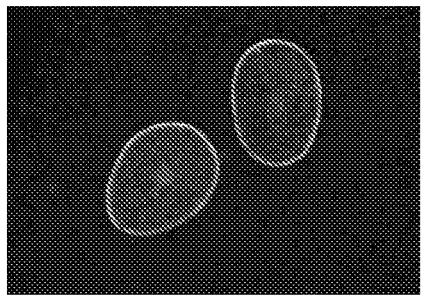
Water
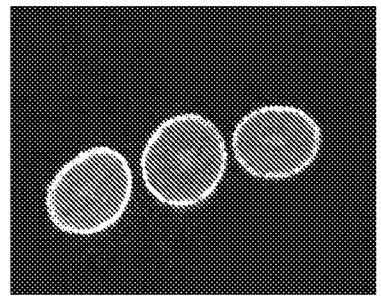
Low-toxicity SL
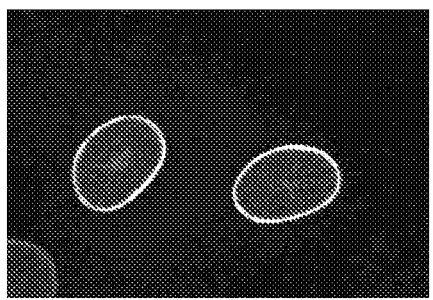
Aqulio TXF-875
(B)
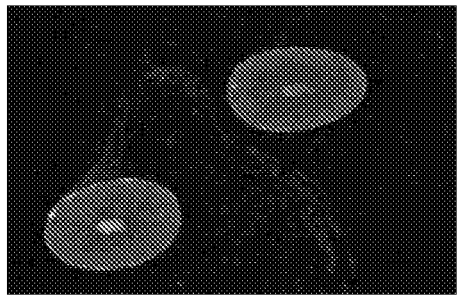
Water
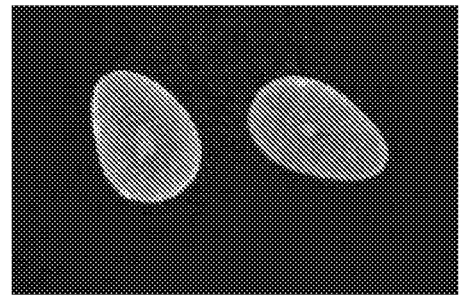
Low-toxicity SL
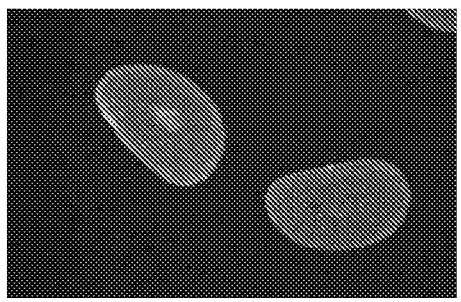
Aqulio TXF-875

LOW-TOXICITY SOPHOROLIPID-CONTAINING COMPOSITION AND USE THEREFOR

RELATED APPLICATIONS

The present application is a continuation-in-part of International PCT Application, PCT/JP2014/073356, filed Sep. 4, 2014, which claims priority to Japanese application 2013-183463, filed Sep. 4, 2013, each of which is incorporated herein by reference.

TECHNICAL FIELD

The present invention relates to a low-toxicity sophorolipid-containing composition, and use thereof.

BACKGROUND ART

In recent years, with the increased focus on cleanliness, surfactants have frequently been used for washing hair and/or cleaning skin. On the other hand, the number of consumers who suffer from hand roughness and dermatitis caused by frequent use of surfactants has also been increasing. In fact, the Ministry of Health, Labour and Welfare's patient census (separated according to disease categories) show that the number of atopic dermatitis patients increased from 224,000 in 1987 to 399,000 in 2009, and that 369,000 patients existed in 2011. This suggests that the number of consumers who suffer daily from damage by surfactants (such as dry-skin feeling, rough skin, skin cracks, eczema, dry-hair feeling, etc.) can be potentially large.

Under such circumstances, amino acid surfactants such as N-acyl-L-glutamic acid triethanolamine, and polyglycerol fatty acid ester surfactants such as polyglyceryl laurate are increasingly used as relatively safer surfactants. As it causes fewer safety problems, soap (fatty acid salt) has been reconsidered. However, medium-chain fatty acids having a carbon chain length of 6 to 10 carbon atoms, such as soaps, are known to be highly irritating. Among the above surfactants, amino acid surfactants are known to be relatively less irritating (low irritation); however, even these surfactants are not completely satisfactory.

Biosurfactants, which are surfactants derived from living organisms, have high biodegradability and high safety and are therefore expected to be used industrially as next-generation surfactants. Among these, sophorolipids, which are a type of glycolipid biosurfactant, are fermentation products that are obtained from fermentation of yeast and known to be highly safe. For example, Patent Literature (PTL) 1 discloses that sophorolipids have a low degree of irritation. However, the degree of low irritation of the sophorolipids disclosed therein is equivalent to that of amino acid surfactants, and further reducing irritation (toxicity reduction) is desired. Furthermore, lactonic sophorolipids, which are a form of sophorolipid, are known to be relatively toxic (Non-patent Literature (NPL) 1).

CITATION LIST

Patent Literature

PTL 1: JP2009-275145A

Non-patent Literature

NPL 1: Shah V, Doncel G F, Seyoum T, Eaton K M, Zalenskaya I, Hagver R, Azim A, Gross R (2005), Sophorolipids, Microbial Glycolipids with Anti-Human Immunodeficiency Virus and Sperm-Immobilizing Activities. Antimicrob. Agents Chemother. 49 (10), 4093-4100

NPL 2: Karen M. J. Saerens, Lien Saey, Wim Soetaert (2011), One-Step Production of Unacetylated Sophorolipids by an Acetyltransferase Negative *Candida bombicola*. Biotechnol. Bioeng. 108 (12). 2923-2931

SUMMARY OF INVENTION

Technical Problem

An object of the present invention is to provide a low-toxicity sophorolipid-containing composition. Another object of the present invention is to provide use of the low-toxicity sophorolipid-containing composition. The "low-toxicity sophorolipid-containing composition" as used herein refers to a low-toxicity composition containing low-toxicity sophorolipids.

Solution to Problem

The present inventors conducted extensive research to solve the above-stated problem. As a result, the inventors found that among the components contained in a sophorolipid-containing composition produced by yeast fermentation, not only lactonic sophorolipids but also each of fatty acids, hydroxy fatty acids, and acetyl groups contained in acidic sophorolipids considerably affects the cytotoxicity of the sophorolipid-containing composition. The present inventors confirmed that the removal of these substances can provide a less-toxic sophorolipid-containing composition, in particular a sophorolipid-containing composition having extremely low irritation to the eyes, oral cavity, and other mucosal sites (e.g., throat, nasal cavities, aural cavities, reproductive organs, and anus), and wound sites (a low-toxicity sophorolipid-containing composition).

The inventors found that when applied to the skin or hair, this low-toxicity sophorolipid-containing composition is free of problems of tautness and squeakiness, and also has moisturizing effects, protects the skin and hair (has skin protection and hair protection effects), and can repair hair, thereby moisturizing the skin and preventing damage to the skin and hair.

The present invention has been accomplished based on the above finding, and includes the following embodiments. Hereinafter, "sophorolipid" may be abbreviated as "SL." Specifically, the "low-toxicity sophorolipid-containing composition" of the present invention may also be referred to as a "low-toxicity SL-containing composition." The term "sophorolipid" as referred to herein includes both a single type of sophorolipid and a mixture comprising different types of sophorolipids. Both may be collectively referred to as "sophorolipid" or "SL," unless otherwise specified.

(I) Low-toxicity SL-containing Composition (I-1) A low-toxicity SL-containing composition containing at least a coloring component, an acidic SL, a fatty acid, and a hydroxy fatty acid that are derived from an SL-producing yeast culture, the following components being in the following proportions, in terms of dry weight, based on the total amount of the acidic SL, a lactonic SL, the fatty acid, and the hydroxy fatty acid in the composition taken as 100 mass %:

(1) acidic SL: 94 to 99.99 mass %,
(2) lactonic SL: 0 to 2 mass %, (3) fatty acid and hydroxy fatty acid in total: 0.01 to 4 mass %.

(I-2) A low-toxicity SL-containing composition having the following features (a) to (c):
(a) the composition contains at least an acidic SL, a fatty acid, and a hydroxy fatty acid that are derived from an SL-producing yeast culture, the following components being in the following proportions, in terms of dry weight, based on the total amount of the acidic SL, a lactonic SL, the fatty acid, and the hydroxy fatty acid in the composition taken as 100 mass %:
(1) acidic SL: 94 to 99.99 mass %,
(2) lactonic SL: 0 to 2 mass %,
(3) fatty acid and hydroxy fatty acid in total: 0.01 to 4 mass %;
(b) the proportion of the lactonic SL is 0 to 2.12 parts by mass, or the (total) proportion of the fatty acid and hydroxy fatty acid is 0.01 to 4.25 parts by mass, relative to 100 parts by mass of the acidic SL contained in the low-toxicity SL-containing composition;
(c) neither the acidic SL nor the lactonic SL contained in the low-toxicity SL-containing composition has an acetyl group.

(I-3) The low-toxicity SL-containing composition according to (I-1) or (I-2), wherein the proportion of the lactonic SL and the total proportion of the fatty acid and hydroxy fatty acid satisfy at least one of the following (i) and (ii), based on the total amount of the acidic SL, lactonic SL, fatty acid, and hydroxy fatty acid in the composition taken as 100 mass %:
(i) lactonic SL: preferably more than 0 mass % but not more than 2 mass %, more preferably 0.1 to 2 mass %, even more preferably 0.1 to 1.5 mass %, and particularly preferably 0.8 to 1.5 mass %; and
(ii) fatty acid and hydroxy fatty acid (in total): preferably 0.01 to 2.4 mass %, more preferably 0.01 to 1.2 mass %, and even more preferably 0.01 to 0.24 mass %.

(I-4) The low-toxicity SL-containing composition according to (I-1) or (I-2), wherein the proportion of the acidic SL, the proportion of the lactonic SL, and the total proportion of the fatty acid and hydroxyl fatty acid are as follows, based on the total amount of the acidic SL, lactonic SL, fatty acid, and hydroxy fatty acid in the composition taken as 100 mass %:
(i) acidic SL: preferably 96.1 mass % or more, more preferably 97.9 mass % or more, and even more preferably 99.31 mass % or more,
(ii) lactonic SL: preferably more than 0 mass % but not more than 2 mass %, more preferably 0.1 to 2 mass %, even more preferably 0.1 to 1.5 mass %, and particularly preferably 0.8 to 1.5 mass %, and
(iii) fatty acid and hydroxy fatty acid (in total): 0.01 to 2.4 mass %, more preferably 0.01 to 1.2 mass %, and even more preferably 0.01 to 0.24 mass %.

(I-5) The low-toxicity SL-containing composition according to any one of (I-1) to (I-4), wherein the proportion of the acidic SL is 98 to 100 mass %, preferably 98.5 to 100 mass %, more preferably 99 to 100 mass %, and even more preferably 99.5 to 100 mass %, and the proportion of the lactonic SL is 0 to 2 mass %, preferably 0 to 1.5 mass %, and more preferably 0 to 1 mass %, based on the total amount of the acidic SL and lactonic SL in the composition taken as 100 mass %.

(I-6) The low-toxicity SL-containing composition according to any one of (I-1) to (I-5), wherein an aqueous solution prepared by dissolving the low-toxicity sophorolipid-containing composition so that the solution has an ethanol-soluble content of 10 mass % has an absorbance at a wavelength of 440 nm (hue: $OD_{440}$) of 0.001 to 1, preferably 0.005 to 0.8, more preferably 0.01 to 0.6, particularly preferably 0.01 to 0.5, and further particularly preferably 0.4 or less.

(I-7) The low-toxicity SL-containing composition according to any one of (I-1) to (I-6), wherein the composition in an amount corresponding to 1 g of its ethanol-soluble content has an ester value of 0.01 to 2 mg KOH/g, preferably 0.01 to 1.5 mg KOH/g, more preferably 0.1 to 1.5 mg KOH/g, and particularly preferably 0.8 to 1.5 mg KOH/g.

(I-8) The low-toxicity SL-containing composition according to any one of (I-1) to (I-7), wherein the composition in an amount corresponding to 1 g of its ethanol-soluble content has a hydroxyl value of 460 to 630 mg KOH/g, preferably 545 to 630 mg KOH/g, more preferably 560 to 630 mg KOH/g, particularly preferably 575 to 630 mg KOH/g, and further particularly preferably 575 to 585 mg KOH/g.

(I-9) The low-toxicity SL-containing composition according to any one of (I-1) to (I-8), wherein the composition has a HeLa cell lethal concentration ($IC_{50}$) of 2,000 ppm or more, and preferably 3,000 to 60,000 ppm.

(I-10) The low-toxicity SL-containing composition according to any one of (I-1) to (I-9), wherein the composition has a HeLa cell lethal concentration ($IC_{50}$)/critical micelle concentration (CMC) ratio ($IC_{50}$/CMC) of 6.7 to 200, preferably 10 to 200, more preferably 17 to 200, and particularly preferably 33 to 200.

(I-11) The low-toxicity SL-containing composition according to any one of (I-1) to (I-10), wherein the composition has at least one of the following physical properties (a) to (c):
(a) evaporation residue: 1 to 100%;
(b) loss on drying: 0 to 99%; and
(c) ethanol-soluble content: 1 to 100%.

(I-12) The low-toxicity SL-containing composition according to any one of (I-1) to (I-11), wherein the composition has an infrared absorption spectrum comprising infrared absorption bands at least at wavelengths of around 1024 $cm^{-1}$, around 1706 to 1730 $cm^{-1}$, around 2854 $cm^{-1}$, around 2924 $cm^{-1}$, and around 3000 to 3500 $cm^{-1}$.

(I-13) The low-toxicity SL-containing composition according to any one of (I-1) to (I-12), wherein the composition has a solid form.

(I-14) The low-toxicity SL-containing composition according to (I-13), wherein the solid form is a powder or a granule.

(II) Use of the Low-toxicity SL-containing Composition (II-1) An anionic surfactant comprising as an active component the low-toxicity SL-containing composition according to any one of (I-1) to (I-14).

(II-2) A fragrance or cosmetic, a food or beverage, a drug, a quasi-drug, a medical device, a household supply item, or an additive for fragrances or cosmetics, foods or beverages, drugs, quasi-drugs, medical devices, or household supply items, comprising the low-toxicity SL-containing composition according to any one of (I-1) to (I-14).

(II-3) The fragrance or cosmetic, food or beverage, drug, quasi-drug, medical device, household supply item, or additive for fragrances or cosmetics, foods or beverages, drugs, quasi-drugs, medical devices, or household supply items according to (II-2), wherein the fragrance or cosmetic, food or beverage, drug, quasi-drug, medical device, or household supply item is applied to the skin, hair, mucosa, or a wound site (such as a wound or a site of inflammation).

(II-4) The fragrance or cosmetic, food or beverage, drug, quasi-drug, medical device, household supply item, or additive for fragrances or cosmetics, foods or beverages, drugs, quasi-drugs, medical devices, or household supply items according to (II-2) or (II-3), wherein the fragrance or cosmetic, food or beverage, drug, quasi-drug, medical device, or household supply item is at least one item selected from the group consisting of body washes, hair washes, eye washes, eye drops, cosmetics, oral cavity washes, mucosal or wound cleansers, and wound dressings.

(II-5) The fragrance or cosmetic, drug, quasi-drug, medical device, household supply item, or additive for fragrances or cosmetics, foods or beverages, drugs, quasi-drugs, medical devices, or household supply items according to (II-4), wherein the low-toxicity SL-containing composition according to any one of (I-1) to (I-14) is contained in the following proportions:

body wash: 0.01 to 100 mass %,
hair wash: 0.01 to 30 mass %,
eye wash: 0.001 to 10 mass %,
eye drop: 0.001 to 10 mass %,
cosmetic: 0.01 to 20 mass %,
oral-cavity wash: 0.001 to 10 mass %,
mucosa or wound cleanser: 0.001 to 30 mass %,
wound dressing: 0.001 to 30 mass %.

(II-6) A skin moisturizer, an agent for ameliorating skin roughness, a skin protectant, or a hair protectant, comprising the low-toxicity SL-containing composition according to any one of (I-1) to (I-14).

Further, the present invention includes methods for producing the low-toxicity sophorolipid-containing composition, and methods for reducing the toxicity of a sophorolipid-containing composition.

(III) Method for Producing the Low-toxicity SL-containing Composition (III-1) A method for producing the low-toxicity SL-containing composition according to any one of (I-1) to (I-14), the method comprising subjecting an SL-containing culture obtained by culturing an SL-producing yeast, or a treated product of the culture, to a step of (1) removing fatty acids and/or hydroxy fatty acids.

(III-2) The production method according to (III-1), wherein the SL-containing culture obtained by culturing the SL-producing microorganism, or the treated product of the culture, is further subjected to at least one of the steps of (2) removing acetyl groups bound to SLs, and (3) removing lactonic SLs.

(III-3) The production method according to (III-1) or (III-2), wherein the step of (1) removing fatty acids and/or hydroxy fatty acids comprises at least one treatment selected from solvent extraction, adsorption, and chromatography.

(III-4) The production method according to (III-3), wherein the solvent extraction is an extraction method using diethyl ether as a solvent; the adsorption is a method using activated carbon, silica gel, zeolite, an ion-exchange resin, or aluminum oxide as an adsorbent; and the chromatography is reverse-phase column chromatography using an ODS resin as a stationary phase and using an aqueous ethanol solution as a mobile phase.

(III-5) The production method according to any one of (III-1) to (III-4), wherein the step of (2) removing acetyl groups bound to SLs comprises at least one treatment selected from hydrolysis and enzyme treatment.

(III-6) The production method according to (III-5), wherein the enzyme treatment uses acetyl esterase.

(III-7) The production method according to any one of (III-1) to (III-6), wherein the step of (3) removing lactonic SLs is at least one treatment selected from hydrolysis and chromatography.

(III-8) The production method according to (III-7), wherein the chromatography is reverse-phase column chromatography using an ODS resin as a stationary phase and an aqueous ethanol solution as a mobile phase.

(IV) Method for Reducing the Toxicity of an SL-containing Composition (IV-1) A method for reducing the toxicity of an SL-containing composition, the method comprising subjecting an SL-containing culture obtained by culturing an SL-producing yeast, or a treated product thereof, to a step of (1) removing fatty acids and/or hydroxy fatty acids to produce a low-toxicity SL-containing composition in which the following components are in the following proportions, in terms of dry weight, based on the total amount of acidic SL, lactonic SL, fatty acid, and hydroxy fatty acid in the composition taken as 100 mass %:

(a) acidic SL: 94 to 99.99 mass %;
(b) lactonic SL: 0 to 2 mass %; and
(c) fatty acid and hydroxy fatty acid in total: 0.01 to 4 mass %.

(IV-2) The toxicity reduction method according to (IV-1), wherein the low-toxicity SL-containing composition produced further has at least one of the following features:

(i) the proportion of the lactonic SL is 0 to 0.212 parts by mass or the (total) proportion of the fatty acid and hydroxy fatty acid is 0.01 to 4.25 parts by mass, relative to 100 parts by mass of the acidic SL contained in the low-toxicity SL-containing composition; and (ii) neither the acidic SL nor the lactonic SL contained in the low-toxicity SL-containing composition has an acetyl group.

(IV-3) The toxicity reduction method according to (IV-1) or (IV-2), wherein the method produces a low-toxicity SL-containing composition in which the proportion of the lactonic SL and the (total) proportion of the fatty acid and hydroxy fatty acid satisfy at least one of the following (i) and (ii), based on the total amount of the acidic SL, lactonic SL, fatty acid, and hydroxy fatty acid in the composition taken as 100 mass %:

(i) lactonic SL: preferably more than 0 mass % but not more than 2 mass %, more preferably 0.1 to 2 mass %, even more preferably 0.1 to 1.5 mass %, and particularly preferably 0.8 to 1.5 mass %; and (ii) fatty acid and hydroxy fatty acid (in total): preferably 0.01 to 2.4 mass %, more preferably 0.01 to 1.2 mass %, and even more preferably 0.01 to 0.24 mass %.

(IV-4) The toxicity reduction method according to any one of (IV-1) to (IV-3), wherein the method produces a low-toxicity SL-containing composition in which the proportion of the acidic SL, the proportion of the lactonic SL, and the total proportion of the fatty acid and hydroxyl fatty acid are as follows, based on the total amount of the acidic SL, lactonic SL, fatty acid, and hydroxy fatty acid in the composition taken as 100 mass %:

(a) acidic SL: preferably 96.1 mass % or more, more preferably 97.9 mass % or more, and even more preferably 99.31 mass % or more;

(b) lactonic SL: preferably more than 0 but not more than 2 mass %, more preferably 0.1 to 2 mass %, even more preferably 0.1 to 1.5 mass %, and particularly preferably 0.8 to 1.5 mass %; and (c) fatty acid and hydroxy fatty acid (in total): preferably 0.01 to 2.4 mass %, more preferably 0.01 to 1.2 mass %, and even more preferably 0.01 to 0.24 mass %.

(IV-5) The toxicity reduction method according to any one of (IV-1) to (IV-4), wherein the method produces a low-toxicity SL-containing composition in which the proportion of the acidic SL is 98 to 100 mass %, preferably 98.5 to 100 mass %, more preferably 99 to 100 mass %, and particularly preferably 99.5 to 100 mass %, and the proportion of the lactonic SL is 0 to 2 mass %, preferably 0 to 1.5 mass %, and more preferably 0 to 1 mass %, based on the total amount of the acidic SL and lactonic SL taken as 100 mass %.

(IV-6) The toxicity reduction method according to any one of (IV-1) to (IV-5), wherein the method produces a low-toxicity SL-containing composition, the composition in an amount corresponding to 1 g of its ethanol-soluble content having an ester value of 0.01 to 2 mg KOH/g, preferably 0.01 to 1.5 mg KOH/g, more preferably 0.1 to 1.5 mg KOH/g, and particularly preferably 0.8 to 1.5 mg KOH/g.

(IV-7) The toxicity reduction method according to any one of (IV-1) to (IV-6), wherein the method produces a low-toxicity SL-containing composition, the composition in an amount corresponding to 1 g of its ethanol-soluble content having 460 to 630 mg KOH/g, preferably 545 to 630 mg KOH/g, more preferably 560 to 630 mg KOH/g, particularly preferably 575 to 630 mg KOH/g, and more particularly preferably 575 to 585 mg KOH/g.

(IV-8) The toxicity reduction method according to any one of (IV-1) to (IV-7), wherein the SL-containing culture obtained by culturing an SL-producing microorganism, or a treated product of the culture, is further subjected to at least one of the steps of (2) removing acetyl groups bound to SLs, and (3) removing lactonic SLs.

(IV-9) The toxicity reduction method according to any one of (IV-1) to (IV-8), wherein the step of (1) removing fatty acids and/or hydroxy fatty acids comprises at least one treatment selected from solvent extraction, adsorption, and chromatography.

(IV-10) The toxicity reduction method according to (IV-9), wherein the solvent extraction is a method using diethyl ether as a solvent; the adsorption is a method using activated carbon, silica gel, zeolite, ion-exchange resin, or aluminum oxide as an adsorbent; and the chromatography is reverse-phase column chromatography using an ODS resin as a stationary phase and an aqueous ethanol solution as a mobile phase.

(IV-11) The toxicity reduction method according to any one of (IV-8) to (IV-10), wherein the step of (2) removing acetyl groups bound to SLs comprises at least one treatment selected from hydrolysis and enzyme treatment.

(IV-12) The toxicity reduction method according to (IV-11), wherein the enzyme treatment uses acetyl esterase.

(IV-13) The toxicity reduction method according to any one of (IV-8) to (IV-12), wherein the step of (3) removing lactonic SLs is at least one treatment selected from hydrolysis and chromatography.

(IV-14) The toxicity reduction method according to (IV-13), wherein the chromatography is reverse-phase column chromatography using an ODS resin as a stationary phase and an aqueous ethanol solution as a mobile phase.

Advantageous Effects of Invention

According to the present invention, an SL-containing composition having low cytotoxicity can be provided. The low-toxicity SL-containing composition of the present invention has surfactant effects and also has extremely low cytotoxicity and extremely low irritation to the eyes, mucosa, and wound sites (low toxicity and low irritation). Therefore, the composition of the present invention can be suitably incorporated into cosmetics, drugs, quasi-drugs, medical devices, and the like applied to the skin, ocular mucosa, oral mucosa, or other mucosal sites (such as the throat, nasal cavity, aural cavity, reproductive organs, and anus), and wound sites (such as wounds and sites of inflammation). Specifically, the low-toxicity SL-containing composition of the present invention can be incorporated into eye drops, eye lotions, contact lens fitting liquids, and like eye-care products applied to the ocular mucosa, oral medicaments for application to the oral mucosa, nasal medicaments such as nasal sprays applied to the nasal mucosa, etc.

Therefore, cosmetics, drugs, and quasi-drugs containing the low-toxicity (low-irritation) SL-containing composition of the present invention can be suitably applied not only to the skin but also to ocular mucosa, oral mucosa, and other mucosal sites (such as the throat, nasal cavity, aural cavity, reproductive organs, and anus) and wound sites (such as wounds and sites of inflammation).

Further, since the low-toxicity (low-irritation) SL-containing composition of the present invention has a moisturizing effect, effects of protecting the skin and hair, and a skin barrier function improvement effect, the composition can be applied not only to the mucosal sites and wound sites mentioned above but also can be suitably used for protecting the skin and hair or giving moisture.

BRIEF DESCRIPTION OF DRAWINGS

FIG. 2 shows amelioration effects on rough skin caused by treating a human upper arm with SDS.

FIG. 3(A) shows a hair-protecting effect on healthy hair. FIG. 3(B) shows a hair-repairing effect on damaged hair.

Figure 1:
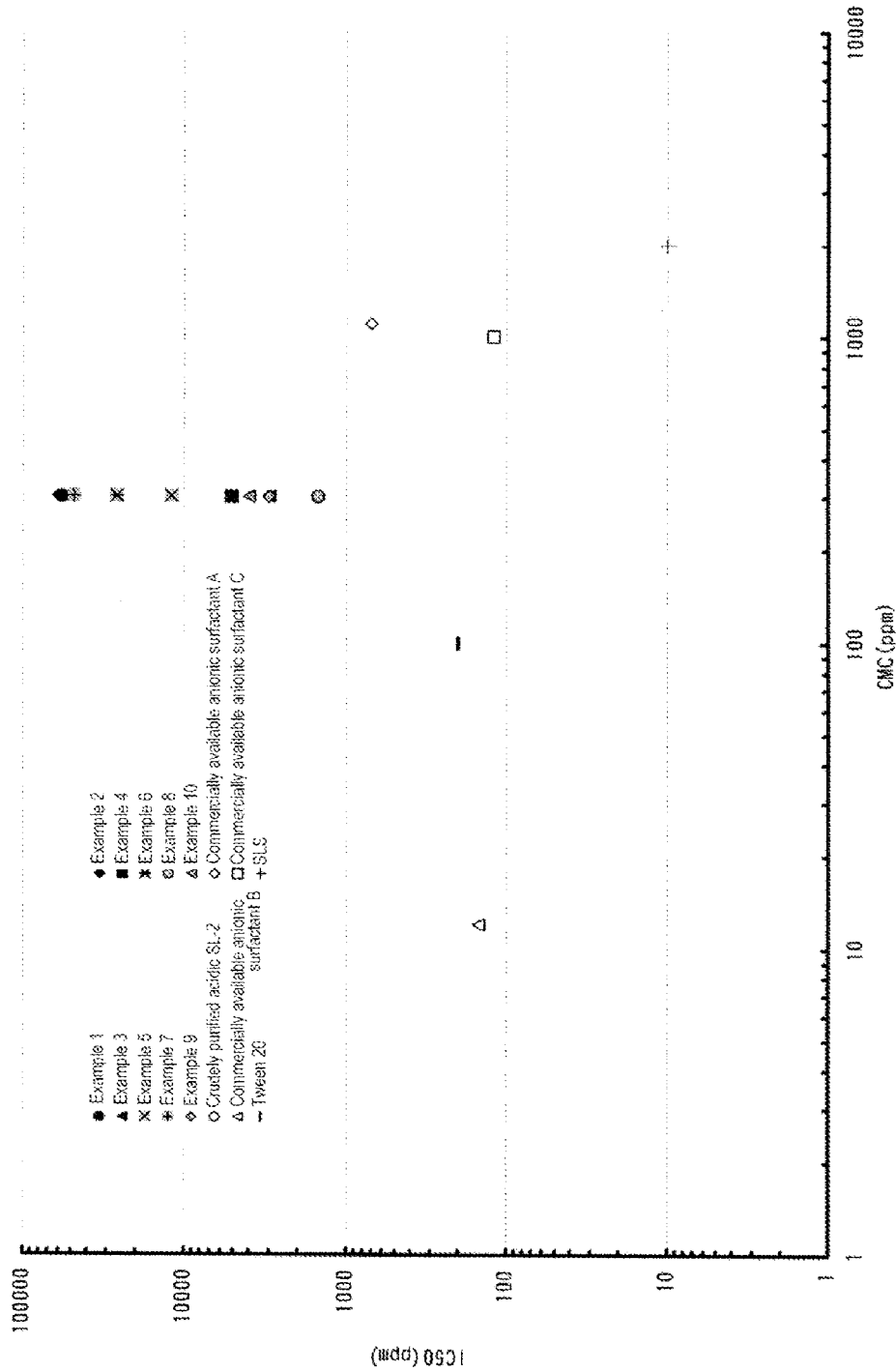
FIG. 1 shows a graph plotting the cell lethal concentration ($IC_{50}$) versus CMC. The cell lethal concentration ($IC_{50}$) was calculated from a cytotoxicity test using SL-containing compositions obtained in Reference Production Example 2 and Examples 1 to 10 (crudely purified SL-containing composition-2 and Example products 1 to 10), Tween 20, and commercially available anionic surfactants A to C (A: "Amisoft LT-12" (30%): produced by Ajinomoto Co., Inc., B: "Surfactin Na" (100%): produced by Wako Pure Chemical Industries, Ltd., C: "Lipolan LJ-441" (37%): produced by Lion Corporation), and SLS. The CMC was calculated in Test Example 2.

DESCRIPTION OF EMBODIMENTS (I) General Sophorolipids (Known SLs)

Sophorolipid (SL) is generally a glycolipid consisting of a hydroxyl fatty acid, and sophorose or a sophorose whose one or more hydroxyl groups are acetylated. Sophorose is a sugar consisting of two glucose molecules bound through a β1→2 bond. A hydroxyl fatty acid is a fatty acid having a hydroxyl group. SL is roughly classified into acidic SL (General Formula (1)) and lactonic SL (General Formula (2)). Acidic SL is a sophorolipid in which the carboxyl group of the hydroxy fatty acid is free. Lactonic SL is a sophorolipid in which the carboxyl group of the hydroxy fatty acid is bound to the sophorose in the molecule. The SL obtained from a certain species of yeast (SL-producing yeast) through fermentation is ordinarily a mixture of SLs represented by the following General Formula (1) and SLs represented by the following General Formula (2), and is obtained as a collection of 30 or more types of structural homologues having different fatty acid chain lengths ($R^3$), and having an acetylation or protonation at the 6'-position ($R^2$) and the 6"-position (R) of the sophorose.

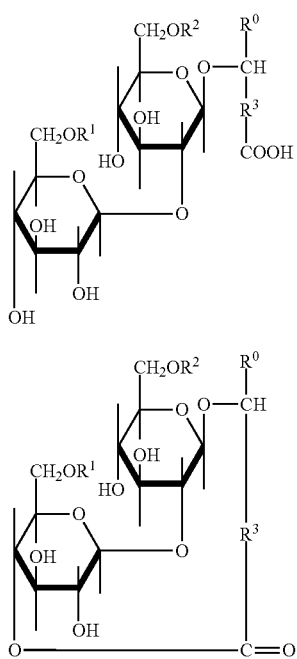

In General Formula (1) or (2), $R^0$ is either a hydrogen atom or a methyl group. $R^1$ and $R^2$ are each independently a hydrogen atom or an acetyl group. $R^3$ is a saturated aliphatic hydrocarbon chain, or an unsaturated aliphatic hydrocarbon chain having at least one double bond, and may have one or more substituents. Examples of the substituents include halogen atoms, hydroxyl, lower ($C_{1-6}$) alkyl groups, halo lower ($C_{1-6}$) alkyl groups, hydroxy lower ($C_{1-6}$) alkyl groups, halo lower ($C_{1-6}$) alkoxy groups, and the like. $R^3$ typically has 11 to 20 carbon atoms, preferably 13 to 17 carbon atoms, and more preferably 14 to 16 carbon atoms. Examples of the halogen atoms or halogen atoms bound to alkyl groups or alkoxy groups include fluorine, chlorine, bromine, and iodine.

As described above, the culture broth obtained from an SL-producing yeast through fermentation usually contains SL as a mixture of acidic SLs represented by General Formula (1) and lactonic SLs represented by General Formula (2). The ratio of acidic SLs to lactonic SLs in the culture broth may be typically in the range of 45:55 to 10:90 (dry weight ratio).

Examples of preferable SL-producing yeasts include *Candida bombicola*. The *Candida* genus has been renamed the *Starmerella* genus. This yeast is an SL-producing yeast known to produce a significant amount of (acidic and lactonic) SLs (see, for example, Canadian Journal of Chemistry, 39, 846 (1961) (note: the *Torulopsis* genus described in the document belongs to the *Candida* genus, but is currently classified into the *Starmerella* genus, as described above); and Applied and Environmental Microbiology, 47, 173 (1984)). *Candida* (*Starmerella*) *bombicola* has been deposited with, and is available from, bioresource banks, such as the ATCC (*Candida bombicola* ATCC22214 etc.). The low-toxicity SL-containing composition of the present invention can also be produced by using other SL-producing yeasts belonging to the *Candida* genus (*Starmerella* genus) known to produce (acidic and lactonic) SLs. Examples of such SL-producing yeasts include *Candida magnoliae, Candida gropengisseri, Candida apicola, Candida petrophilum, Candida bogoriensis, Candida batistae*, and the like. It has been reported that relatively large amounts of SLs are produced in the culture broth of these yeasts (R. Hommel, Biodegradation, 1, 107 1990).

*Candida floricola* ZM-1502 strain (FERM P-21133) and *Candida floricola* NBRC10700T strain are known to be SL-producing yeasts that selectively produce only acidic SLs (JP2008-247845A). Accordingly, when acidic SLs are to be selectively produced, these SL-producing yeasts can be preferably used.

To culture these SL-producing yeasts, media containing a sugar such as glucose as a carbon source (a hydrophilic substrate); and a fatty acid, a fatty acid ester such as fatty acid triglyceride, or a fat or oil such as a vegetable oil containing a fatty acid as a component (a hydrophobic substrate), are used. Other components of the media are not particularly limited, and can be suitably selected from medium components generally used for yeasts.

(II) Low-toxicity SL-containing Composition

The low-toxicity SL-containing composition according to the present invention is different from the above known SL compositions in at least cytotoxicity (cell stimulation) and skin moisturizing effects, and has the following feature (a) or features (a) to (c).

(a) The composition contains at least an acidic SL, a fatty acid, and a hydroxy fatty acid that are derived from an SL-producing yeast culture, or at least a coloring component, an acidic SL, a fatty acid, and a hydroxy fatty acid that are derived from an SL-producing yeast culture, the following components being in the following proportions, in terms of dry weight, based on the total amount of the acidic SL, a lactonic SL, the fatty acid, and the hydroxy fatty acid in the composition taken as 100 mass %:
(1) acidic SL: 94 to 99.99 mass %,
(2) lactonic SL: 0 to 2 mass %,
(3) fatty acid and hydroxy fatty acid in total: 0.01 to 4 mass %;

(b) the proportion of the lactonic SL is 0 to 2.12 parts by mass, or the (total) proportion of the fatty acid and hydroxy fatty acid is 0.01 to 4.25 parts by mass, relative to 100 parts by mass of the acidic SL contained in the low-toxicity SL-containing composition;

(c) neither the acidic SL nor the lactonic SL contained in the low-toxicity SL-containing composition has an acetyl group.

These features are explained below.

(a) (1) The Proportion of Acidic SL is 94 to 99.99 Mass % in Terms of Dry Weight.

This is the proportion of acidic SL (in terms of dry weight), relative to the total amount (100 mass %) of the acidic SL, lactonic SL, fatty acid, and hydroxy fatty acid contained in the low-toxicity SL-containing composition. This corresponds to the proportion of acidic SL contained in the ethanol-soluble content (100 mass %) of the low-toxicity SL-containing composition. Accordingly, the proportion of acidic SL contained in the ethanol-soluble content (100 mass %) of the low-toxicity SL-containing composition can be said to be 94 to 99.99 mass %. The proportion of the acidic SL is preferably 96.1 mass % or more, more preferably 97.9 mass % or more, and particularly preferably 99.31 mass % or more.

The low-toxicity SL-containing composition of the present invention includes low-toxicity SL-containing compositions (Examples 1 to 10) containing acidic SL in a proportion of 95 to 99.86 mass %. These are merely embodiments of the present invention. The present invention is not limited to these embodiments.

The proportion of acidic SL can be calculated from the ester value and ether extract content of the low-toxicity SL-containing composition. As will be described below, the "ester value" and "ether extract content" as used herein correspond to the proportion of "lactonic SL" and the proportion of "fatty acid and hydroxy fatty acid," relative to the total amount (100 mass %) of the acidic SL, lactonic SL, fatty acid, and hydroxy fatty acid. Accordingly, 100 minus the sum of the "ester value" and "ether extract content" corresponds to the proportion (mass %) of acidic SL contained in the low-toxicity SL-containing composition.

(a) (2) The Proportion of Lactonic SL is 0 to 2 Mass % in Terms of Dry Weight.

This is the proportion of lactonic SL (in terms of dry weight), relative to the total amount (100 mass %) of the acidic SL, lactonic SL, fatty acid, and hydroxy fatty acid contained in the low-toxicity SL-containing composition. This corresponds to the proportion of lactonic SL contained in the ethanol-soluble content (100 mass %) of the low-toxicity SL-containing composition. Accordingly, the proportion of lactonic SL contained in the ethanol-soluble content (100 mass %) of the low-toxicity SL-containing composition can be said to be 0 to 2 mass %. Although the proportion of lactonic SL is preferably as small as possible in view of obtaining a low-toxicity SL-containing composition, containing lactonic SL in an amount in the range of more than 0 but not more than 2 mass % provides good surface tension-reducing ability, and also achieves excellent performance as a surfactant (wettability, solubilization power, detergency, foamability) (see Test Example 5).

Accordingly, when the primary focus is on low toxicity, the proportion (upper limit and lower limit) of the lactonic SLs contained in the ethanol-soluble content (100 mass %) of the low-toxicity SL-containing composition is as follows:
upper limit: preferably 1.5 mass % or less, more preferably 0.9 mass % or less, even more preferably 0.45 mass % or less, and particularly preferably 0.1 mass % or less; and
lower limit: preferably 0 mass % or more. When a lactonic SL-producing yeast is used as the SL-producing yeast, the amount of lactonic SL may be, for example, 0.01 mass % or more.

On the other hand, when a low-toxicity SL-containing composition that has excellent low toxicity while maintaining excellent performance as a surfactant (wettability, solubilization power, detergency, foamability) (hereinafter collectively referred to as "surfactant potency") is to be produced, the proportion (upper and lower limits) of the lactonic SL contained in the ethanol-soluble content (100 mass %) of the low-toxicity SL-containing composition is as follows:
upper limit: preferably 2 mass % or less, and more preferably 1.5 mass % or less;
lower limit: preferably more than 0 mass %, more preferably 0.1 mass % or more, and even more preferably 0.8 mass % or more.

The low-toxicity SL-containing composition of the present invention includes low-toxicity SL-containing compositions containing lactonic SL in an amount of 0.04 to 2.0 mass % (Examples 1 to 10). These are merely embodiments of the present invention. The present invention is not limited to these embodiments.

The proportion of the lactonic SL can be obtained from the ester value (mg KOH/g) of the low-toxicity SL-containing composition.

Specifically, the "ester value (mg KOH/g)" as used herein refers to the amount (mg) of potassium hydroxide required for complete saponification of esters contained in a sample (low-toxicity SL-containing composition in an amount corresponding to 1 g of the ethanol-soluble content. The "ester value" allows an understanding of the ratio of ester bonds in lactone rings in the sample (i.e., low-toxicity SL-containing composition). The ester value (mg KOH/g) correlates to the proportion of lactonic SL, relative to the total amount (100 mass %) of SLs contained in the SL-containing composition. The proportion of lactonic SL relative to the ethanol-soluble content (100 mass %) can be calculated from the ester value.

The ethanol-soluble content substantially corresponds to the total amount of acidic SL, lactonic SL, fatty acid, and hydroxy fatty acid contained in the SL-containing composition. Accordingly, the proportion of acidic SL, based on the total amount of the acidic SL, lactonic SL, fatty acid, and hydroxy fatty acid in the composition taken as 100 mass %, can be calculated by obtaining the ester value.

The "ester value (mg KOH/g)" can be measured in accordance with The JOCS Standard Methods for the Analysis of Fats, Oils and Related Materials (2.3.3-1996) defined by the Japan Oil Chemists' Society (Japan). The details are as explained in Test Example 1. The low-toxicity SL-containing composition of the present invention has an ester value (mg KOH/g) of typically 0 to 2 mg KOH/g. From the viewpoint of low toxicity, the ester value is preferably 0 to 1.5 mg KOH/g, more preferably 0.01 to 0.9 mg KOH/g, and particularly preferably 0 to 0.45 mg KOH/g. In order to achieve low toxicity while maintaining good performance as a surfactant (wettability, solubilization power, detergency, and foamability), the ester value is preferably more than 0 (for example, 0.01 mg KOH/g) but not more than 2 mg KOH/g, more preferably 0.1 to 2 mg KOH/g, even more preferably 0.1 to 1.5 mg KOH/g, and particularly preferably 0.8 to 1.5 mg KOH/g.

When the total amount of acidic SL and lactonic SL contained in the low-toxicity SL-containing composition is defined as 100 mass %, the proportion of acidic SL to lactonic SL (weight ratio of acidic SL to lactonic SL) is in the range of 98:2 to 100:0, preferably 98.5:1.5 to 100:0, and more preferably 99:1 to 100:0. When a yeast that produces lactonic SL is used as the SL-producing yeast, acidic SL may not account for 100 mass %. In this case, the proportion (weight ratio) of acidic SL to lactonic SL may be 99.99:0.01.

(a) (3) The Total Proportion of the Fatty Acid and Hydroxy Fatty Acid is 0.01 to 4 Mass % in Terms of Dry Weight.

This is the proportion of fatty acid and hydroxy fatty acid (in terms of dry weight), relative to the total amount (100 mass %) of the acidic SL, lactonic SL, fatty acid, and hydroxy fatty acid in the low-toxicity SL-containing composition. This corresponds to the proportion of fatty acid and hydroxy fatty acid contained in the ethanol-soluble content (100 mass % of) the low-toxicity SL-containing composition. Accordingly, the proportion of fatty acid and hydroxy fatty acid in the ethanol-soluble content (100 mass %) of the low-toxicity SL-containing composition can be said to be 0.01 to 4 mass %.

The fatty acid referred to herein is a fatty acid contained in a medium used in culturing an SL-producing yeast. The fatty acid is calculated as an ether extract by the method for measuring the ether extract content explained in the Examples. Specifically, the fatty acid is a saturated or unsaturated fatty acid having 6 to 24 carbon atoms. Specific examples of such fatty acids include caproic acid (C6), enanthic acid (C7), caprylic acid (C8), pelargonic acid (C9), capric acid (C10), lauric acid (C12), myristic acid (C14), pentadecyl acid (C15), palmitic acid (C16), margaric acid (C17), stearic acid (C18), arachidic acid (C20), docosanoic acid (C22), lignoceric acid (C24), and like saturated fatty acids; and palmitoleic acid (C16:1), oleic acid (C18:1), linolic acid (C18:2), linolenic acid (C18:3), arachidonic acid (C20:4), eicosapentaenoic acid (C20:5), docosahexaenoic acid (C22:6), and like unsaturated fatty acid.

Examples of the hydroxy fatty acid referred to herein include fatty acids mentioned above wherein at least one hydrogen atom is replaced with a hydroxyl group.

The upper limit of the (total) proportion of the fatty acid and hydroxy fatty acid is preferably 2.4 mass % or less, more preferably 1.2 mass % or less, and particularly preferably 0.24 mass % or less. The lower limit of the proportion is preferably, for example, 0.01 mass %. Although the amount of fatty acid and hydroxy fatty acid is preferably as low as possible in terms of obtaining an SL-containing composition having low toxicity, containing fatty acid and hydroxy fatty acid to some extent in the range of 0.01 to 4 mass % is advantageous in terms of maintaining the surfactant potency of acidic SL. Without being bound by a particular theory, one reason for achieving this advantage may be that fatty acid and hydroxy fatty acid exhibit a kind of chelate effect in test sample. Specifically, due to the chelate effect of fatty acid and hydroxy fatty acid, metal ions of K, Na, Ca, Mg, etc. contained in a test sample are captured, so that acidic SL is inhibited from forming salts with metal ions and can maintain their effects as a surfactant. The low-toxicity SL-containing composition of the present invention includes low-toxicity SL-containing compositions (Examples 1 to 10) containing fatty acids and hydroxy fatty acids in a total proportion of 0.1 to 4 mass %. However, these are merely embodiments of the present invention. The present invention is not limited to these embodiments.

Saturated and unsaturated fatty acids having 16 and 18 carbon atoms are predominant among the fatty acids and hydroxy fatty acids contained in the low-toxicity SL-containing composition of the present invention. Specifically, main fatty acids contained in the low-toxicity SL-containing composition are saturated fatty acids having 16 carbon atoms, and unsaturated fatty acids having 18 carbon atoms and containing one or two double bonds. Main hydroxy fatty acids contained in the low-toxicity SL-containing composition are saturated fatty acids having 16 carbon atoms, and unsaturated fatty acids having 18 carbon atoms and containing one or two double bonds (see Test Example 1 and Table 2). Therefore, the (total) proportion of the fatty acids and hydroxy fatty acids can also be said to be substantially the proportion of (the total amount of) $C_{16}$ and $C_{18}$ fatty acids and hydroxy fatty acids.

The proportion of the fatty acid and hydroxy fatty acid can be determined from the ether extract content (%) of the low-toxicity SL-containing composition.

Specifically, the "ether extract content (%)" as used herein refers to the proportion (mass %) of the substances extracted from a sample (low-toxicity SL-containing composition) in an amount corresponding to 1 g of its ethanol-soluble content using ether. This allows an understanding of the proportion of fatty acid and hydroxy fatty acid contained in the sample (low-toxicity SL-containing composition). That is, since the "ether extract content (%)" correlates to the proportion of fatty acid and hydroxy fatty acid in the ethanol-soluble content (100 mass %), the proportion of fatty acid and hydroxy fatty acid in the ethanol-soluble content (100 mass %) can be calculated from the "ether extract content (%)." As described above, since the ethanol-soluble content substantially corresponds to the total amount of the acidic SL, lactonic SL, fatty acid, and hydroxy fatty acid contained in the SL-containing composition, the amount of fatty acid and hydroxy fatty acid relative to the total amount (100 mass %) of the acidic SL, lactonic SL, fatty acid, and hydroxy fatty acid can be calculated by obtaining the "ether extract content (%)."

The details of the method for measuring the "ether extract content (%)" are as explained in Test Example 1. The "ether extract content (%)" of the low-toxicity SL-containing composition of the present invention is typically 0.01 to 4 mass %, preferably 0.01 to 2.4 mass %, more preferably 0.01 to 1.2 mass %, and particularly preferably 0.01 to 0.24 mass %. In particular, the ether extract content (%) may be, for example, in the range of 0.1 to 4 mass %.

(b-1) The Proportion of the Lactonic SL is 0 to 2.12 Parts by Mass, Relative to 100 Parts by Mass of the Acidic SL Contained in the Low-Toxicity SL-Containing Composition.

This proportion can be easily calculated from the acidic SL content and lactic SL content of the low-toxicity SL-containing composition. The proportion is preferably 0.01 to 1.5 parts by mass, and more preferably 0.01 to 1.0 parts by mass.

(b-2) The Proportion of (the total amount) of the Fatty Acid and Hydroxy Fatty Acid is 0.01 to 4.25 Parts by Mass, Relative to 100 Parts by Mass of the Acidic SL Contained in the Low-Toxicity SL-Containing Composition.

This proportion can be easily calculated from the acidic SL content, fatty acid content, and hydroxy fatty acid content of the low-toxicity SL-containing composition. The proportion of (the total amount) of the fatty acid and hydroxy fatty acid is preferably 0.05 to 2.5 parts by mass, and more preferably 0.1 to 1.0 parts by mass.

(c) Neither the Acidic SL nor the Lactonic SL Contained in the Low-toxicity SL-containing Composition has an Acetyl Group.

SLs containing acetyl groups have higher cytotoxicity than SLs not containing acetyl groups. Acetyl groups of SLs are thus considered to be involved in the cytotoxicity of both of the acidic SL and lactonic SL. In contrast, the low-toxicity SL-containing composition of the present invention has a feature such that neither the acidic SL nor the lactonic SL contained in the composition has an acetyl group.

The proportion of the acetyl groups contained in the SL-containing composition can be calculated from the hydroxyl value of the SL-containing composition in an amount corresponding to 1 g of its ethanol soluble content. The low-toxicity SL-containing composition of the present invention does not contain acetyl groups. Accordingly, the hydroxyl value may be any value that reflects the absence of acetyl groups. The theoretical hydroxyl value of the low-toxicity SL-containing composition (corresponding to 7 hydroxyl groups) is 630 mgKOH/L. In view of reaction efficiency (about 90%), the low-toxicity SL-containing composition may actually have a hydroxyl value of, for example, 545 to 630 mgKOH/L. That is, when the SL-containing composition in an amount corresponding to 1 g of its ethanol soluble content has a hydroxyl value of 545 to 630 mgKOH/g, SLs contained in the SL-containing composition can be determined to have no acetyl groups.

The "hydroxyl value (mg KOH/g)" as used herein refers to the amount (mg) of potassium hydroxide required for complete acetylation of OH groups of the compounds contained in a sample (low-toxicity SL-containing composition) in an amount corresponding to 1 g of its ethanol-soluble content. This allows for measurement of the proportion of free hydroxyl group in the SLs contained in the sample (low-toxicity SL-containing composition). A high hydroxyl value (mg KOH/g) means a high proportion of free hydroxyl groups in the SLs (that is, a small number of hydroxyl groups are acetylated=a small amount of acetyl groups). A low hydroxyl value (mg KOH/g) means a low proportion of free hydroxyl groups in the SLs (that is, a large number of hydroxyl groups are acetylated=a large amount of acetyl groups).

The "hydroxyl value (mg KOH/g)" can be measured according to The JOCS Standard Methods for the Analysis of Fats, Oils and Related Materials (2.3.6.2-1996) defined by the Japan Oil Chemists' Society (Japan). The details are as explained in Test Example 1. The "hydroxyl value (mg KOH/g)" of the low-toxicity SL-containing composition of the present invention is preferably such that the composition in an amount corresponding to 1 g of its ethanol-soluble content has a hydroxyl value of 545 to 630 mg KOH/g, as described above. More preferably, the hydroxyl value is 560 to 630 mg KOH/g, and even more preferably 575 to 630 mg KOH/g. The low-toxicity SL-containing composition of the present invention includes low-toxicity SL-containing compositions having a hydroxyl value of 575 to 585 mg KOH/g (Examples 1 to 10). These are merely embodiments of the present invention. The present invention is not limited to these embodiments. The low-toxicity SL-containing composition of the present invention includes those having at least one of the following features (d) to (h), in addition to the above features (a) (1) to (3), (b), and (c).

(d) An Aqueous Solution Prepared by Dissolving the Low-toxicity SL-Containing Composition so that the Solution has an Ethanol-soluble Content of 10 Mass % has an Absorbance ($OD_{440}$) of 0.001 to 1.

The low-toxicity SL-containing composition according to the present invention includes compositions having a color other than white.

Acidic SL, lactonic SL, fatty acid, and hydroxy fatty acid are colorless or white. Therefore, coloring of the low-toxicity SL-containing composition means that the composition contains a coloring component in addition to acidic SL, lactonic SL, fatty acid, and hydroxy fatty acid. The coloring component is not particularly limited as long as it is derived from an SL-producing yeast culture. Examples of the coloring component include, but are not limited to, melanoidin.

The degree of coloring of the low-toxicity SL-containing composition of the present invention can be evaluated by dissolving the low-toxicity SL-containing composition in an alkali solution (2% $Na_2CO_3$ in 0.1N NaOH) to prepare an aqueous solution having a total concentration of ethanol-soluble components of 10 mass %, and measuring the absorbance of the aqueous solution at a wavelength of 440 nm (hue: $OD_{440}$). When the low-toxicity SL-containing composition of the present invention is prepared in the above manner, the aqueous solution has a hue ($OD_{440}$) of 0.001 to 1, preferably 0.005 to 0.8, more preferably 0.01 to 0.6, and particularly preferably 0.01 to 0.5. The low-toxicity SL-containing composition of the present invention includes low-toxicity SL-containing compositions having a hue ($OD_{440}$) of 0.1 to 0.4 (Examples 1 to 7). However, these are merely embodiments of the present invention. The present invention is not limited to these examples.

(e) Evaporation Residue: 1 to 100%

As explained in Test Example 1, the term "evaporation residue (%)" refers to the amount of the residue obtained by evaporation of a sample, and is expressed in mass percentage (mass %). The evaporation residue allows an understanding of the content of coexisting substances, particularly coexisting substances having a high boiling point, in a sample, i.e., a low-toxicity SL-containing composition in the present invention. The "evaporation residue (%)" can be measured in accordance with the Second Method of JIS K0067-1992. The details are as described in Test Example 1. The evaporation residue (%) of the low-toxicity SL-containing composition of the present invention may be in the range of 1 to 100%, preferably 5 to 100%, and more preferably 10 to 100%. Further preferably, the evaporation residue is 60 to 100%, more preferably 70 to 100%, particularly preferably 80 to 100%, and more particularly preferably 90 to 100%.

(f) Loss on Drying: 0 to 99%

As will be explained in Test Example 1, the term "loss on drying (%)" refers to the amount of loss obtained by drying a sample, which is expressed in mass percentage (mass %). The loss on drying allows an understanding of the content of water and other volatile substances (low-boiling-point compounds) in a sample i.e., a low-toxicity SL-containing composition in the present invention. The loss on drying (%) can be measured in accordance with the First Method of JIS K0067-1992. The details are as described in Test Example 1. The loss on drying (%) of the low-toxicity SL-containing composition of the present invention is in the range of 0 to 99%, preferably 0 to 95%, and more preferably 0 to 90%. Further preferably, the loss on drying is 0 to 30%, more preferably 0 to 20%, particularly preferably 0 to 20%, and more particularly preferably 0 to 10%.

(g) Ethanol Soluble Content: 1 to 100%

As will be explained in Test Example 1, the term "ethanol-soluble content (%)" refers to the amount (mass %) of ethanol-soluble substances contained in a sample. The ethanol-soluble content (%) allows an understanding of the content of ethanol-soluble polar substances, such as surfactants, in a sample. The "ethanol-soluble content (%)" can be measured in accordance with JIS K3362-2008. The details are as described in Test Example 1. The ethanol-soluble content (%) of the low-toxicity SL-containing composition of the present invention may be in the range of 1 to 100%, preferably 5 to 100%, and more preferably 10 to 100%. The ethanol-soluble content (%) is even more preferably 85 to 100%, still even more preferably 90 to 100%, particularly preferably 95 to 100%, and more particularly preferably 98 to 100%. The ethanol-soluble content (%) refers to the proportion (mass %) of the acidic SL, lactonic SL, fatty acid, and hydroxy fatty acid contained in a target sample, i.e., a low-toxicity SL-containing composition in the present invention, when the amount of the composition is defined as 100 mass %.

(h) Infrared Absorption Spectrum

More preferably, the low-toxicity SL-containing composition of the present invention has an infrared absorption spectrum comprising infrared absorption bands (absorption peaks) at least at wavenumbers of around 1024 $cm^{-1}$, around 1706 to 1730 $cm^{-1}$, around 2854 $cm^{-1}$, around 2924 $cm^{-1}$, and around 3000 to 3500 $cm^{-1}$.

The form of the low-toxicity SL-containing composition of the present invention is not particularly limited. The low-toxicity SL-containing composition of the present invention may be in the form of a liquid, emulsion, or solid. Solid forms are preferable. Examples of solid forms include tablets, pills, powders, granules, and capsules. Powder or granule forms are preferable, and powder forms are more preferable.

A feature of the low-toxicity SL-containing composition of the present invention is that as a result of selectively removing cytotoxic components among the by-products of fermentation with an SL-producing yeast, which are generated during the production process, the composition contains a less amount of cytotoxic components, while maintaining surfactant effects. Examples of cytotoxic components include, but are not limited to, lactonic SL; fatty acids and hydroxy fatty acids having 16 or 18 carbon atoms; acetyl-containing SLs; and the like.

The toxicity of the low-toxicity SL-containing composition of the present invention can be evaluated, for example, by the cell lethal concentration ($IC_{50}$) calculated by a cytotoxic test using HeLa cells (human cervical epitheloid carcinoma cells). However, to evaluate the effects of the low-toxicity SL-containing composition from the aspects of both surfactant effects and cytotoxicity effects, it is preferable to calculate the value ($IC_{50}$/CMC) obtained by dividing the "cell lethal concentration ($IC_{50}$)" of the low-toxicity SL-containing composition by the "critical micelle concentration (CMC)" of the low-toxicity SL-containing composition.

The cytotoxicity test using HeLa cells and the method for calculating the cell lethal concentration ($IC_{50}$) are as described in detail in Test Examples 3. The method for measuring the critical micelle concentration (CMC) is as described in detail in Test Example 2.

The HeLa cell lethal concentration ($IC_{50}$) of the low-toxicity SL-containing composition of the present invention may be, for example, 2,000 to 60,000 ppm, preferably 3,000 to 60,000 ppm, more preferably 5,000 to 60,000 ppm, and particularly preferably 10,000 to 60,000 ppm.

The critical micelle concentration (CMC) of the low-toxicity SL-containing composition of the present invention may be, for example, 50 to 500 ppm, preferably 50 to 400 ppm, more preferably 50 to 300 ppm, and particularly preferably 100 to 300 ppm.

The "$IC_{50}$/CMC" of the low-toxicity SL-containing composition of the present invention calculated from the cell lethal concentration ($IC_{50}$) and critical micelle concentration (CMC) is in the range of 6.7 to 200, preferably 10 to 200, more preferably 17 to 200, and particularly preferably 33 to 200. The low-toxicity SL-containing composition of the present invention includes low-toxicity SL-containing compositions having an "$IC_{50}$/CMC" of 106.7 to 200 (Examples 1 to 10). However, these are merely embodiments of the present invention. The present invention is not limited to these embodiments.

As will be explained in Test Example 3, the low-toxicity SL-containing composition of the present invention has extremely low irritation to the eyes and mucosa, as shown in the cell lethal concentration ($IC_{50}$), and is less toxic and less irritating (non-irritating) to the eyes and mucosa. The mucosa as referred to herein includes mucosa other than ocular mucosa. Specific examples of such mucosa include oral mucosa, throat mucosa, nasal cavity mucosa, aural cavity mucosa, genital mucosa, anal mucosa, and the like.

(III) Use of the Low-toxicity SL-containing Composition

As explained above, the low-toxicity SL-containing composition of the present invention has surfactant effects, more specifically, has high cleaning power and good foaming, as well as extremely low cytotoxicity and low eye and mucosa irritation, and can be said to be substantially non-toxic and non-irritating at practical concentrations. Accordingly, the low-toxicity SL-containing composition of the present invention can be used as a low-toxicity, low-irritation anionic surfactant. Further, the low-toxicity SL-containing composition of the present invention can also be used in products that require high safety and low irritation (no irritation), such as foods or beverages, drugs, quasi-drugs, medical devices, fragrances or cosmetics, and household supply items. It is also possible to use the low-toxicity SL-containing composition of the present invention as an additive for foods or beverages, drugs, quasi-drugs, medical devices, fragrances or cosmetics, or household supply items.

"Foods or beverages" or "food or beverage" as used herein includes, in addition to general food products and beverages, food and beverages that have specific functions and are ingested to, e.g., maintain health, such as health supplements, health functional foods, foods for specified health use, and supplements. "Fragrances or cosmetics" or "fragrance or cosmetic" as used herein refers to concepts including aroma products, such as scented water, cologne, and perfume; cosmetics; and quasi-drugs. Cosmetics are those applied to the body through application and rubbing, spraying, or other similar methods (e.g., pasting) for the purpose of cleaning, beautifying, and increasing the attractiveness of a person's body to change one's physical appearance, or maintaining the health of the skin or hair. Examples of cosmetics include make-up cosmetics (foundation, lipstick, etc.), basic cosmetics (face lotion, milky lotion, etc.), hair-care products (hair tonic, hair lotion, hair cream, etc.), body cosmetics (such as body lotions, hand creams, and sunscreen formulations), and toiletry products (toothpaste, shampoo, hair rinse, soap, body wash, facial wash, bath fragrance, eye wash, etc.), quasi-drugs (e.g., medicated cosmetics, antiperspirants, hair color products, and insecticides), aroma products (perfume, eau de toilette, eau de cologne, body powder, scent bags, etc.), and the like. Examples of drugs include medications for external application (skin drugs for external application, eye drops, cavity drugs, nasal sprays, ear drops, suppositories, etc.), oral medicines, injections, and the like. Examples of medical devices include wound dressings and the like. Examples of household supply items include dishwashing detergents, vegetable washes, laundry detergents, softeners, bleaches, household cleansers, bathroom cleansers, toilet bowl cleansers, aromatics, and the like.

Examples of regenerative medical products include the following:
(1) products obtained by subjecting human or animal cells to culturing or like processing, which are used:
(a) to reconstruct, repair, or form structures or functions in the body, or
(b) to treat or prevent diseases, and
(2) products used by being introduced into human cells for gene therapy.

The low-toxicity SL-containing composition of the present invention is particularly suitable for use as an external composition for which low irritation (or no irritation) is required. Specific examples of such external compositions include fragrances and cosmetics for hypersensitive skin (cosmetics and aroma products); external drugs or external quasi-drugs for application to the skin with a wound or inflammation; cosmetics (such as wound cleansers); medical devices (such as wound dressings); cosmetics, drugs or quasi-drugs (e.g., eye drops, ophthalmic ointments, eye lotions, nasal washes, contact lens fitting liquids, and like eye-care products; nasal washes, nasal sprays, stomatitis therapeutic agents) for application to the eyes, nasal cavity, or oral cavity. The form of the wound dressings, cell cultures, and regenerative medical products are not particularly limited and may be in the form of gels, powders, sheets, or other various forms.

When the low-toxicity SL-containing composition of the present invention is used as an anionic surfactant, the low-toxicity SL-containing composition itself can be used as an anionic surfactant. Alternatively, the low-toxicity SL-containing composition may further contain other components as long as the feature of the present invention, i.e., achieving low toxicity and/or low irritation while providing surfactant effects, is not impaired. Examples of such other components include, but are not limited to, solvents such as distilled water, ion-exchanged water, and ethanol; additives such as sodium chloride and potassium chloride; solubilizing agents such as glycerol, propylene glycol, and hexylene glycol; and thickeners such as xanthan gum, alginic acid, and dextran; pH adjusting agents such as hydrochloric acid, sulfuric acid, boric acid, sodium hydroxide, and potassium hydroxide; chelating agents such as phosphoric acid compounds, nitrilotriacetic acid (NTA), and ethylenediaminetetraacetic acid (EDTA); and other components such as pigments and enzymes. When other components are incorporated, the amount of the low-toxicity SL-containing composition of the present invention contained in the anionic surfactant is not particularly limited, as long as the surfactant effects are provided. The anionic surfactant preferably contains the low-toxicity SL-containing composition in an amount of 0.005 to 99.9 mass %, preferably 0.01 to 50 mass %, more preferably 0.02 to 10 mass %, and particularly preferably 0.1 to 5 mass %, in terms of the amount of acidic SL.

When the low-toxicity SL-containing composition of the present invention is used as an additive of foods or beverages, drugs, quasi-drugs, medical devices, fragrances or cosmetics, or household supply items (food additives, drug additives, quasi-drug additives, medical device additives, fragrance or cosmetic additives, or household supply item additives), the low-toxicity SL-containing composition itself may be used as an additive for these products. Alternatively, the low-toxicity SL-containing composition may further contain other components as long as they do not impair the feature of the present invention, i.e., providing the desired surfactant effects while achieving low toxicity and/or low irritation. Such other components can be suitably selected according to the desired products, such as foods or beverages, drugs, quasi-drugs, medical devices, fragrances or cosmetics, or household supply items. When other components are incorporated, the amount of the low-toxicity SL-containing composition of the present invention contained in the additive is not particularly limited, as long as the desired surfactant effects are provided. The additive may contain the low-toxicity SL-containing composition of the present invention, for example, in an amount of 0.005 to 99.9 mass %, preferably 0.01 to 50 mass %, more preferably 0.02 to 10 mass %, and particularly preferably 0.1 to 5 mass %, in terms of the amount of deacetylated acidic SL.

When the low-toxicity SL-containing composition of the present invention is added to foods or beverages, drugs, quasi-drugs, medical devices, fragrances or cosmetics, or household supply items, that is, when foods or beverages, drugs, quasi-drugs, medical devices, fragrances or cosmetics, or household supply items are produced by using the low-toxicity SL-containing composition of the present invention, the amount of the low-toxicity SL-containing composition in these various products can be suitably selected according to the purpose and properties of each product, within the range that the desired surfactant effects are provided. Although the amount of the low-toxicity SL-containing composition of the present invention to be added to foods or beverages, drugs, quasi-drugs, medical devices, fragrances or cosmetics, or household supply items is not limited, the low-toxicity SL-containing composition may be added in an amount such that the resulting foods or beverages or other products mentioned above have a CMC of 300 ppm or more. For example, such foods or beverages or other products may contain the low-toxicity SL-containing composition in an amount of 0.005 to 99.9 mass %, preferably 0.01 to 50 mass %, more preferably 0.02 to 10 mass %, and particularly preferably 0.1 to 5 mass %, in terms of the amount of acidic SLs.

Specifically, the low-toxicity SL-containing composition of the present invention may be contained, for example, in the following proportions according to the product.

Body wash: 0.01 to 100 mass %, preferably 1 to 90 mass %, and more preferably 5 to 800 mass %.
Hair wash: 0.01 to 30 mass %, preferably 1 to 25 mass %, and more preferably 5 to 20 mass %.
Eye wash: 0.001 to 10 mass %, preferably 0.01 to 8 mass %, and more preferably 0.05 to 5 mass %.
Eye drop: 0.001 to 10 mass %, preferably 0.01 to 8 mass %, and more preferably 0.05 to 5 mass %.
Cosmetic: 0.01 to 20 mass %, preferably 0.05 to 15 mass %, more preferably 0.1 to 10 mass %.
Oral-cavity wash: 0.001 to 10 mass %, preferably 0.05 to 8 mass %, more preferably 0.1 to 5 mass %.
Mucosa or wound cleanser: 0.001 to 30 mass %, preferably 0.01 to 25 mass %, and more preferably 0.1 to 20 mass %.
Wound dressing: 0.001 to 30 mass %, preferably 0.005 to 25 mass %, more preferably 0.01 to 20 mass %.

When the low-toxicity SL-containing composition of the present invention is used by being incorporated into drugs, quasi-drugs, fragrances or cosmetics, or household supply items, such medical products or the like may also contain whitening agents, anti-aging agents, moisturizers, ultraviolet absorbers, antimicrobial agents, and/or other components.

Examples of whitening agents include L-ascorbic acid or derivatives, tranexamic acid or derivatives thereof, hydroquinone and derivatives thereof, rcinol, edetic acid or derivatives, arbutin, placenta extract, t-AMCHA, acerola extract, rose fruit extract, ellagic acid or derivatives, hot extract, chamomile extract, chamomile flower extract, kiwi extract, glutathione, tocotrienol, ferulic acid, raspberry ketone, rucinol, uva ursi extract, pyridoxine dipalmitate, sulfur, kojic acid or derivatives thereof, glucosamine or derivatives thereof, hydroxycinnamic acid or derivatives thereof, glutathione, arnica extract, *Scutellaria* root extract, mulberry bark extract, *Bupleurum falcatum* extract, *Saposhnikovia divaricata* extract, *ganoderma lucidum* culture or extracts thereof, linden extract, peach leaf extract, rose fruit extract, *Sophora* root extract, *Sanguisorba officinalis* root extract, *Angelicae radix* extract, coix seed extract, persimmon leaf extract, *Rheum palmatum* extract, moutan cortex extract, hamamelis extract, horse chestnut extract, hypericum extract, oil-soluble glycyrrhiza extract, and the like.

Examples of anti-inflammatory agents include glycyrrhizic acid or salts thereof, glycyrrhetinic acid or salts thereof, isopropyl aminocaproic acid or salts thereof, allantoin, lysozyme chloride, guaiazulene, methyl salicylate, γ-oryzanol, and the like.

Examples of antioxidants include carotinoids such as α-carotene, β-carotene, γ-carotene, lycopene, cryptoxanthin, lutein, zeaxanthin, isozeaxanthin, rhodoxanthin, capsanthin, and crocetin; 1,4-diazacyclooctane, 2,5-dimethylfuran, 2-methylfuran, 2,5-diphenylfuran, 1,3-diphenylisobenzofuran, α-tocopherol, β-tocopherol, γ-tocopherol, d-tocopherol, histidine, tryptophan, methionine, alanine or alkyl esters thereof, dibutylhydroxytoluene, butylhydroxyanisole, ascorbic acid; tannins such as tannic acid, epicatechin, epicarocatechin, epicatechin gallate, and epicarocatechin gallate; flavonoids such as rutin; other propyl gallates, *Siraitia grosvenorii* extract, astaxanthin, tocopherol, ascorbic acid derivatives, edetate tetrasodium, erythorbic acid, tocopherol acetate, retinol acetate, dibutylhydroxytoluene, ascorbyl stearate, ascorbyl palmitate, a mixture of methylsilanol dioleoyl tocopherol and silicic acid anhydride, benzyl nicotinate, photosensitive element 401, aspartic acid, disodium adenosine triphosphate, aminobutyric acid, fennel extract, *nasturtium officinale* extract, caffeine, chlorella extract, saffron crocus extract, zingiber officinale root extract, soy extract, jujube extract, folic acid, retinol, retinol palmitate, inositol, turmeric extract, oryzanol, carotene, carrot extract, wheat germ extract, *Cnidium officinale* extract, *Citrus unshiu* peel extract, angelicae radix extract, angelicae radix root extract, *houttuynia cordata* extract, tocopherol, tocopherol nicotinate, peony extract, ergocalciferol, pyridoxine dicaprylate, batyl alcohol, glycyrrhetinyl stearate, glycyrrhizic acid, glycyrrhetinic acid, diphenhydramine hydrochloride, lysozyme chloride, aminocaproic acid, reishi mushroom extract, coix seed extract, melilot extract, *Angelicae radix* extract, *Paeonia suffruticosa* extract, dong quai extract, dong quai root extract, *cnidium rhizome* extract, geranium herb extract, allantoin, arnica extract, arnica flower extract, *Scutellaria* root extract, Coptis rhizome extract, *Hypericum erectum* extract, cattail extract, *Chamomilla recutita* extract, calamine, *Artemisia capillaris* extract, liquorice extract, guaiazulene, gardenia extract, *Sasa veitchii* extract, dipotassium glycyrrhizinate, stearyl glycyrrhetinate, Gentiana lutea extract, black tea extract, comfrey extract, comfrey leaf extract, tocopherol acetate, methyl salicylate, zinc oxide, *lithospermi radix* extract, *Lithospermum* root extract, perilla extract, perilla leaf extract, *Filipendula* extract, peony extract, honeysuckle extract, sage extract, English ivy extract, *Sambucus nigra* extract, *Achillea millefolium* extract, *Swertia japonica* extract, mulberry root bark extract, *Calendula officinalis* extract, pyridoxine hydrochloride, *Eriobotrya japonica* leaf extract, *Tilia cordata* extract, peach leaf-fruit extract, *Centaurea cyanus* extract, saxifrage extract, wormwood extract, lettuce extract, Roman chamomile extract, burnet extract, cacalol, polyamine, and the like.

Examples of moisturizers include sodium pyridon carboxylate, glycol, glycerol, glucose, maltose, maltitol, sucrose, fructose, xylitol, sorbitol, maltotriose, threitol, erythritol, amylolysis sugar reduced alcohol, sorbitol, polyhydric alcohols (ethylene glycol, 1,4-butylene glycol, glycerin, triglycerin, tetraglycerin, 1,3-butylene glycol, propylene glycol, dipropylene glycol, polyethylene glycol, 1,3-propanediol, pentylene glycol, hexanediol, octanediol), serine, glycine, threonine, alanine, collagen, hydrolysis collagen, vitronectin, fibronectin, keratin, elastin, royal jelly, chondroitin sulfate, heparin, glycerophospholipid, glyceroglycolipid, sphingophospholipid, sphingoglycolipid, linoleic acid or esters thereof, eicosapentaenoic acid or esters thereof, pectin, bifidobacteria ferments, lactic ferments, yeast extracts, *Ganoderma lucidum mycelium* culture or extracts thereof, wheat germ oil, avocado oil, rice germ oil, lojoba oil, soybean phospholipid, γ-orizanol, *Althaea officinalis* extract, coix seed extract, *rehmanniae radix* extract, jujube extract, sea weed extract, *Aloe arborescens* extract, burdock extract, *Rosmarinus officinalis L.* extract, arnica extract, wheat bran, pyrrolidone carboxylic acid, tomato extract, camellia oil, soybean phospholipid, hyaluronic acid, threonine, ammonium glycolate, methylsilanol alginate, coicis semen, *angelica acutiloba* extract, *angelica acutiloba* root extract, soybean extract, asparagus extract, sodium DNA, sodium PCA, sodium RNA, *Angelica keiskei* extract, aspartic acid, sweet hydrangea leaf extract, *Siraitia grosvenorii* extract, lactoferrin, alanine, arginine, sodium alginate, althea extract, aloe vera extract, oyster extract, barley malt extract, persimmon leaf extract, hydrolyzed keratin, hydrolyzed collagen, hydrolyzed conchiolin, hydrolyzed eggshell membrane, hydrolyzed egg white, hydrolyzed silk, hydrolyzed soybean protein, brown algae extract, Chinese quince extract, raspberry extract, xylitol, chitosan, cucumber extract, cucumber fruit extract, guava leaf extract, guava fruit extract, quince seed extract, glycine, glycerol, glucose, grapefruit extract, grapefruit fruit extract, clematis extract, burdock extract, rice ferment, chondroitin sodium sulfate, fish collagen, Crataegus extract, *shiitake* mushroom extract, *rehmanniae radix* extract, glycerol, cystine, cysteine, *Equisetum arvense* extract, mallow extract, serine, sorbitol, soybean protein, tomato extract, sodium lactate, lactic acid bacilli, fermented soybean extract, urea, Rosa canina fruit extract, almond extract, almond fruit extract, corn oil, honey, sodium hyaluronate, betaine, loofah extract, maltitol, maltose, mannitol, lily extract, lysine, apple extract, Chinese milk vetch extract, royal jelly, lanolin fatty acid polyethylene glycol 1000, isopropyl lanolate, isopropyl myristate, isobutyl myristate, hexyldecanol, myristyl lactate, lanolin fatty acid, caprylic triglyceride, oleyl alcohol, octyldodecyl oleate, decyl oleate, reduced lanolin, octyldodecanol, almond oil, avocado oil, olive oil, oleic acid, orange roughy oil, cacao butter, carrot extract, sesame oil, sasanqua oil, safflower oil, dihydrocholesterol, squalane, cholesteryl stearate, Ceramide 2, evening primrose oil, castor oil, sunflower oil, sunflower seed oil, hybrid sunflower oil, phytosphingosine, grape seed oil, jojoba oil, jojoba seed oil, mineral oil, mink oil, macadamia nut oil, meadowfoam oil, eucalyptus leaf oil, lanolin, linoleic acid, rosehip oil, Vaseline, and polyglutamic acid.

Examples of usable ultraviolet absorbers include amyl benzoate, octyl p-aminobenzoate, ethylene glycol salicylate, phenyl salicylate, octyl salicylate, benzyl salicylate, butylphenyl salicylate, homomenthyl salicylate, benzyl cinnamate, 2-ethoxyethyl p-methoxycinnamate, octyl p-methoxycinnamate, glyceryl ester of mono-2-ethylhexanoic acid and di-p-methoxycinnomic acid, isopropyl p-methoxycinnamate, 2-etyylhexyl-p-methoxycinnamate, urocanic acid, ethyl urocanate, hydroxymethoxy benzophenone, hydroxymethoxybenzophenone sulfonic acid or salts thereof, dihydroxymethoxybenzophenone, sodium dihydroxymethoxybenzophenone disulfate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, 2-(2-hydroxy-5-methylphenyl) benzotriazole, 2-ethylhexyl p-dimethylaminobenzoate, ethyl p-aminobenzoate, t-butyl methoxydibenzoylmethane, oxybenzone-1, ethyl guaiazulene sulfonate, cinoxate, anthranilic acid UV-absorbers (such as homomenthyl-N-acetylanthranilate), ethylhexyl dimethoxybenzylidene dioxoimidazolidine propionate, and the like. Examples of UV scattering agents include titanium oxide, zinc oxide, and the like.

Examples of antimicrobial agents include phellodendron bark extract, halocarvan, chlorphenesin, lysozyme chloride, alkyldiaminoethylglycine hydrochloride, isopropylmethyl phenol, thymol, hexachlorophene, berberine, tioxolone, salicylic acid, or derivatives of these compounds, benzoic acid, sodium benzoate, p-oxybenzoic acid ester, p-chloro-m-cresol, benzalkonium chloride, phenoxyethanol, isopropylmethyl phenol, carbolic acid, sorbic acid, potassium sorbate, hexachlorophene, chlorhexidine chloride, trichlorocarbanilide, photosensitive elements, bis(2-pyridylthio-1-oxide) zinc, thianthol, hinokitiol, triclosan, trichlorohydroxydiphenyl ether, chlorhexidine gluconate, phenoxyethanol, resorcin, azulene, salicylic acid, zinc pyrithione, mononitroguaiacol sodium, fennel extract, zanthoxylum extract, cetylpyridinium chloride, benzethonium chloride, and undecylenic acid derivatives.

As shown in the Test Examples below, the low-toxicity SL-containing composition of the present invention itself has a moisturizes skin, ameliorates damage skin or hair (rough skin and hair cuticle damage), and protects skin and hair. Accordingly, the low-toxicity SL-containing composition of the present invention itself can be used as a moisturizer (for skin or hair), an agent ameliorating rough skin, a skin-protecting agent, and a hair-protecting agent, or the like. In this case, the proportion of the low-toxicity SL-containing composition of the present invention contained in each product (100 mass %) may be any amount that can produce effects according to the purpose of the product (such as whitening, amelioration of rough skin, or skin and hair protection). The proportion of the low-toxicity SL-containing composition of the present invention in each product can be typically selected as desired from the range of 0.01 to 10 mass %, in terms of the amount of deacetylated acidic SL.

(IV) Method for Producing the Low-toxicity SL-containing Composition (IV-1) Starting Material (SL-containing Culture or a Treated Product Thereof)

Examples of the SL-containing culture or treated product thereof, which is used as a starting material for producing the low-toxicity SL-containing composition, include a wide range of crudely purified products of SL-containing cultures and treated products thereof containing SL. Examples of SL-producing yeasts include known yeasts. For example, the *Candida (Starmerella) bombicola* mentioned above can be preferably used. *Candida (Starmerella) bombicola* has been deposited with ATCC, which is a bioresource bank, and is available therefrom (e.g., *Candida bombicola* ATCC22214). Other SL-producing yeasts that belong to the *Candida* genus and are known to produce (acidic and lactonic) SLs can also be used to produce the low-toxicity SL-containing composition of the present invention. Examples of such SL-producing yeasts include *Candida magnoliae, Candida gropengisseri, Candida apicola, Candida petrophilum, Candida bogoriensis, Candida batistae*, and the like. These yeasts may be strains provided from deposit institutions, or strains obtained by successive subculturing thereof. Among these, the SL produced by *Rhodotorula (Candida) bogoriensis* NRCC9862 is 13-[(2'-O-β-D-glucopyranosyl-β-D-glucopyranosyl)oxy]docosanoic acid 6',6''-diacetate, wherein a glycosidic bond is formed between sophorose and a hydroxyl group at the center of an alkyl group. Although this SL is different from SLs represented by the above General Formulae (1) and (2), it is the same from the standpoint of being formed of sophorose and a hydroxy fatty acid, and is included within the scope of the SLs of the present invention.

In the present invention, *Candida floricola* ZM-1502 strain (FERM P-21133) and *Candida floricola* NBRC10700T strain can be suitably used as SL-producing yeasts that selectively produce only acidic SL. Hereinafter, these SL-producing yeasts may also be referred to as "acidic SL-producing yeasts" in order to distinguish these SL-producing yeasts from SL-producing yeasts that produce both acidic SL and lactonic SL (lactonic/acidic SL-producing yeasts).

Alternatively, the acetyltransferase-deleted *Candida bombicola* disclosed in Non-patent Literature (NPL 2) can also be used. When using the acetyltransferase-deleted *Candida bombicola*, non-acetylated SLs can be produced by a single step.

A preferable method for culturing an SL-producing yeast is, for example, a method of culturing while simultaneously giving a high concentration of a sugar and a hydrophobic oily substrate. The culture method is not limited thereto, and a wide range of known methods can be used as long as they do not interfere with the effect of the present invention. The known method may be the method disclosed in JP2002-045195A (PTL 2) or the like. More specifically, a method of culturing an SL-producing yeast using glucose as a sugar and using a carbon source containing fatty acid and vegetable oil as a hydrophobic oily substrate can be used.

The medium composition is not particularly limited. The fatty acid moiety of SLs is known to depend on the fatty acid chain length and proportion of the hydrophobic substrate added as a medium component, and thus can be controlled to some extent. For example, oleic acid or a lipid containing oleic acid in a high proportion is suitable for use as the hydrophobic substrate. Examples include vegetable oils such as palm oil, rice bran oil, rapeseed oil, olive oil, and safflower oil, and animal oils such lard and beef fat. For the fermentative production of SLs with a stably high yield, a mixture of hydrophilic sugar and hydrophobic fat/oil is preferable as a carbon source. Glucose is frequently used as a hydrophilic substrate.

After the liquid components are separated and removed from the obtained culture broth using a known solid-liquid-separation method, such as centrifugal separation or decantation, the resulting solids are washed with water to obtain an SL-containing fraction (SL-containing culture). The SL-containing fraction (SL-containing culture) obtained by culturing a lactonic/acidic SL-producing yeast is a mixture of lactonic SL and acidic SL (a lactonic/acidic SL-containing composition). The content of the acidic SL in the total amount of SLs is less than 45 mass % (based on solids). In contrast, SLs contained in the SL-containing fraction (SL-containing culture) obtained by culturing an acidic SL-producing yeast are all acidic SLs.

The method for collecting the lactonic/acidic SL-containing composition (or acidic SL-containing composition) from the culture broth of the SL-producing yeast may be any known method as long as the method does not interfere with the effect of the present invention. Examples of usable methods include the method disclosed in JP2003-009896A (Patent Literature (PTL) 3) or the like. This method controls the solubility of SLs in water by adjusting the pH of the culture broth of the SL-producing yeast or the SL-containing fraction prepared therefrom. Specifically, for example, after the culture broth of the SL-producing yeast is adjusted to about pH 6 to 7 with an aqueous NaOH solution or the like to solubilize SLs, the resulting solution is centrifuged to collect a supernatant. Subsequently, an aqueous sulfuric acid solution or the like is added to adjust the supernatant to about pH 2 to 3 to insolubilize SLs. After this mixture is allowed to settle, the resulting mixture is decanted to obtain a lactonic/acidic SL-containing composition (or an acidic SL-containing composition) with a water content of about 50%.

(IV-2) Step of Removing Fatty Acids and/or Hydroxy Fatty Acids (Fatty Acid Removal Step)

The low-toxicity SL-containing composition of the present invention can be produced by subjecting an SL-containing culture or a treated product of the culture to at least the step of (1) removing fatty acids and/or hydroxy fatty acids.

Examples of fatty acid removal methods include (a) solvent extraction, (b) adsorption, and (c) chromatography. These fatty acid removal methods may be used singly, or in a combination of two or more. When two or more treatments are used in combination, the treatments can be performed in any order, and the order is not particularly limited. As in the order of (a)→(c), or (b)→(c), it is preferable to perform solvent extraction or adsorption first.

(a) Solvent Extraction

The solvent extraction is a separation method using the property that fatty acids and hydroxy fatty acids are more hydrophobic than SLs. The solvent extraction is generally a method for extracting and removing fatty acids and hydroxy fatty acids, which are hydrophobic compounds, from an SL-containing solution by using a solvent that is incompatible with an SL-containing solution (typically water). Any solvent that is incompatible with the SL-containing solution may be used as the solvent. Examples of such solvents include, but are not limited to, ethyl acetate, diethyl ether (ether), hexane, and the like. Diethyl ether (ether) is particularly preferable in view of a high recovery rate of acidic SL, and a high removal rate of fatty acids and hydroxy fatty acids.

To increase the removal rate of fatty acids and hydroxy fatty acids, the pH of the SL-containing solution to be treated is preferably adjusted to an acidic range beforehand. Adjusting the pH of the SL-containing solution to an acidic range protonates carboxyl groups of fatty acids and hydroxy fatty acids, thus facilitating their recovery in a solvent. The acidic range is not particularly limited, and may be, for example, about pH 6 or less. Specifically, the acidic range is about pH 1 to less than about pH 6, preferably about pH 1 to 5, more preferably about pH 1 to 4.5, and particularly preferably about pH 2 to 4. For adjusting the SL-containing solution (SL-containing culture or a treated product thereof) to an acidic range, a pH adjusting agent is typically used. Examples of pH adjusting agents include inorganic acids such as sulfuric acid, hydrochloric acid, nitric acid, phosphoric acid, boric acid, and hydrofluoric acid; organic acids such as formic acid, acetic acid, malic acid, citric acid, oxalic acid, glutamic acid, and aspartic acid; and the like.

Specific operation steps of the solvent extraction are explained below, taking as an example the case of using diethyl ether (ether) as a solvent and using sulfuric acid as a pH adjusting agent. First, the SL-containing composition (SL-containing culture or a treated product thereof) is added to a separatory funnel to achieve an ethanol-soluble content of 20 mass %, and is adjusted to pH 3. The total volume is adjusted to 100 mL with distilled water. Subsequently, ½ to 2 volumes of ether is added thereto and the resulting mixture is vigorously mixed and allowed to stand. The resulting lower layer is transferred to another separatory funnel. Further, ½ to 2 volumes of ether is added to the aqueous phase transferred to the separatory funnel, and the resulting liquid is vigorously mixed and allowed to stand in the same manner as above. Such an extraction operation is performed at least twice, more preferably three times or more. After the extraction, ether is preferably removed by heating or reducing pressure.

(b) Adsorption

The adsorption is a separation method utilizing the differences in affinity of SLs, fatty acids, and hydroxy fatty acids to the adsorbent used. Compounds that can selectively adsorb hydrophobic compounds can be generally used as the adsorbent. Examples include activated carbon, silica gel, zeolite, ion-exchange resins, and the like. The aluminum oxide disclosed in JP2008-64489A can also be used. Activated carbon is particularly preferable for adsorbing highly hydrophobic compounds. Examples of ion-exchange resins include strongly acidic cation exchange resins, weakly acidic cation exchange resins, strongly basic anion exchange resins, and weakly basic anion exchange resins. Strongly basic anion exchange resins and weakly basic anion exchange resins are preferable.

To increase the removal rate of fatty acids and hydroxy fatty acids, the pH of the SL-containing solution to be treated is preferably adjusted to an acidic range beforehand. Adjusting the pH of the SL-containing solution to an acidic range protonates carboxyl groups of fatty acids and hydroxy fatty acids, thus facilitating their adsorption on an adsorbent. The acidic range is not particularly limited, and may be, for example, about pH 6 or less. More specifically, the acidic range is about pH 1 to less than about pH 6, preferably about pH 1 to 5, more preferably about pH 1 to 4.5, and particularly preferably about pH 2 to 4. For adjusting the SL-containing solution (SL-containing culture or a treated product thereof) to an acidic range, a pH adjusting agent is typically used. Usable pH adjusting agents may be the same as those explained above in (a).

Specific operation steps of the adsorption are explained below, taking as an example the case of using activated carbon as an adsorbent and using sulfuric acid as a pH adjusting agent. First, the SL-containing composition (SL-containing culture or a treated product thereof) in an amount corresponding to 30 mass % of its ethanol-soluble content is adjusted to pH 3 by adding sulfuric acid. Activated carbon is added thereto in an amount of 5 to 15 mass %, based on the total amount of the SL-containing composition and the activated carbon, and mixed. The mixture can be heated in view of enhancing the adsorption efficiency of fatty acids and hydroxy fatty acids with activated carbon and removing activated carbon by filtration. The heating temperature is not particularly limited, and may be, for example, in the range of 40° C. to less than 100° C., preferably 50° C. to less than 100° C., more preferably 55° C. to less than 100° C., particularly preferably 60° C. to less than 100° C.

(c) Chromatography

Chromatography is a separation method utilizing the structure of SLs, which are amphiphilic. As the filler (adsorbent) used as a stationary phase, any filler known in the art, such as silica gel, octadecyl silica gel (ODS) resins, ion-exchange resins, and synthetic adsorbents, can generally be used. The chromatography used in the present invention is preferably partition chromatography, and particularly preferably reverse-phase chromatography. With reverse-phase chromatography, an eluent (mobile phase) that is highly safe for the environment and human body can be used.

When reverse-phase chromatography is used as the chromatography, an ODS resin or the like is preferably used as a filler. When an ODS resin comprising a silica gel support chemically modified with a hydrophobic octadecyl group or the like is used, fatty acids and hydroxyl fatty acids can be efficiently removed from the SL-containing composition (SL-containing culture or a treated product thereof) by utilizing a hydrophobic interaction with alkyl side-chains of SLs. As an eluent (mobile phase) of reverse-phase chromatography, a solvent having a stronger polarity than the filler used as the stationary phase is preferably used from the standpoint of isolation efficiency etc. Examples of such eluents include mixtures of water with a lower alcohol, such as methanol or ethanol. A mixture of water and ethanol is preferable from the standpoint of safety and the environment. The eluent preferably contains volatile acid component(s) in an amount of 0.01 to 0.2 volume %, and preferably 0.05 to 0.1 volume %. Examples of such acid components include formic acid, acetic acid, and trifluoroacetic acid (TFA).

To increase the amount of adsorption of acidic SL on the stationary phase and raise the recovery rate of acidic SL, the pH of the SL-containing solution to be subjected to chromatography is preferably adjusted to an acidic range beforehand. Since the pKa value of the acidic SL is pH 6.1 to 6.4, the acidic range is preferably less than about pH 6. More specifically, the acidic range is preferably about pH 1 to less than about pH 6, more preferably about pH 1 to 5, particularly preferably about pH 1 to 4.5, and particularly preferably about pH 2 to 4. For adjusting the SL-containing solution (SL-containing culture or a treated product thereof) to an acidic range, a pH adjusting agent is typically used. Usable pH adjusting agents may be the same as those explained above in (a).

Specific operation steps of the chromatography are explained below, taking as an example the case of using an ODS resin as a stationary phase and using an aqueous ethanol solution as a mobile phase. After the SL-containing composition (SL-containing culture or a treated product thereof) is supplied to a stationary phase, an eluent (aqueous ethanol solution) having an ethanol concentration of about 70% to less than 80% (% means volume %; the same applies hereinafter) is poured to collect an acidic SL-containing fraction while impurities, such as fatty acids and hydroxy fatty acids, are adsorbed and retained. Specifically, for example, the following method can be used.

(1) An eluent having a concentration of about 70% to less than 80% (for example, an eluent (an aqueous ethanol solution) having an ethanol concentration of about 70% to less than about 80%) is supplied from the topmost part of a column (hereinafter, separation-column overhead) to equilibrate the column.
(2) An SL-containing composition (a treated product of the SL-containing culture) is added from the separation-column overhead.
(3) The eluent having a concentration of about 70% to less than 80% is poured from the separation-column overhead to selectively elute and collect an acidic SL-containing fraction.

In each of steps (1) and (3), the ethanol concentration of the eluent may be increased over time within the above-mentioned concentration range (gradient elution method), or may be maintained at the same concentration within the above-mentioned concentration range (step-wise elution method). Preferably, the latter step-wise elution method is used. An example of the step-wise elution method is as follows. To a stationary phase (a column filler) equilibrated with an aqueous ethanol solution having an ethanol concentration of 70% (step (1)), an SL-containing composition is added (step (2)). Subsequently, an aqueous ethanol solution having an ethanol concentration of 70% is poured (step (3)) to elute and collect the desired acidic SL-containing fraction (step (3)). Before step (3), an aqueous ethanol solution having an ethanol concentration of less than 70% may be used in order to remove odorous components, coloring components, and salts contained in the SL-containing culture from the acidic SL-containing fraction (Step (3')). In this case, the concentration of the aqueous ethanol solution used in step (3') is adjusted to the same as the ethanol concentration equilibrated in step (1).

The low-toxicity SL-containing composition of the present invention can be prepared by subjecting an SL-containing culture or a treated product thereof to, in addition to the above step (1) of removing fatty acids and/or hydroxy fatty acids (fatty acid removal step), at least one of the steps of (2) removing acetyl groups of SLs (deacetylation step), and (3) removing lactonic SL (lactonic SL removal step). These treatment steps are explained below.

(IV-3) Step of Removing Acetyl Groups of SLs (Deacetylation Step)

Examples of deacetylation methods include (d) hydrolysis treatment and (e) enzyme treatment. These deacetylation methods may be used alone, or in a combination of two or more. When two or more treatments are used in combination, the treatments can be performed in any order, and the order is not particularly limited. The deacetylation step is a treatment step preferably used when an SL-containing culture or a treated product thereof is produced by an SL-producing yeast that produces acetylated SLs. The deacetylation step is not used when an SL-containing culture or a treated product thereof is prepared using an SL-producing yeast that selectively produces non-acetylated SLs (an acetyltransferase-deleted SL-producing yeast).

(d) Hydrolysis Treatment

For hydrolysis treatment, methods widely known can be used, as long as they do not interfere with the effect of the present invention. For example, alkaline hydrolysis using a base, such as a metal (e.g., sodium, potassium, calcium, magnesium, etc.) salt of a hydroxide, a phosphate, a carbonate, or an alkanolamine, can be suitably used. Further, the hydrolysis treatment may also be performed using various catalysts, such as alcohols. The temperature, pressure, and time for conducting the alkaline hydrolysis are not particularly limited as long as the object and effect of removing acetyl groups contained in an SL-containing culture or a treated product thereof are achieved. However, it is preferable to use a temperature, pressure, and time that allow efficient progression of the deacetylation while inhibiting side reactions, such as degradation and chemical modification of acidic SL, which is the desired product. From this standpoint, the reaction temperature is typically in the range of about 30 to 120° C., and preferably about 50 to 90° C. The pressure is typically in the range of about 1 to 10 atm, and preferably about 1 to 2 atm. The reaction time is typically in the range of about 10 minutes to about 5 hours, and preferably about 1 to 3 hours. Furthermore, the time for conducting the alkaline hydrolysis can be suitably set according to the number of acetyl groups bound to SLs in the SL-containing composition to be treated.

(e) Enzyme Treatment

The method for removing acetyl groups bound to the SLs using an enzyme is a method utilizing an enzyme that produces an alcohol and acetic acid from acetyl ester. Acetyl ester is typically used as the enzyme. For example, acetyl esterase isolated from *Aspergillus niger*, *Rhodococcus* sp., or *Meyerozyma guilliermondii* can be used.

The conditions that are suitable for the reaction of acetyl esterase are pH 5 to 8, and preferably 6 to 7.5. As long as the pH can be adjusted within this range, any pH adjusting agent commonly used can be used. Examples of usable pH adjusting agents include sodium hydroxide, potassium hydroxide, sulfuric acid, hydrochloric acid, and the like. The reaction temperature is preferably 20° C. to 40° C., and particularly preferably 20° C. to 35° C. The reaction time is typically 6 hours or more, preferably 12 hours or more, and particularly preferably 1 day or more.

The deacetylation treatment using an enzyme is not particularly limited as long as it does not interfere with the object and effect of the present invention. One example of usable methods comprises adding the SL-containing composition to a 0.1M aqueous phosphoric acid solution (pH 7.0) to a concentration of 10 mass %, adding acetyl esterase at 50 U, and then stirring at room temperature (25° C.) for 1 day.

(IV-4) Step of Removing Lactonic SL (Lactonic SL Removal Step)

Examples of methods for removing lactonic SL include (f) hydrolysis treatment and (g) chromatography. These lactonic SL-removing methods can be used singly, or in a combination of two or more. When two or more treatments are used in combination, the treatments can be performed in any order, and the order is not particularly limited. However, the order of (f)→(g) is preferable. The lactonic SL removal step is a treatment step preferably used when an SL-containing culture or a treated product thereof is produced by using an SL-producing yeast that produces both acidic SL and lactonic SL (a lactonic/acidic SL-producing yeast). The lactonic SL removal step is not used when an SL-containing culture or a treated product thereof is produced by using an SL-producing yeast that selectively produces acidic SL (an acidic SL-producing yeast).

(f) Hydrolysis Treatment

The hydrolysis treatment as used herein is a treatment of opening lactone ring of lactonic SL contained in an SL-containing culture or a treated product thereof to convert the lactonic SL into acidic SL.

For the hydrolysis treatment, methods widely known can be used as long as they do not interfere with the effect of the present invention. For example, alkaline hydrolysis using a base, such as a metal (e.g., sodium, potassium, calcium, magnesium, etc.) salt of a hydroxide, a phosphate, a carbonate, or an alkanolamine, can be suitably used. Further, the hydrolysis treatment may also be performed using various catalysts, such as alcohols. The temperature, pressure, and time for conducting the alkaline hydrolysis are not particularly limited as long as the object and effect of opening lactone ring of lactonic SL contained in an SL-containing culture or a treated product thereof can be achieved. However, it is preferable to use a temperature, pressure, and time that allow efficient progression of the lactone ring opening while inhibiting side reactions, such as degradation and chemical modification of acidic SL, which is the desired product. From this standpoint, the reaction temperature is typically in the range of about 30° C. to 120° C., and preferably about 50° C. to 90° C. The pressure is typically in the range of about 1 to 10 atm, and preferably about 1 to 2 atm. The reaction time is typically in the range of about 10 minutes to about 5 hours, and preferably about 1 to 3 hours. Furthermore, the time for conducting the alkaline hydrolysis can be suitably set according to the proportion of lactonic SL contained in the SL-containing composition to be treated.

(g) Chromatography

The chromatography as used herein is a treatment for selectively removing lactonic SL contained in an SL-containing culture or a treated product thereof.

Generally, as a filler (adsorbent) used as the stationary phase, any filler known in the art, such as silica gel, octadecyl silica gel (ODS) resins, ion-exchange resins, and synthetic adsorbents, can be used. The chromatography used in the present invention is preferably partition chromatography, and particularly preferably reverse-phase chromatography.

When reverse-phase chromatography is used as the chromatography, the filler is preferably an ODS resin or the like. From the standpoint of isolation efficiency etc., a solvent having a stronger polarity than the filler used as the stationary phase is preferably used as the eluent (mobile phase) of reverse-phase chromatography. Examples of such eluents include mixtures of water with a lower alcohol, such as methanol or ethanol. A mixture of water and ethanol is preferable from the standpoint of safety and the environment. The eluent preferably contains volatile acid component(s) in an amount of 0.01 to 0.2 volume %, and preferably 0.05 to 0.1 volume %. Examples of such acid components include formic acid, acetic acid, and trifluoroacetic acid (TFA).

To increase the amount of acidic SL adsorbed on the stationary phase and raise the recovery rate of acidic SL, the pH of the SL-containing solution to be treated is preferably adjusted to an acidic range beforehand. Since the pKa value of acidic SL is pH 6.1 to 6.4, the acidic range is preferably less than about pH 6. The pH is preferably about pH 1 to less than about pH 6, more preferably about pH 1 to 5, particularly preferably about pH 1 to 4.5, and particularly preferably about pH 2 to 4. Adjusting the SL-containing solution (SL-containing culture or a treated product thereof) to an acidic range is typically performed by using a pH adjusting agent. Usable pH adjusting agents may be the same as explained above in (a).

Specific operation steps of the chromatography are explained below, taking as an example the case of using an ODS resin as a stationary phase and using an aqueous ethanol solution as a mobile phase. After the SL-containing composition (SL-containing culture or a treated product thereof) is supplied to a stationary phase, an eluent (an aqueous ethanol solution) having an ethanol concentration of about 70% to less than 80% (% means volume %; the same applies hereinafter) is poured to collect an acidic SL-containing fraction while impurities, such as lactonic SL, are adsorbed and retained. Specifically, for example, the following method can be used.

(1) An eluent having a concentration of about 70% to less than 80% (for example, an eluent (an aqueous ethanol solution) having an ethanol concentration of about 70% to less than about 80%) is supplied from the topmost part of a column (hereinafter, the separation-column overhead) to equilibrate the column.

(2) An SL-containing composition (a treated product of the SL-containing culture) is added from the separation-column overhead.

(3) The eluent having a concentration of about 70% to less than 80% is poured from the separation-column overhead to selectively elute and collect an acidic SL-containing fraction.

In each of steps (1) and (3), the ethanol concentration of the eluent may be increased over time within the above-mentioned concentration range (gradient elution method), or may be maintained at the same concentration within the above-mentioned concentration range (step-wise elution method). Preferably, the latter step-wise elution method is used. An example of the stepwise elution is as follows. To a stationary phase (a column filler) equilibrated with an aqueous ethanol solution having an ethanol concentration of 70% (step (1)), an SL-containing composition is added (step (2)). Subsequently, an aqueous ethanol solution having an ethanol concentration of 70% is poured (step (3)) to elute and collect the desired acidic SL-containing fraction (step (3)). Before step (3), an aqueous ethanol solution having an ethanol concentration of less than 70% may be used to remove odorous components, coloring components, and salts in the SL-containing culture from the acidic SL-containing fraction [Step (3')]. In this case, the concentration of the aqueous ethanol solution used in step (3') is adjusted to the same as the ethanol concentration equilibrated in step (1).

The method for producing the low-toxicity SL-containing composition of the present invention may be carried out by subjecting an SL-containing culture or a treated product thereof to the above fatty acid removal step (IV-2) alone, or subjecting an SL-containing culture or a treated product thereof to a combination of the fatty acid removal step (IV-2) with the deacetylation step (IV-3) and/or the lactonic SL removal step (IV-4). In this case, the order of these steps is not particularly limited as long as the object of the present invention can be achieved.

Examples of such a combination of two or more steps include the following. When the SL-containing culture or treated product thereof is produced by using an acidic SL-producing yeast (see, for example, PTL 1), the deacetylation step (IV-3) (for example, (d) to (e)) may be performed after the fatty acid removal step (IV-2) (for example, (a) to (c)). Conversely, the fatty acid removal step ((a) to (c)) (IV-2) may be performed after the deacetylation step (IV-3) (e.g., (d) to (e)). Although this is not limitative, the fatty acid removal step (IV-2) is preferably performed after the deacetylation step (IV-3). Specifically, for example, after at least one treatment selected from (d) hydrolysis and (e) enzyme treatment, at least one treatment selected from (a) solvent extraction, (b) adsorption, and (c) chromatography may be performed. Preferable is a combination of (d) hydrolysis with (a) solvent extraction and/or (c) chromatography.

For example, when an SL-containing culture or a treated product thereof is produced by using a lactonic/acidic SL-producing yeast (see, for example, Reference Production Example 1), at least one of the fatty acid removal step (IV-2) (for example, (a) to (c)) and the deacetylation step (IV-3) (for example, (d) to (e)) may be performed in combination in any order after the lactonic SL removal step (IV-4) (for example, (f) to (g)). Since (f) and (g) that are the lactonic SL removal step (IV-4) overlap with (d) of the deacetylation step (IV-3) and (c) of the fatty acid removal step (IV-2), the deacetylation (IV-3) or the fatty acid removal (IV-2) can be simultaneously performed by carrying out the lactonic SL removal treatment (IV-4). A preferable combination may be, for example, a method in which after hydrolysis (d) (or (f)), at least one treatment selected from solvent extraction (a) and chromatography (c) (or (g)) is performed.

Further, for example, when an SL-containing culture or a treated product thereof is prepared using an acetyltransferase-deleted SL-producing yeast (see, for example, Non-patent Literature (NPL) 2), the lactonic SL removal step (IV-4) (for example, (f) to (g)) and the fatty acid removal step (IV-2) (for example, (a) to (c)) may be performed in combination in any order. A preferable combination may be, for example, a method in which after (f) hydrolysis, at least one treatment selected from (a) solvent extraction and (c) chromatography is performed.

(V) Method for Reducing the Toxicity of an SL-containing Composition

According to the production method described above, an SL-containing composition prepared from an SL-producing yeast is rendered less toxic and less irritating to provide a low-toxicity SL-containing composition of the present invention. Accordingly, the above production method can be paraphrased as a method for reducing the toxicity or irritancy of an SL-containing composition produced by culturing an SL-producing yeast.

The method for reducing the toxicity (or the method for reducing irritation) can be carried out according to the method described above in (IV). All of the descriptions in section (IV) above can be incorporated herein by reference. The low-toxicity SL-containing composition of the present invention explained in section (III) can be prepared and obtained by using the method for reducing the toxicity (or the method for reducing irritation). Accordingly, for the low-toxicity SL-containing composition obtained by reducing the toxicity and irritation of an SL-containing composition produced by using an SL-producing yeast, all of the descriptions in section (III) are incorporated herein by reference.

EXAMPLES

The present invention is described below more specifically with reference to Examples and Test Examples. However, the invention is not limited thereto or thereby, and various modifications are possible within the spirit of the present invention by a person skilled in the art.

Reference Production Example 1

Production of SLs (Preparation of Crudely Purified SL-containing Composition-1)

A liquid medium containing, per liter, 10 g of aqueous glucose (produced by Nihon Shokuhin Kako Co., Ltd., product name: Nisshoku Gansui Kessho Budoto), 10 g of peptone (produced by Oriental Yeast Co., Ltd., product name: Peptone CB90M), and 5 g of a yeast extract (produced by Asahi Food & Healthcare Co., Ltd., product name: Meast Powder N) was used as a culture medium. *Candida bombicola* ATCC 22214 was cultured in the medium while shaking at 30° C. for two days. This was used as a pre-culture broth.

The pre-culture broth was inoculated into a main culture medium (3 L) in a 5-liter fermenter in an amount of 4 mass %, based on the total amount of the medium, and then cultured at 30° C. at an aeration rate of 0.6 vvm for 6 days for fermentation. The main culture medium contained, per liter, 100 g of aqueous glucose, 50 g of palm olein (produced by NOF Corporation, product name: Palmary 2000), 50 g of oleic acid (produced by Acid Chem, product name: Palmac 760), 1 g of sodium chloride, 10 g of monopotassium phosphate, 10 g of magnesium sulfate heptahydrate, 2.5 g of a yeast extract (produced by Asahi Food & Healthcare Co., Ltd., product name: Meast Powder N), and 1 g of urea (pH 4.5 to 4.8 before sterilization).

On the 6th day from the start of culturing, the fermentation was stopped. The culture broth removed from the fermenter was heated, then returned to room temperature, and allowed to stand for 2 to 3 days. As a result, the culture broth was separated into the following three layers in this order from the bottom: a liquid brown precipitate layer; a milky-white solid layer presumably mainly containing fungal cells; and a supernatant. After the supernatant was removed, industrial water or groundwater was added in an amount equal to the amount of the supernatant removed. While the resulting mixture was stirred, a 48 mass % aqueous sodium hydroxide solution was gradually added to adjust the pH to 6.5-6.9, thus solubilizing SLs contained in the culture broth. The resulting product was centrifuged by a tabletop centrifuge (Westfalia: produced by Westfalia Separator AG) to precipitate milky-white solids, and a supernatant was collected. While the collected supernatant was stirred, an aqueous sulfuric acid solution having a concentration of 62.5 mass % was gradually added to adjust the pH to 2.5-3.0, thus insolubilizing SLs again. After the resulting mixture was allowed to stand for 2 days, the supernatant was removed by decantation as much as possible, thus obtaining the residue as a crudely purified SL-containing composition-1 (with an about 50% water content, Reference Example 1).

Reference Production Example 2

Preparation of Crudely Purified SL-containing Composition-2

The crudely purified SL-containing composition-1 obtained in the above Reference Production Example 1 was adjusted to pH 14 by adding an aqueous sodium hydroxide solution, and the resulting mixture was heat-treated at 80° C. for 2 hours to perform hydrolysis (alkali hydrolysis). Subsequently, the hydrolysate was returned to room temperature, and then adjusted to pH 7.5 by using sulfuric acid (9.8M aqueous solution). The resulting insoluble matter was removed by filtration to obtain a filtrate as a "crudely purified acidic SL-containing composition-2" (Reference Production Example product 2).

Example 1

Preparation of a Low-toxicity SL-containing Composition

The crudely purified acidic SL-containing composition-2 obtained in Reference Production Example 2 was adjusted to pH 3.0 by using sulfuric acid (9.8M aqueous solution).

This was subjected to reverse-phase column chromatography under the following conditions:
solid phase: C18 column (COSMOSIL 40C18-PREP, produced by Nacalai Tesque, Inc., 15 kg);
mobile phases: 50% and 70% aqueous ethanol solutions.

Specifically, 1.2 kg of the crudely purified acidic SL-containing composition-2 adjusted to pH 3.0 (the crudely purified acidic SL-containing composition-2 in an amount of about 3%, in terms of its ethanol-soluble content, relative to 15 kg of the stationary phase load amount) was added to a C18 column. First, 35 L of a 50% ethanol aqueous solution was supplied to remove water-soluble impurities (odors, salts, and a part of coloring components) by elution. Subsequently, 30 L of a 70% ethanol aqueous solution was supplied to the column to collect the first 15 L from the start of elution with the 70% ethanol solution as an SL-containing fraction.

The obtained SL-containing solution was subjected to an evaporator (produced by Toyo Chemical Food Plant Co., Ltd.) to distill off the solvent (ethanol) and concentrate the solution. The concentrate was subjected to a spray-dryer (drying pulverizer) (model: R-3, made of SUS304, water evaporation capacity: Max. 5 kg/h, produced by Sakamotogiken Co., Ltd.) to obtain a dry powder. The spray-drying conditions were as follows:
atomizer: 12,000 rpm; and temperature in the chamber: 105° C. As a result, a fine powder was obtained (Example product 1).

Example 2

Production of Low-toxicity SL-containing Composition

The crudely purified acidic SL-containing composition obtained in Reference Production Example 2 was adjusted to pH 3.0 by using sulfuric acid (9.8M aqueous solution).

1.2 kg of the crudely purified SL-containing composition-2 adjusted to pH 3.0 was poured into a separatory funnel, and 400 ml of diethyl ether was added and mixed. After the mixture was separated into two layers, the lower layer was collected in another separatory funnel. 400 ml of diethyl ether was added again, and extraction with diethyl ether was performed three times. The liquid collected from the lower layer was allowed to stand at 50° C. until ether odor could no longer be smelled. The collected liquid was subjected to reverse-phase column chromatography in the same manner as in Example 1. Specifically, after the collected liquid from which diethyl ether was removed by evaporation was added to a C18 column, 35 L of a 50% ethanol aqueous solution was first supplied thereto to remove water-soluble impurities (odors, salts, and a part of coloring components) by elution. Subsequently, 30 L of a 70% ethanol aqueous solution was supplied to the column to collect the first 15 L from the start of elution with the 70% ethanol solution as a SL-containing fraction.

The obtained SL-containing solution was subjected to an evaporator (produced by Toyo Chemical Food Plant Co., Ltd.) to distill off the solvent (ethanol) and thereby concentrated. The concentrate was subjected to a spray-dryer (drying pulverizer) (model: R-3, made of SUS304, water evaporation capacity: Max. 5 kg/h, produced by Sakamotogiken Co., Ltd.) to obtain a dry powder. The spray-drying conditions were as follows: atomizer: 12,000 rpm; and temperature in the chamber: 105° C. As a result, a fine powder was obtained (Example product 2).

Examples 3 to 7

Production of Low-toxicity SL-containing Compositions

The crudely purified acidic SL-containing composition-2 obtained in Reference Production Example 2 was adjusted to pH 3.0 by using sulfuric acid (9.8M aqueous solution). This was extracted with diethyl ether (ether) by the following method (solvent extraction).

Specifically, the crudely purified SL-containing composition-2 adjusted to pH 3.0 was placed in a 50-ml glass centrifuge tube with a screw cap in an amount of 3 g in terms of ethanol-soluble content, and distilled water was added to make the total volume 15 ml. After this was mixed with each of the following volumes of ether and vigorously mixed, the resulting mixture was centrifuged at 200×g for 2 minutes to separate the mixture into two layers. The upper ether layer was removed (extraction operation). This extraction operation was performed the number of times described below.
Example 3: One time of extraction using 3 ml of ether (→Example product 3).
Example 4: One time of extraction using 7 ml of ether (→Example product 4).
Example 5: One time of extraction using 15 ml of ether (→Example product 5).
Example 6: Two times of extraction using 15 ml of ether (→Example product 6).
Example 7: Three times of extraction using 15 ml of ether (→Example product 7).

Thereafter, the extracts were allowed to stand at 50° C., and ether was removed to obtain SL-containing compositions (Example products 3 to 7).

Examples 8 to 10

Production of Low-toxicity SL-containing Compositions

The crudely purified SL-containing composition-1 obtained in the above Reference Production Example 1 was adjusted to pH 14 by adding an aqueous sodium hydroxide solution, and was hydrolyzed (subjected to alkaline hydrolysis) by heating at 80° C. for 15 minutes (Example 8), at 80° C. for 30 minutes (Example 9), and at 80° C. for 45 minutes (Example 10).

Each of the hydrolysates was returned to room temperature, and then adjusted to pH 7.5 by adding sulfuric acid (9.8M aqueous solution). The resulting insoluble matter was removed by filtration. Further, each of the resulting mixtures was adjusted to pH 3.0 using sulfuric acid (9.8M aqueous solution) and placed in a 50-ml glass centrifuge tube with a screw cap in an amount of 3 g in terms of the ethanol-soluble content, and distilled water was added to make the total volume 15 ml. After hexane was added and vigorously mixed, each mixture was centrifuged at 200×g for 2 minutes to separate the mixture into two layers, and the upper hexane layer was removed (extraction operation). This extraction operation was performed five times. Each of the extracts was then allowed to stand at 80° C. to remove hexane. SL-containing compositions (Examples products 8 to 10) were thus obtained.

Test Example 1

Methods for Measuring Physical Properties of Each Sample

The ester value (mg KOH/g), hydroxyl value (mg KOH/g), ether extract content (%), hue ($OD_{440}$), evaporation residue (%), loss on drying (%), ethanol-soluble content (%), and infrared absorption spectrum ($cm^1$) of the SL-containing compositions obtained in the above Reference Production Examples 1 and 2 and Examples 1 to 10 (crudely purified SL-containing composition-1, crudely purified SL-containing composition-2, and Example products 1 to 10) were measured according to the following methods. HPLC analysis was also performed.

(1) Summary of the Tests

TABLE 1

| Test item | Components to be measured | Measurement details | Method applied |
|---|---|---|---|
| Ester value (mg KOH/g) | Ester bonds in lactone rings, and acetyl groups | Amount (mg) of potassium hydroxide required for complete saponification of esters contained in a sample in an amount corresponding to 1 g of its ethanol-soluble content | The JOCS Standard Methods for the Analysis of Fats, Oils and Related Materials (2.3.3-1996) defined by the Japan Oil Chemists' Society |
| Hydroxyl value (mg HOH/g) | Free hydroxyl groups in the structure | Amount (mg) of potassium hydroxide required for neutralizing acetic acid necessary for acetylating free hydroxyl groups contained in a sample in an amount corresponding to 1 g of its ethanol-soluble content | The JOCS Standard Methods for the Analysis of Fats, Oils and Related Materials (2.3.6.2-1996) defined by the Japan Oil Chemists' Society |
| Ether extract content (%) | Fatty acids and hydroxyl fatty acids | Amount of substances contained in and extracted with ethanol from a sample in an amount corresponding to 1 g of its ethanol-soluble content and expressed in mass % | |
| Constituents of ether extract (%) | Compositions of fatty acids and hydroxyl fatty acids | Compositions (mass %) of fatty acids and hydroxyl fatty acids contained in the substances extracted with ether from a sample in an amount | |

TABLE 1-continued

| Test item | Components to be measured | Measurement details | Method applied |
|---|---|---|---|
| | | corresponding to 1 g of its ethanol-soluble content, the compositions being calculated from area values obtained by HPLC analysis and expressed in mass % | |
| Hue ($OD_{440}$) | Coloring components derived from fermented culture | Absorbance at 440 nm of an aqueous solution prepared by dissolving a sample in an alkaline solution so that the resulting solution has a concentration of the ethanol-soluble content of 10 mass % | |
| Evaporation residue (%) | Mass measurement of coexisting substances (in particular, coexisting substances having a high boiling point) in a sample | Amount (mass %) of the residue obtained by evaporation of a sample | The Second Method in JIS K0067-1992 |
| Loss on drying (%) | Mass measurement of water and other volatile substances (low boiling-point compounds) contained in a sample | Loss (mass %) of a sample when it is dried | The First Method in JIS K0067-1992 (Method of heat-drying under atmospheric pressure) |
| Ethanol-soluble content (%) | Mass measurement of ethanol-soluble substances (polar substances such as surfactants) in a sample | Proportion (mass %) of ethanol-soluble content | JISK3362-2008 |
| Ignition residue (%) | Inorganic compounds contained in a sample (in terms of sulfates) | | The First Method in the Japanese Standards of Quasi-drug Ingredients 2006 (Japan) or JIS K0067-1992 |
| Infrared absorption spectrum | —$CH_2$ and —$CH_3$ contained in alkyl chains, —COOH bound to alkyl chains, and C—OH of glucose in a sample | Spectra of wavelengths absorbed when a sample is irradiated with electromagnetic waves in the infrared region | Infrared spectroscopy (ATR method) |

(2) Test Method
(A) Ester Value

The ester value can be determined as the difference between the saponification value (the amount (mg) of potassium hydroxide required to neutralize free acids contained in a sample in an amount corresponding to 1 g of its ethanol-soluble content and to saponify esters contained in a sample in an amount corresponding to 1 g of its ethanol-soluble content: JIS K 3331, The JOCS Standard Methods for the Analysis of Fats, Oils and Related Materials (2.3.2.1-1996)), and the acid value (the amount (mg) of potassium hydroxide required to neutralize free acids contained in a sample in an amount corresponding to 1 g of its ethanol-soluble content: JIS K 3331, The JOCS Standard Methods for the Analysis of Fats, Oils and Related Materials (2.3.1-1996)). Alternatively, as a method for direct measurement, the following method can also be used.

Direct Method

About 3 g of a sample is accurately weighed into a saponification flask, and 50 mL of 95 vol % ethanol is added. While swirling the flask well and using a phenolphthalein indicator, the sample is neutralized by titration with a 0.1 mol/L potassium hydroxide standard solution (to thereby obtain an acid value). Subsequently, 25 mL of a 0.5 mol/L potassium hydroxide-ethanol standard solution is accurately added, and a flask is equipped with a condenser. The flask is gently heated with occasional swirling, while adjusting the heating temperature so that the refluxing ethanol does not reach the upper end of the condenser. Immediately after the content of the flask is boiled for 30 minutes, the flask is cooled. The condenser is removed before the content hardens into an agar-like state. Several drops of the phenolphthalein indicator are added, and titration is performed with a 0.5 mol/L hydrochloric acid standard solution. Thirty seconds after the disappearance of a slight crimson color of the indicator is defined as the terminal point. The amount of the 0.5 mol/L hydrochloric acid standard solution required to reach this point is defined as "the amount (mL) of 0.5 mol/L hydrochloric acid standard solution used in this test." For comparison, a blank test is concurrently performed by weighing 50 mL of 95 vol % ethanol into a flask, and precisely adding 25 mL of the 0.5 mol/L hydrochloric acid standard solution. The amount of the 0.5 mol/L hydrochloric acid standard solution required in the blank test is defined as "the amount (mL) of the 0.5 mol/L hydrochloric acid standard solution used in the blank test." The ester value of 1 g of the sample is calculated from Formula 1 below. The ester value of the sample in an amount corresponding to 1 g of its ethanol-soluble content is calculated from the ethanol-soluble content (%) of the sample according to Formula 2 below.

$$\text{Ester value of 1 g of the sample} = [28.05 \times (A-B) \times F]/C \quad \text{(Formula 1)}$$

A: Amount (mL) of the 0.5 mol/L hydrochloric acid standard solution used in the blank test
B: Amount (mL) of the 0.5 mol/L hydrochloric acid standard solution used in this test
C: Sample amount (g)
F: Factor of the 0.5 mol/L hydrochloric acid standard solution $$\text{Ester value of the sample in an amount corresponding to 1 g of ethanol-soluble content} = [\text{Ester value of 1 g of the sample}] \times 100/D \quad \text{(Formula 2)}$$

D: Ethanol-soluble content (%) of the sample (B) Hydroxyl Value

The hydroxyl value can be obtained from the amount (mg) of potassium hydroxide required for neutralizing acetic acid necessary for acetylating free hydroxyl groups contained in a sample in an amount corresponding to 1 g of the ethanol-soluble matter according to The JOCS Standard Methods for the Analysis of Fats, Oils and Related Materials (2.3.6.2-1996) defined by the Japan Oil Chemists' Society.

Reagent

Acetylated reagent: 12.5 g of acetic anhydride is placed into a 100-ml volumetric flask. Pyridine is added to a marked line. The mixture is mixed well with care. The liquid thus prepared is stored in a brown bottle so as not to expose it to moisture, carbon dioxide, and acid vapor.

Test Method

One gram of a sample is placed into a long-neck, round-bottom flask. An appropriate amount of acetone is added. The resulting mixture is heated at 105° C. to remove water. Thereafter, 5 ml of an acetylated reagent is accurately added and heated to 95 to 100° C. After 1 hour of heating, the flask is removed from the heating bath, and allowed to air-cool. After 1 ml of distilled water is added and mixed, the flask is placed in the heating bath again and heated for 10 minutes. After the flask is raised again and allowed to air-cool, the liquid condensed on the wall of the funnel is added while being washed off with 5 ml of neutral ethanol. A phenolphthalein solution is added to the content of this flask, and titration with 0.5N KOH/EtOH is performed to calculate the hydroxyl value of 1 g of the sample according to the formula below. In Formula 3 below, the acid value is the amount (mg) of potassium hydroxide required to neutralize free acids contained in 1 g of the sample and can be determined according to The JOCS Standard Methods for the Analysis of Fats, Oils and Related Materials (JIS K 3331) [2.3.1-1996)]. The hydroxyl value of the sample in an amount corresponding to 1 g of the ethanol-soluble content can be obtained from the ethanol-soluble content (%) of the sample according to Formula 4.

$$\text{Hydroxyl value (mg KOH/g)} = [(a-b) \times 28.055 \times F]/C + \text{Acid value} \quad \text{(Formula 3)}$$

a: Titer (ml) of 0.5N KOH/EtOH in the blank test (ml)
b: Titer (ml) of 0.5 N KOH/EtOH in this test (ml)
c: Sample amount (g)
F: Factor of 0.5N KOH/EtOH $$\text{Hydroxyl value of the sample in an amount corresponding to 1 g of ethanol-soluble content} = [\text{Hydroxyl value of 1 g of the sample}] \times 100/d \quad \text{(Formula 4)}$$

d: Ethanol-soluble content (%) of the sample (C) Ether Extract Content (%)

The ether extract content is the amount (mass %) of substances extracted with ether from the sample in an amount corresponding to 1 g of its ethanol-soluble content.

Method of Measurement

One gram of a sample was placed in a 50 ml-recovery flask, and 10 ml of a 10% aqueous sodium hydroxide solution was added. A condenser was connected to the flask, and heating was performed at 80° C. for 2 hours. 10 ml of a 10% aqueous hydrochloric acid solution was added for neutralization. While 99.5% ethanol was added, water was distilled off using an evaporator. Thereafter, 10 ml of 99.5% ethanol was added, and the resulting mixture was dispersed with sonication. The dispersion was filtered through a glass funnel, and the filtrate was transferred to a 50-ml recovery flask. After the filtrate was further washed with 99.5% ethanol, the ethanol was distilled off using an evaporator. The residue was transferred to a 15 ml glass centrifuge tube with a screw cap, and adjusted to pH 3 by using sulfuric acid (produced by Kanto Chemical Co., Inc.). After the total volume was adjusted to 5 mL with distilled water, 5 ml of ether was added. The resulting mixture was vigorously mixed and centrifuged at 1,000 rpm for 2 minutes using a tabletop centrifuge H-108M2 (produced by Kokusan Co., Ltd.) to separate the mixture into two layers. The upper layer was transferred to a 100-ml beaker with a known weight, and 5 ml of ether was newly added. The ether extraction operation was performed 3 times in total. The 100-ml beaker containing the ether extract was placed into a 50° C. incubator, and ether was removed. The resulting mixture was further allowed to stand in a 105° C. incubator for 30 minutes to completely remove ether.

After the resulting mixture was returned to room temperature, the weight was measured. The ether extract content in 1 g of the sample was calculated according to Formula 5 below. The ether extract content in the sample in an amount corresponding to 1 g of the ethanol-soluble content of the sample can be calculated from the ethanol-soluble content (%) of the sample according to Formula 6 below.

$$\text{Ether extract content in 1 g of the sample (mass \%)} = \{([\text{Weight of the beaker after removal of ether}] - [\text{Weight of the beaker before the test}])/\text{Sample amount (g)}\} \times 100 \quad \text{(Formula 5)}$$

Ether extract content in the sample in an amount
corresponding to 1 g of ethanol-soluble content
(mass %)={[Ether extract content in 1 g of the
sample (mass %)]}×100/d     (Formula 6)

d: Ethanol-soluble content (%) of the sample (D) Composition Analysis of the Ether Extract by HPLC Analysis The ether extract obtained in the above (C) ether extract content was dissolved in 99.5% ethanol to obtain a 1% solution. HPLC analysis was performed under the conditions shown in the table below. Under these HPLC analysis conditions, acidic SLs were detected during a retention time of 8 to 20 minutes, hydroxy fatty acids were detected during a retention time of 20 to 45 minutes, and fatty acids were detected during a retention time of 44 to 55 minutes. Each peak detected during the retention time of 20 to 55 was compared with the retention time of known hydroxy fatty acids and fatty acids (standard products) to identify the hydroxy fatty acids and fatty acids contained in the sample. The area of peaks of fatty acids or peaks of hydroxyl fatty acids was divided by the sum of the peak areas detected during the retention time of 20 to 55 minutes to calculate the proportion of the fatty acids and the proportion of the hydroxy fatty acids per 1 g of the ethanol-soluble content. That is, the content of fatty acids and the content of hydroxy fatty acids were calculated according to Formula 10 below.

Content (%) of fatty acids or hydroxy fatty
acids=Ether extract content (%)×A1/A2     (Formula 10)

A1: Peak area of fatty acids or hydroxy fatty acids
A2: Sum of the peak areas of fatty acids and hydroxy fatty acids The obtained fatty acids are indicated in the following manner. The number of carbon atoms is indicated after C; after a colon, the number of double bonds is indicated. That is, for example, oleic acid, which has 18 carbon atoms and one double bond, is indicated as C18:1. Hydroxy fatty acids are indicated by adding (OH) at the end. That is, hydroxyoleic acid having 18 carbon atoms is indicated as C18:1(OH).

TABLE 2

| Device | LC-10AD-VP (produced by Shimadzu Corporation) |
|---|---|
| Column | Inertsil ODS-3 (4.5 mm × 250 mm, produced by GL Sciences Inc.) |
| Column temperature | 40° C. |
| Mobile phase | liquid A: Distilled water<br>Liquid B: Methanol containing 0.1% formic acid<br>Gradient: Proportion of liquid B: 70% → 100%/0 → 60 minutes |
| Mobile phase flow rate | 1.0 ml/min |
| Injection volume | 10 μl |
| Detector | Detector: Evaporative light scattering detector ELSD-LT II (produced by Shimadzu Corporation)<br>Temperature: 40° C.<br>Gain: 5<br>Nebulizer gas: Nitrogen<br>Gas pressure: 350 kPa |

(E) Hue ($OD_{440}$)

The hue ($OD_{440\ nm}$) can be obtained by measuring the absorbance at a wavelength of 440 nm of an aqueous solution prepared by dissolving a sample in an aqueous alkaline solution (2% $Na_2CO_3$ in 0.1N NaOH) so that the resulting solution has an ethanol-soluble content of 10 mass %.

(F) Evaporation Residue (%)

After being accurately weighed, a sample is evaporated to dryness according to the Second Method of JIS K0067-1992 (the method of thermal evaporation on a hot plate), and the residue is weighed. The evaporation residue (%) is calculated according to Formula 7 below.

Evaporation residue (%)=([W2−W3]/[W1−W3])×100     (Formula 7)

W1: Total mass (g) of the sample and the sample container
W2: Total weight (g) of the residue and the sample container
W3: Mass (g) of the sample container (G) Loss on Drying (%)

A sample is accurately weighed and then dried by heating (105±2° C., for 2 hours) according to the First Method of JIS K0067-1992 (a method of drying by heating under atmospheric pressure). The reduced amount of the sample after drying is determined. The loss on drying (%) is calculated according to Formula 8 below.

Loss on drying (%)=([W1−W2]/[W1−W3])×100     (Formula 7)

W1: Total mass (g) of the weighing bottle and the sample before drying
W2: Total mass (g) of the weighing bottle and the sample after drying
W3: Mass (g) of the weighing bottle (H) Ethanol-soluble Content (%)

The ethanol-soluble content refers to the amount of substances dissolved in ethanol when ethanol is added to a sample.

Method of Measurement

An Erlenmeyer flask and a glass filter are accurately weighed. The weight of these instruments is measured after being dried at 105° C. for 2 hours or more and allowed to cool in a desiccator. About 5 g of the sample is accurately weighed out to one milligram, and placed into the Erlenmeyer flask. After 100 mL of ethanol is added to the sample, the flask is equipped with a glass tube and heated in a water bath for 30 minutes with occasional swirling for dissolution. For powder or granular samples, 95 vol % ethanol is used. For liquid or paste samples, 99.5 vol % ethanol is used. After the warm solution is filtered through a glass filter, 50 mL of ethanol is added to the residue in the Erlenmeyer flask again to dissolve the residue. The resulting warm solution is filtered using a glass filter, and the Erlenmeyer flask and the glass filter are washed well with hot ethanol. After being allowed to cool to room temperature, the filtrate and the wash are transferred to a 250-mL volumetric flask, and ethanol is added to a marked line. Using a transfer pipette, 100-mL portions of the liquid are aliquoted into two 200-mL beakers with a known mass. One of the beakers is heated in a water bath, and ethanol is removed. The residue is dried for 1 hour in a dryer adjusted to 105±2° C., allowed to cool in a desiccator, and then accurately weighed (dry residue).

Ethanol-soluble content (%) is calculated according to Formula 8 below.

(Formula 8)

Ethanol-soluble content (mass %) = (A/[S×100/250])×100
= ([250×A]/S)

A: Dry residue amount (g)
S: Sample mass (g)

(I) Residue on Ignition

The ignition residue test is a method of measuring the amount of residual substances after a sample is ignited by the method below (the First Method). This method is typically used to measure the amount of inorganic substances contained as impurities in an organic substance. In some cases, this method is also used to measure the amount of inorganic substances contained as components in an organic substance, or the amount of impurities contained in a volatile inorganic substance. For example, in the present invention, "an ignition residue of 0.1% or less (the First Method, 1 g)" means that when about 1 g of a sample is accurately measured and ignited according to the operational procedure of the First Method described below, the residue of the sample after the ignition is 0.10% or less, based on the sampling amount of the sample.

Sampling Method

After a crucible made of platinum, quartz, or ceramics is ignited to constant weight and allowed to cool in a desiccator (silica gel), the mass of the crucible is accurately measured. A predetermined amount (sampling amount) of each sample is accurately weighed (within a measurement error range of ±10%) into the crucible, and the following procedure is performed.

First Method

On the crucible, the sample is moistened with a small amount of sulfuric acid and gradually heated to ash or vaporize most of the sample at as low a temperature as possible. The sample is then moistened with sulfuric acid, completely asked, and ignited (at 450° C. to 550° C.) to constant weight. After the residue is allowed to cool in a desiccator (silica gel), the mass is accurately measured. The ignition residue (%) is calculated from the obtained measurement value (residue) and the pre-measured sampling amount according to Formula 9 below.

$$\text{Ignition residue (\%)} = ([W2-W3]/[W1-W3]) \times 100 \quad \text{(Formula 9)}$$

W1: Total mass (g) of the sampling amount and the sample container (crucible)
W2: Total weight (g) of the residue and the sample container (crucible)
W3: Mass (g) of the sample container (crucible)

(J) Infrared Absorption Spectrum

The liquid sample is used after being dried to a solid by heating at 105±2° C. for 3 hours. The solid sample is used as is. The infrared absorption spectrum is analyzed by the ATR method using a Spectrum™ 100 Fourier transform infrared spectrometer (produced by PerkinElmer Co., Ltd.).

(3) Test Results

Table 3 shows the test results of the SL-containing compositions prepared in the Reference Production Examples and the Examples (crudely purified SL-containing composition-1, crudely purified SL-containing composition-2, and Example products 1 to 10).

TABLE 3

| Test items | | Crudely purified SL-containing composition 1 | Crudely purified SL-containing composition 2 | Example product 1 | Example product 2 | Example product 3 | Example product 4 | Example product 5 |
|---|---|---|---|---|---|---|---|---|
| Ester value (mg KOH/g) | | 177 | 0.1 | 0.05 | 0.04 | 0.1 | 0.1 | 0.1 |
| Hydroxyl value (mg KOH/g) | | 494 | 472 | 584 | 585 | 575 | 580 | 581 |
| Ether extract content (%) | | 8.0 | 8.0 | 0.2 | 0.1 | 4.0 | 2.3 | 1.1 |
| Constituents of ether extract (%) | C16:0 | 0.8 | 0.8 | 0.0708 | 0.0354 | 0.400 | 0.230 | 0.110 |
| | C16:0(OH) | 0.008 | 0.008 | 0 | 0 | 0.004 | 0.002 | 0.001 |
| | C18:0 | 3.008 | 3.008 | 0.0096 | 0.0048 | 1.504 | 0.865 | 0.414 |
| | C18:0(OH) | 0.008 | 0.008 | 0 | 0 | 0.004 | 0.002 | 0.001 |
| | C18:1 | 3.992 | 3.992 | 0.115 | 0.0575 | 1.996 | 1.148 | 0.549 |
| | C18:1(OH) | 0.008 | 0.008 | 0 | 0 | 0.004 | 0.002 | 0.001 |
| | C18:2 | 0.176 | 0.176 | 0.0046 | 0.0023 | 0.088 | 0.051 | 0.024 |
| Hue ($OD_{440}$) | | 0.3 | 0.4 | 0.1 | 0.1 | 0.4 | 0.4 | 0.4 |
| Evaporation residue (%) | | 58.0 | 50.0 | 99.5 | 99.5 | 42.0 | 40.3 | 39.1 |
| Loss on drying (%) | | 42.0 | 50.0 | 0.5 | 0.5 | 58.0 | 59.7 | 60.9 |
| Ethanol-soluble content (%) | | 57.5 | 32.2 | 99.5 | 99.5 | 23.5 | 22.0 | 21.1 |
| Ignition residue (%) | | 0.1 | 27.0 | 0 | 0 | 27.0 | 27.0 | 27.0 |
| Absorption peak of the infrared absorption spectrum ($cm^{-1}$) | | 1024, 1741, 2854, 2924, 3000, –3500 | 1024, 1724, 2854, 2924, 3000 –3500 | 1024, 1706, 2854, 2924, 3000 –3500 | 1024, 1706, 2854, 2924, 3000 –3500 | 1024, 1724, 2854, 2924, 3000 –3500 | 1024, 1724, 2854, 2924, 3000 –3500 | 1024, 1724, 2854, 2924, 3000 –3500 |

| Test items | | Example product 6 | Example product 7 | Example product 8 | Example product 9 | Example product 10 |
|---|---|---|---|---|---|---|
| Ester value (mg KOH/g) | | 0.1 | 0.1 | 2.0 | 1.5 | 0.8 |
| Hydroxyl value (mg KOH/g) | | 578 | 580 | 582 | 580 | 582 |
| Ether extract content (%) | | 0.5 | 0.2 | 3.0 | 3.0 | 3.0 |
| Constituents of ether extract (%) | C16:0 | 0.050 | 0.020 | 0.300 | 0.300 | 0.300 |
| | C16:0(OH) | 0.001 | 0 | 0.003 | 0.003 | 0.003 |
| | C18:0 | 0.188 | 0.075 | 1.128 | 1.128 | 1.128 |
| | C18:0(OH) | 0.001 | 0 | 0.003 | 0.003 | 0.003 |
| | C18:1 | 0.250 | 0.100 | 1.497 | 1.497 | 1.497 |
| | C18:1(OH) | 0.001 | 0 | 0.003 | 0.003 | 0.003 |
| | C18:2 | 0.011 | 0.004 | 0.066 | 0.066 | 0.066 |
| Hue ($OD_{440}$) | | 0.4 | 0.4 | 0.4 | 0.4 | 0.4 |
| Evaporation residue (%) | | 38.6 | 38.3 | 41.0 | 41.0 | 41.1 |
| Loss on drying (%) | | 61.4 | 61.7 | 59.0 | 59.0 | 58.9 |
| Ethanol-soluble content (%) | | 20.4 | 20.2 | 22.0 | 21.9 | 21.9 |
| Ignition residue (%) | | 27.0 | 27.0 | 27.0 | 27.0 | 27.0 |

Test Example 2

Surfactant Performance Evaluation

The critical micelle concentration (CMC) and surface tension-reducing ability of the SL-containing compositions obtained in the above Reference Production Example 2 and Examples 1 to 10 (crudely purified SL-containing composition-2 and Example products 1 to 10) were measured. For comparative controls, the critical micelle concentration (CMC) and surface tension-reducing ability of commercially available anionic surfactants (A: "Amisoft LT-12" (30%), produced by Ajinomoto Co., Inc., B: "Surfactin Na" (100%), produced by Wako Pure Chemical Industries, Ltd., C: "Lipolan LJ-441" (37%), produced by Lion Corporation), Tween 20 (Polyoxyethylene Sorbitan Monolaurate (20 E.O.)), and SLS (Sodium Lauryl Sulfate) were also measured. Commercially available anionic surfactant A contains N-acyl-L-glutamic acid triethanolamine as a component. Commercially available anionic surfactant B contains sodium surfactin as a component. Commercially available anionic surfactant C contains sodium α-olefin sulfonate as a component.

(1) Experimental Method

The critical micelle concentration (CMC) and surface tension-reducing ability were measured according to the Wilhelmy method. The measurements were performed at pH 7 at 20° C. using a CBVP-Z automatic surface tensiometer (produced by Kyowa Interface Science Co., Ltd.). For pH adjustment, an aqueous sodium hydroxide solution or an aqueous hydrochloric acid solution was used.

(2) Experimental Results

Table 4 shows the measurement results of the critical micelle concentration (CMC) and surface tension-reducing ability of the samples.

TABLE 4

| Sample | Critical micelle concentration (CMC) (ppm) | Surface tension-reducing ability (mN/m) |
| --- | --- | --- |
| Example product 1 | 300 | 38.2 |
| Example product 2 | 300 | 38.0 |
| Example product 3 | 300 | 32.0 |
| Example product 4 | 300 | 32.4 |
| Example product 5 | 300 | 33.0 |
| Example product 6 | 300 | 35.6 |
| Example product 7 | 300 | 37.8 |
| Example product 8 | 300 | 32.1 |
| Example product 9 | 300 | 32.2 |
| Example product 10 | 300 | 32.2 |
| Crudely purified SL-containing composition-2 | 300 | 31.7 |
| Commercially available surfactant A | 1100 | 22.9 |
| Commercially available surfactant B | 12 | 27.4 |
| Commercially available surfactant C | 1000 | 31.7 |
| Tween 20 | 100 | 39.0 |
| SLS | 300 | 34.0 |

Test Example 3

Cytotoxicity Test Using HeLa Cells

Using the SL-containing compositions obtained in the above Reference Production Example 2 and Examples 1 to 10 (crudely purified SL-containing composition-2 and Example products 1 to 10), a cytotoxicity test was performed using HeLa cells. For comparative controls, the above commercially available anionic surfactants A to C, Tween 20, and SLS were also subjected to the cytotoxicity test.

(1) Experimental Method

HeLa cells (Kurabo Industries, Ltd.) were seeded in a 96-well plate to a concentration of $2 \times 10^4$ cells/well and cultured in Dulbecco's Modified Eagle Medium (produced by Nissui Pharmaceutical Co., Ltd.) containing 10% NCS (Newborn Calf Serum: produced by Invitrogen), non-essential amino acids, 58 μg/ml L-glutamic acid, 60 μg/ml kanamycin at 37° C., 5% $CO_2$ for 72 hours. The medium was replaced with media containing the samples. After 48 hours, each medium was replaced with a medium containing 1 mg/ml MTT (3-(4,5-dimethyl-2-thiazolyl)-2,5-diphenyl-2H-tetrazolium bromide). After the treatment was allowed to proceed for 2 hours, formazan dye was extracted with isopropanol. Absorbance at a wavelength of 570 nm was measured. The viability % of the cells was calculated according to the following Formula.

$$\text{Cell viability (\%)} = (A/B) \times 100 \quad \text{(Formula 10)}$$

A: Absorbance ($CD_{570}$) of the cell-seeded medium after 48 hours of treatment with a sample B: Absorbance ($CD_{570}$) of the sample-free cell-seeded medium (2) Experimental Results The cell viability was calculated from the above MTT assay, and the cell lethal concentration ($IC_{50}$) was determined from the obtained cell viability.

FIG. 1 is a graph plotting the cell lethal concentration ($IC_{50}$) calculated from the cell viability versus the CMC calculated in Test Example 1. Table 5 shows the summary of results obtained using each sample regarding CMC (ppm) calculated in Test Example 1, cell lethal concentration ($IC_{50}$), and division value calculated from these two values ($IC_{50}$/CMC).

TABLE 5

| Sample | CMC (ppm) | $IC_{50}$ (ppm) | $IC_{50}$/CMC |
| --- | --- | --- | --- |
| Example product 1 | 300 | 57,000 | 190 |
| Example product 2 | 300 | 60,000 | 200 |
| Example product 3 | 300 | 3,000 | 10 |
| Example product 4 | 300 | 5,100 | 17 |
| Example product 5 | 300 | 12,000 | 40 |
| Example product 6 | 300 | 26,000 | 86.7 |
| Example product 7 | 300 | 48,000 | 160 |
| Example product 8 | 300 | 2,000 | 6.7 |
| Example product 9 | 300 | 3,000 | 10 |
| Example product 10 | 300 | 4,000 | 13.3 |
| Crudely purified SL-containing composition-2 | 300 | 1,500 | 5 |

TABLE 3-continued

| Absorption peak of the infrared absorption spectrum (cm$^{-1}$) | 1024, 1724, 2854, 2924, 3000 –3500 | 1024, 1724, 2854, 2924, 3000 –3500 | 1024, 1724, 2854, 2924, 3000 –3500 | 1024, 1724, 2854, 2924 3000 –3500 | 1024, 1724, 2854, 2924, 3000 –3500 |
| --- | --- | --- | --- | --- | --- |

TABLE 5-continued

| Sample | CMC (ppm) | IC$_{50}$ (ppm) | IC$_{50}$/CMC |
|---|---|---|---|
| Commercially available surfactant A | 1100 | 700 | 0.6 |
| Commercially available surfactant B | 12 | 150 | 12.5 |
| Commercially available surfactant C | 1000 | 120 | 0.1 |
| Tween 20 | 100 | 200 | 2.0 |
| SLS | 300 | <10 | <0.03 |

These results show that Example products 1 to 10 had an IC$_{50}$ of 2,000 to 60,000 ppm, which is significantly higher than the IC$_{50}$ (10 to 700 ppm) of the commercially available surfactants, Tween 20, and SLS; this thus demonstrates that Example products 1 to 10 have significantly low toxicity. Further, the IC$_{50}$ of these Example products is equal to or greater than 1.3 times the IC$_{50}$ (1,500 ppm) of the crudely purified SL-containing composition-2, which was obtained as an intermediate during the production of the Example products. The results confirm that toxic components were significantly removed by the treatment (solvent-extraction treatment, hydrophobic column chromatography) to which the crudely purified SL-containing composition-2 was subjected.

The cytotoxicity test performed in this test is proposed as an alternative to the Draize test (an alternative ocular irritancy test), the Draize test being commonly used as an ocular irritation test for evaluating irritation to the eyes or mucosa (Kenji Okamoto, *Nihon-niokeru ganshigekisei-shiken daitaiho-no doukou* ["Trends in alternative ocular irritation test methods in Japan"], Fragrance Journal 2005-2, pp.67-71; *Daitaiho-wo mochiite keshohingenryo-no gan-shigekisei-wo hyokasuruniatatteno shishin* ["Guidelines for evaluating ocular irritation of cosmetic materials using alternative methods"] (prepared by the Health and Welfare Scientific Research Group) Altern. Animal Test. Experiment, 5 (Supplement), 1998). According to the Ministry of Health and Welfare's proposal described in the latter paper, when a cytotoxicity test is performed using test substances as well as using Tween 20 as a non-irritating standard substance and using SLS as a positive control substance, test substances having an IC$_{50}$ of more than that of Tween 20 can be evaluated to be "substantially non-irritating," and test substances having an IC$_{50}$ of lower than that of Tween 20 but higher than that of SLS can be evaluated to be "mildly irritating" (see Note 8 of the latter paper).

As shown in the above Table, the IC$_{50}$ values of the low-toxicity SL-containing compositions of the present invention obtained in Examples 1 to 10 are significantly greater than the IC$_{50}$ of Tween 20, and are thus determined to be "non-irritating" materials. The IC$_{50}$ values of the low-toxicity SL-containing compositions of the present invention are much greater than the IC$_{50}$ values of the commercially available surfactants. Accordingly, the low-toxicity SL-containing compositions of the present invention are less toxic and less irritating than known surfactants.

Further, the ratio of the IC$_{50}$ to CMC (IC$_{50}$/CMC) of the low-toxicity SL-containing compositions of the present invention is in the range of 6.7:1 to 200:1, and the IC$_{50}$ value is greatly different from CMC. Accordingly, the low-toxicity SL-containing compositions of the present invention were confirmed to fully function as surfactants while ensuring safety (low toxicity and low irritation).

Test Example 4

Cytotoxicity of Higher Fatty Acid and Hydroxy Fatty Acid

The cytotoxicity of a higher fatty acid and a hydroxy fatty acid was measured by using oleic acid as a higher fatty acid contained in a large amount in an SL-containing composition, and using 12-hydroxy stearic acid as a hydroxy fatty acid.

Specifically, oleic acid and 12-hydroxy stearic acid were individually dissolved in 99.5% ethanol to a concentration of 100,000 ppm, and passed through a GHP membrane filter (0.45 µm) (produced by Nihon Pall Manufacturing Ltd.). The filtrates were diluted to a concentration in the range of 1,000 ppm to 50,000 ppm with 99.5% ethanol. 990 µl of 10% NCS medium was added to 10 µl of each of the diluted solutions to prepare cytotoxicity test liquids (liquids having a concentration in the range of 10 to 1,000 ppm). Using these solutions as test liquids, the viability (%) of HeLa cells was determined according to the method described in Test Example 3. The cell lethal concentrations (IC$_{50}$) of oleic acid and 12-hydroxy stearic acid were calculated.

The results show that the cell lethal concentrations (IC$_{50}$) of oleic acid and 12-hydroxy-stearic acid are 300 ppm and 160 ppm, respectively. These IC$_{50}$ values are as small as 1/6 to 1/375 the IC$_{50}$ values (2,000 to 60,000 ppm, see Table 4) of the low-toxicity SL-containing compositions of the present invention (Example products 1 to 10). Accordingly, there is concern that these compounds, if contained in the low-toxicity SL-containing compositions of the present invention, may increase the cytotoxicity of the SL-containing compositions. Conversely, a low-toxicity SL-containing composition can be obtained by preparing an SL-containing composition in such a manner that such higher fatty acids and hydroxy fatty acids having 16 to 18 carbon atoms, and the like are not contained, or contained only in a trace amount.

Test Example 5

Influence of Lactonic SLs on Surfactant Potency

Lactonic SLs were added to a high-purity SL-containing composition having the constituent features shown below to prepare compositions (Example products 11 to 15) containing lactonic SLs in a proportion of 0 to 2 mass % (ester value of the compositions in an amount corresponding to 1 g of the ethanol-soluble content: 0 to 2 mg KOH/g), based the total amount of the acidic SLs, lactonic SLs, fatty acids, and hydroxy fatty acids in the composition taken as 100 mass %.
High-Purity SL-Containing Composition
(1) Acidic SLs: 99.95 mass %, lactonic SLs: 0 mass %, and fatty acids and hydroxy fatty acids (in total): 0.05 mass %, based on the total amount of the acidic SLs, lactonic SLs, fatty acids, and hydroxy fatty acids taken as 100 mass %,
(2) Absorbance at a wavelength of 440 nm (OD$_{440}$) of an aqueous solution prepared by dissolving the composition so that the solution has a concentration of ethanol-soluble content of 10 mass %: 0.08
(3) Hydroxyl value of the composition in an amount corresponding to 1 g of its ethanol-soluble content: 596 mg KOH
(4) HeLa cell lethal concentration (IC$_{50}$): 63,000 ppm The critical micelle concentration (CMC) and surface tension-reducing ability of these SL-containing compositions were measured, and their performance as surfactants (wettability, solubilizing power, detergency, and foamability) was evaluated. The critical micelle concentration (CMC) and surface tension-reducing ability were measured in the same manner as in Test Example 2 according to the Wilhelmy method. Specifically, the measurement was performed at pH 7 at 20° C. using a CBVP-Z automatic surface tensiometer (produced by Kyowa Interface Science Co., Ltd.).

Table 6 shows the results.

TABLE 6

| Sample (Example product) | 11 | 12 | 13 | 14 | 15 |
|---|---|---|---|---|---|
| Proportion of lactonic SL (Ester value) | 0 | 0.1 | 0.8 | 1.5 | 2 |
| Minimum surface tension (mN/m) | 42.1 | 41.5 | 40.8 | 39.9 | 39.9 |
| CMC | 300 | 300 | 300 | 300 | 300 |

Generally, when a nonionic surfactant (lactonic SL is one example thereof) is added to an anionic surfactant (acidic SL is one example thereof), surface tension may increase or decrease, and usually cannot be inferred. In the SL-containing compositions of the present invention, as shown in Table 6, when a nonionic surfactant (lactonic SL) was added in an amount up to a specific level to an anionic surfactant (acidic SL), the surface tension was confirmed to be reduced. Specifically, as the proportion of lactonic SLs increased from 0% to 1.5%, the surface tension (the minimum surface tension) decreased. However, the plateau was at 1.5%; even when lactonic SLs were added in a proportion of more than 1.5%, no change occurred in surface tension.

Surface tension reduction is one of the advantages required of surfactants. The compositions of the present invention containing lactonic SLs at a concentration of up to 2% are expected to have improved performance as a surfactant and achieve effects of enhancing detergency, wettability, solubilizing power, and foamability.

Test Example 6

Preparation and Evaluation of Body Washes (Foaming, Rinsing, and Skin Irritation)

Using the low-toxicity SL-containing composition obtained in Example 1, body washes (body washes 1 to 4 (liquids) of the present invention and body washes 5 and 6 (solids) of the present invention) were produced according to the formulations shown in Table 7. The characteristics (foaming, rinsing, and skin irritation) of each body wash were evaluated. As a comparative test, comparative body washes 1 to 5 (liquids) and comparative body washes 6 and 7 (solids) shown in Table 8, which were produced using the roughly purified SL-containing composition-2 obtained in Reference Production Example 2, were also evaluated for the above characteristics in the same manner.

(1) Experimental Method
(1-1) Foaming and Rinsing

Five subjects claiming to have sensitive skin put body washes shown in Tables 7 and 8 (body washes 1 to 6 of the present invention and comparative wash washes 1 to 7) onto their wet palms. They rubbed their palms together for 30 seconds to evaluate the foaming of the body washes. In this experiment, each liquid wash was used in an amount of 1 ml. Each solid wash was also used in an amount equivalent to 1 ml by rubbing palms together. The hands were rinsed with 40° C. running water with both palms being rubbed together for 30 seconds. The rinsing of each body wash was evaluated. The foaming was evaluated on a four-point scale: A: good foaming; B: foaming; C: slight foaming; D: no foaming. The rinsing was evaluated on a two-point scale: A: no sliminess and no squeakiness; B: either sliminess or squeakiness.

(1-2) Skin Irritation

Each test body wash was diluted with purified water to prepare a 1% test liquid, and 20 µl of each test liquid was applied to a filter paper portion of tape for a skin sensitization test (patch test) (Finn Chambers®, produced by SmartPractice Japan). The prepared tape pieces were applied to an approximate midpoint between the left forearm flexor portion and the wrist of subjects (10 men and women in their twenties to fifties who claimed to have sensitive skin). The tape pieces were allowed to act for 20 minutes and then removed. The arms were left without washing. The evaluation was performed 40 minutes after removing the tape pieces. Subjects who had erythema continued to be observed until the erythema disappeared. At the time of the evaluation, the presence or absence of irritation, such as tingling and prickling, was also investigated.

Forty minutes after removing the tape pieces, the sites of application were observed with the naked eye. The evaluation was made according to the criteria of the Japanese Society for Contact Dermatitis shown in the table below.

TABLE 7

| Criteria for the patch test | |
|---|---|
| Response on the skin | Evaluation |
| No response | − |
| Slight erythema | ± |
| Prominent erythema | + |
| Erythema and edema, papular eczema | ++ |
| Erythema and edema, papular eczema and vesicle | +++ |

The evaluation was made on a four-point scale: −: 0 points; ±: 1 point; +: 2 points; ++: 3 points; +++: 4 points. The scores of each test subject were averaged. The skin irritation was evaluated on a four-point scale, based on the average score: A: 0 to 0.30 points; B: 0.31 to 0.80 points; C: 0.81 to 1.20 points; D: 1.21 points or higher.

(2) Experimental Results

Tables 8 and 9 show the results.

TABLE 8

| | Body wash of the present invention (mass %) | | | | | | |
|---|---|---|---|---|---|---|---|
| | 1 | 2 | 3 | 4 | 5 | 6 | 7 |
| Low-toxicity SL-containing composition (Example 1) | 0.01 | 5.0 | 10.0 | 20.0 | 30.0 | 60.0 | 100 |
| Roughly purified SL-containing composition-2 (Reference Example 2) | — | — | — | — | — | — | — |
| Sodium laureth sulphate | — | — | 5.0 | — | — | — | — |
| Soap base | — | — | — | 5.0 | — | 20.0 | — |
| Glycerol | 5.0 | 5.0 | 5.0 | 5.0 | 5.0 | 5.0 | — |
| pH adjuster (See note 1.) | q.s.* | q.s.* | q.s.* | q.s.* | q.s.* | q.s.* | — |

TABLE 8-continued

| | Body wash of the present invention (mass %) | | | | | | |
|---|---|---|---|---|---|---|---|
| | 1 | 2 | 3 | 4 | 5 | 6 | 7 |
| Purified water | Balance | Balance | Balance | Balance | Balance | Balance | Balance |
| Total | 100.0 | 100.0 | 100.0 | 100.0 | 100.0 | 100.0 | 100.0 |
| pH | 6.0 | 6.0 | 5.5 | 7.0 | 4.0 | 5.0 | 4.0 |
| Foaming | B | B | A | A | A | A | A |
| Rinsing | B | B | B | B | B | B | B |
| Skin irritation | A | A | A | A | A | A | A | note 1.:
pH adjusters: citric acid and sodium citrate
*The amount to be used was adjusted so that the final body wash had the specific pH shown in the table..

TABLE 9

| | Comparative body wash (mass %) | | | | | | |
|---|---|---|---|---|---|---|---|
| | 1 | 2 | 3 | 4 | 5 | 6 | 7 |
| Low-toxicity SL-containing composition (Example 1) | — | — | — | — | — | — | — |
| Roughly purified SL-containing composition-2 (Reference Production Example 2) | 10.0 | — | — | 10.0 | — | — | — |
| Sodium lauryl sulfate | — | 10.0 | 10.0 | 5.0 | 10.0 | — | — |
| Lauramidopropyl betaine | — | — | 5.0 | 5.0 | — | — | — |
| Stearic acid | — | — | — | — | — | — | 20.0 |
| Soap base | — | — | — | — | 5.0 | 80.0 | 60.0 |
| Squalane | — | — | — | — | — | 5.0 | 5.0 |
| Glycerol | 5.0 | 5.0 | 5.0 | 5.0 | 5.0 | 10.0 | 10.0 |
| pH adjuster (See note 1.) | q.s.* | q.s.* | q.s.* | q.s.* | q.s.* | q.s.* | q.s.* |
| Purified water | Balance | Balance | Balance | Balance | Balance | Balance | Balance |
| Total | 100.0 | 100.0 | 100.0 | 100.0 | 100.0 | 100.0 | 100.0 |
| pH | 4.0 | 5.0 | 5.5 | 6.0 | 9.5 | 10.0 | 10.5 |
| Foaming | D | D | C | D | C | D | C |
| Rinsing | D Sliminess | D Sliminess | D Sliminess | D Sliminess | D Sliminess | D Squeakiness | D Squeakiness |
| Skin irritation | C | D | D | D | D | C | C | note 1.:
pH adjusters: citric acid and sodium citrate
*The amount to be used was adjusted so that the final body wash had the specific pH shown in the table.

As is clear from the results of body wash 6 of the present invention, the low-toxicity SL-containing composition of the present invention itself has excellent foaming and rinsing. Furthermore, the low-toxicity SL-containing composition of the present invention has low skin stimulation. This result was the same even when the low-toxicity SL-containing composition of the present invention was used with a surfactant with high skin irritation (sodium laureth sulphate) (body wash 3 of the present invention).

The body wash of the present invention, which contains the low-toxicity SL-containing composition in a very low concentration of 0.01 mass % (body wash 1 of the present invention), also had good foaming and rinsing. The body wash of the present invention containing the low-toxicity SL-containing composition in a high concentration of 10 mass %, or the body wash of the present invention used with a surfactant with poor foaming or poor rinsing (sodium laureth sulphate) also had excellent foaming and good rinsing.

These results show that the use of the low-toxicity SL-containing composition of the present invention as a surfactant can provide a body wash that has good foaming and good rinsing with less skin stimulation.

Test Example 7

Preparation and Evaluation of Hair Wash (Foaming, Rinsing, and Skin Irritation)

Using the low-toxicity SL-containing composition obtained in Example 1, liquid hair washes (pH of 4 to 7; hair washes 1 to 4 of the present invention) were produced according to the formulations shown in the table below, and the characteristics (foaming, rinsing, and skin irritation) of each hair wash were evaluated. As a comparative test, comparative hair washes (pH of 4 to 10) shown in the table below were also evaluated for the above characteristics in the same manner.

(1) Experimental Method
(1-1) Foaming and Rinsing

Five female subjects claiming to have sensitive skin (hair length: approximately to the shoulder level) washed their hair with 6 ml of each of the hair washes shown in the table below (hair washes 1 to 4 of the present invention and comparative hair wash) using 40° C. water. The rinsing was evaluated in terms of foaming and hair squeakiness when rinsing with water. The foaming was evaluated on a four-point scale: A: Good foaming, B: Foaming, C: Slight foaming, C: No foaming. The rinsing was evaluated on a three-point scale: A: No squeakiness, B: Slight squeakiness, C: Some squeakiness.

(1-2) Skin Irritation

The skin irritation was evaluated in the same manner as in Test Example 6.

(2) Experimental Results

The table below shows the results of both experiments.

TABLE 10

|  | Hair wash of the present invention | | | | | Comparative hair wash (mass %) | |
|---|---|---|---|---|---|---|---|
|  | 1 | 2 | 3 | 4 | 5 | 1 | 2 |
| Low-toxicity SL-containing composition (Example 1) | 0.01 | 10.0 | 30.0 | 10.0 | 20.0 | — | — |
| Sodium laureth sulphate | — | — | — | 5.0 | — | 10.0 | — |
| Cocamidopropyl betaine | — | — | — | 5.0 | — | 5.0 | — |
| Soap base | — | — | — | — | 5.0 | — | 30.0 |
| Cationized cellulose | 0.5 | 0.5 | 0.5 | 0.5 | 0.5 | 0.5 | 0.5 |
| pH adjuster (See note 1.) | q.s.* | q.s.* | q.s.* | q.s.* | q.s.* | q.s.* | — |
| Purified water | Balance | Balance | Balance | Balance | Balance | Balance | Balance |
| Total | 100.0 | 100.0 | 100.0 | 100.0 | 100.0 | 100.0 | 100.0 |
| pH | 6.0 | 5.0 | 4.0 | 5.5 | 7.0 | 5.5 | 10.0 |
| Foaming | B | B | A | A | A | D | D |
| Rinsing | B | B | B | B | B | C | D |
| Skin irritation | A | A | A | A | A | D | C | note 1.:
pH adjuster: citric acid and sodium citrate
*The amount to be used was adjusted so that the final hair wash had the specific pH shown in the table.

As is clear from these results, the hair wash of the present invention containing the low-toxicity SL-containing composition in a high concentration of 30 mass % also had extremely low skin irritation (hair wash 3 of the present invention). This extremely low skin irritation was the same even when surfactants with high skin irritation (sodium laureth sulphate and cocamidopropyl betaine) were used together (hair wash 4 of the present invention). The hair wash of the present invention containing the low-toxicity SL-containing composition in a very low concentration of 0.01 mass % (hair wash 1 of the present invention) also had good foaming and good rinsing. The hair wash of the present invention containing the low-toxicity SL-containing composition in a high concentration of 30 mass % (hair wash 3 of the present invention) or the hair wash of the invention used together with surfactants with poor foaming or poor rinsing (sodium laureth sulphate and cocamidopropyl betaine) (hair wash 4 of the present invention) also had excellent foaming and good rinsing. It is generally known that hair washes prepared by incorporating soap have poor foaming and poor rinsing. In contrast, a hair wash prepared by incorporating the low-toxicity SL-containing composition (hair wash 5 of the present invention) had good foaming and good rinsing.

These results show that using the low-toxicity SL-containing composition of the present invention as a surfactant can produce and provide a hair wash with good foaming and good washing with less skin irritation.

Test Example 8

Preparation and Evaluation of Eye Washes (Ocular Mucosa Irritation)

Using the SL-containing composition obtained in Example 2, liquid eye washes (pH of 6; eye washes 1 to 3 of the present invention) were produced according to the formulations shown in Table 11. The ocular mucosa irritation of each eye wash was evaluated. As a comparative test, ocular mucosa irritation of comparative eye washes 1 and 2 (pH of 6) shown in Table 11 was also evaluated in the same manner.

(1) Experimental Method: (Ocular Mucosa Irritation Assessment)

A cytotoxicity test has been proposed as a substitute method for the ocular mucosa irritation test for evaluating stimulation to the eyes and mucosa. Accordingly, the cytotoxicity test was performed using Seruminstitut rabbit corneal (SIRC) cells. First, 100 μL of each eye wash serially diluted in MEM medium was added to a 96-well plate. The SIRC cells were seeded to a concentration of $1 \times 10^4$ cells/well and cultured at 37° C., 5% $CO_2$ for 72 hours. After the culture, the medium was replaced with a medium containing 0.5 mg/mL MTT and further cultured for another 2 hours. Formazan (dye) was extracted from the obtained culture using isopropanol. The absorbance at 570 nm was measured. The cell viability (%) was calculated according to the following formula.

Cell viability (%)=$(A/B) \times 100$

A: Absorbance ($OD_{570}$) of cells treated with medium containing the eye wash

B: Absorbance ($OD_{570}$) of cells treated with medium not containing the eye wash The test was performed in the same manner using triethanolamine (TEA) as a comparative control substance (Comparative Test). Each eye wash obtained above was evaluated according to the following criteria:

A: The cell viability (%) was higher than that obtained in the comparative test (i.e., the cytotoxicity was lower than TEA).

B: The cell viability (%) was at an equivalent level (i.e., the cytotoxicity was equivalent to that of TEA).

C: The cell viability (%) was lower than that obtained in the comparative test (i.e., the cytotoxicity was higher than TEA).

(2) Experimental Results

Table 11 shows the results.

TABLE 11

|  | Eye wash of the present invention | | | Comparative eye wash (mass %) | |
|---|---|---|---|---|---|
|  | 1 | 2 | 3 | 1 | 2 |
| Low-toxicity SL-containing composition (Example 2) | 0.001 | 1.0 | 10 | — | — |
| POE hydrogenated castor oil | — | — | — | 1.0 | — |
| Polysorbate 80 | — | — | — | — | 1.0 |
| Sodium chloride | 0.4 | 0.4 | 0.4 | 0.4 | 0.4 |

TABLE 11-continued

|  | Eye wash of the present invention | | | Comparative eye wash | | (mass %) |
|---|---|---|---|---|---|---|
|  | 1 | 2 | 3 | 1 | 2 | |
| Boric acid | 0.5 | 0.5 | 0.5 | 0.5 | 0.5 | |
| Borax | 0.1 | 0.1 | 0.1 | 0.1 | 0.1 | |
| pH adjusting agents (See Note 1.) | q.s.* | q.s.* | q.s.* | q.s.* | q.s.* | |
| Purified water | Balance | Balance | Balance | Balance | Balance | |
| Total | 100.0 | 100.0 | 100.0 | 100.0 | 100.0 | |
| Ocular mucosa irritation | A | A | A | C | C | |

Note 1.:
pH adjusting agent: sodium hydroxide
*The amount to be added was adjusted so that the final eye wash had a pH of 6.

As is clear from the above results, the eye wash of the present invention containing the low-toxicity SL-containing composition in a high concentration of 10 mass % (eye wash 3 of the present invention) also had extremely low ocular mucosa irritation. The results confirmed that the eye wash containing the low-toxicity SL-containing composition even in an extremely low concentration of 0.001% (eye wash 1 of the present invention) had good cleaning power.

These results show that using the low-toxicity SL-containing composition of the present invention as a surfactant can produce and provide an eye wash with a good cleaning power and low ocular mucosa irritation.

Test Example 9

Preparation and Evaluation of Eye Drop (Ocular Irritation)

Using the SL-containing composition obtained in Example 5, liquid eye drops (pH of 6) (eye drops 1 to 3 of the present invention) were produced according to the formulations shown in Table 12. Each eye drop was evaluated for eye irritation. As a comparative test, comparative eye drops 1 and 2 (pH of 6) shown in Table 12 were also evaluated for ocular mucosa irritation in the same manner.
(1) Experimental Method
(1-1) Ocular Mucosa Irritation
Using eye drops 1 to 3 of the present invention and comparative eye drops 1 to 2 of the present invention as test samples, the cytotoxicity test was performed using Seruminstitut rabbit corneal (SIRC) cells in the same manner as in Test Example 8.
(2) Experimental Results
Table 12 shows the results.

TABLE 12

|  | Eye drop of the present invention | | | Comparative eye drop | | (mass %) |
|---|---|---|---|---|---|---|
|  | 1 | 2 | 3 | 1 | 2 | |
| Low-toxicity SL-containing composition (Example 5) | 0.001 | 5.0 | 10.0 | — | — | |
| POE hydrogenated castor oil | — | — | — | 0.5 | — | |

TABLE 12-continued

|  | Eye drop of the present invention | | | Comparative eye drop | | (mass %) |
|---|---|---|---|---|---|---|
|  | 1 | 2 | 3 | 1 | 2 | |
| Polysorbate 80 | — | — | — | — | 0.5 | |
| L-Menthol | 0.01 | 0.01 | 0.01 | 0.01 | 0.01 | |
| D-camphor | 0.005 | 0.005 | 0.005 | 0.005 | 0.005 | |
| Boric acid | 1.0 | 1.0 | 1.0 | 1.0 | 0.5 | |
| Boric acid | 0.05 | 0.05 | 0.05 | 0.05 | 0.05 | |
| Hydrochloric acid | q.s.* | q.s.* | q.s.* | q.s.* | q.s.* | |
| Sodium hydroxide | q.s.* | q.s.* | q.s.* | q.s.* | q.s.* | |
| Purified water | Balance | Balance | Balance | Balance | Balance | |
| Total | 100.0 | 100.0 | 100.0 | 100.0 | 100.0 | |
| Ocular mucosa irritation | A | A | A | C | C | |

*The amount to be used was adjusted so that the final eye drop had a pH of 6.0.

As is clear from the above results, the eye drop of the present invention containing the low-toxicity SL-containing composition in a high concentration of 10 mass % had extremely low ocular mucosa irritation (eye drop 3 of the present invention), as with the eye wash evaluated in Test Example 8. The results show that that using the low-toxicity SL-containing composition of the present invention as a surfactant can produce and provide an eye drop with low ocular mucosa irritation.

Test Example 10

Preparation and Evaluation of Mouthwashes (Mucosal Irritation)

Using the SL-containing composition obtained in Example 9, liquid mouthwashes (pH of 6.5) (mouthwashes 1 to 3 of the present invention) were produced according to the formulations shown in Table 13. Each mouthwash was evaluated for oral mucosa irritation. As a comparative test, comparative mouthwashes 1 to 3 (pH of 6.5) shown in Table 13 were also evaluated for oral mucosa irritation in the same manner.
(1) Experimental Method (Oral Mucosa Irritation)
Using mouthwashes 1 to 3 of the present invention and comparative mouthwashes 1 to 3 as test samples, a cytotoxicity test was performed using Seruminstitut rabbit corneal (SIRC) cells in the same manner as in Test Example 8.
(2) Experimental Results
Table 13 shows the results.

TABLE 13

|  | Mouthwash of the present invention | | | Comparative mouthwash | | | (mass %) |
|---|---|---|---|---|---|---|---|
|  | 1 | 2 | 3 | 1 | 2 | 3 | |
| Low-toxicity SL-containing composition (Example 2) | 0.001 | 1.0 | 10.0 | — | — | — | |
| Crudely purified SL containing composition-2 (Comparative Production Example 2) | — | — | — | 5.0 | — | — | |

TABLE 13-continued

|  | Mouthwash of the present invention | | | Comparative mouthwash | | | (mass %) |
|---|---|---|---|---|---|---|---|
|  | 1 | 2 | 3 | 1 | 2 | 3 | |
| POE hydrogenated castor oil | — | — | — | — | 1.0 | — | |
| Cetyl-pyridinium chloride | 0.05 | 0.05 | 0.05 | 0.05 | 0.05 | 0.05 | |
| Glycerol | 5.0 | 5.0 | 5.0 | 5.0 | 5.0 | 5.0 | |
| Xylitol | 2.0 | 2.0 | 2.0 | 2.0 | 2.0 | 2.0 | |
| pH adjusting agent (See Note 1.) | q.s.* | q.s.* | q.s.* | q.s.* | q.s.* | q.s.* | |
| Purified water | Balance | Balance | Balance | Balance | Balance | Balance | |
| Total | 100.0 | 100.0 | 100.0 | 100.0 | 100.0 | 100.0 | |
| Oral mucosa irritation | A | A | A | C | D | D | |

Note 1.:
pH adjusting agents: citric acid and sodium citrate
*The amount to be used was adjusted so that the final oral mouthwash had a pH of 6.5.

As is clear from the above results, the mouthwash of the present invention containing the low-toxicity SL-containing composition in a high concentration of 10 mass % had extremely low oral mucosa irritation (mouthwash 3 of the present invention). The results also confirmed that the mouthwash of the present invention containing the low-toxicity SL-containing composition in a very low concentration of 0.001 mass % (mouthwash 1 of the present invention) had good cleaning power.

These results show that using the low-toxicity SL-containing composition of the present invention as a surfactant can produce and provide a mouthwash with good cleaning power and low oral mucosa irritation.

Test Example 11

Preparation and Evaluation of Mucosal Washes (Mucosal Irritation)

Using the SL-containing composition obtained in Example 1, liquid mucosa washes (pH of 6) (mucosa washes 1 to 4 of the present invention) were produced according to the formulations shown in Table 14 below. Each mucosal wash was evaluated for rinsing and mucosal irritation. As a comparative test, comparative mucosal washes 1 and 2 (pH of 6) shown in Table 14 were also evaluated for rinsing and mucosal irritation in the same manner.

(1) Experimental Method
Mucosal Irritation

Using mucosal washes 1 to 4 of the present invention and comparative mucosal washes 1 to 2 as test samples, a cytotoxicity test was performed using Seruminstitut rabbit corneal (SIRC) cells in the same manner as in Test Example 8.

(2) Experimental Results
Table 14 shows the results.

TABLE 14

|  | Mucosal wash of the present invention | | | | Comparative mucosal wash | | (mass %) |
|---|---|---|---|---|---|---|---|
|  | 1 | 2 | 3 | 4 | 1 | 2 | |
| Low-toxicity SL-containing composition (Example No.) | 0.001 | 5.0 | 30.0 | 5.0 | — | — | |
| Crudely purified SL-containing composition-2 (Comparative Production Example 2) | — | — | — | — | 10.0 | — | |
| Acyl fatty acid glutamic acid TEA | — | — | — | 1.0 | 1.0 | 5.0 | |
| Alkyl glucoside | — | — | — | 1.0 | — | 5.0 | |
| Glycerol | 5.0 | 5.0 | 5.0 | 5.0 | — | 2.0 | |
| pH adjusting agents (See Note 1.) | q.s.* | q.s.* | q.s.* | q.s.* | q.s.* | q.s.* | |
| Purified water | Balance | Balance | Balance | Balance | Balance | Balance | |
| Total | 100.0 | 100.0 | 100.0 | 100.0 | 100.0 | 100.0 | |
| Mucosal irritation | A | A | A | A | C | D | |

Note 1.:
pH adjusting agents: citric acid and sodium citrate
*The amount to be used was adjusted to that the final mucosal wash had a pH of 6.

As is clear from the above results, the mucosal wash of the present invention containing the low-toxicity SL-containing composition in a high concentration of 30 mass % (mucosal wash 3 of the present invention) had extremely low mucosal irritation. The results also confirmed that the mucosal wash of the present invention containing the low-toxicity SL-containing composition in an extremely low concentration of 0.001 mass % (mucosal wash 1 of the present invention) had good cleaning power.

These results confirm that using the low-toxicity SL-containing composition of the present invention as a surfactant can produce and provide a mucosal wash with good cleaning power and low mucosal irritation.

Test Example 12

Production and Evaluation of Wound Cleansers (Cleaning Power and Wound Irritation)

Using the SL-containing composition obtained in Example 4, liquid wound cleansers (pH of 5.5) were prepared according to the formulations shown in Table 15 (wound washes 1 to 4 of the present invention). Each cleanser was evaluated for cleaning power and wound irritation. As a comparative test, comparative wound cleansers 1 to 2 shown in Table 15 (pH of 5.5) were also evaluated for cleaning power and wound irritation in the same manner.

(1) Experimental Method
(1-1) Cleaning Power

The cleaning power was evaluated according to the following method. Test pieces were prepared by spreading a "model stain" (see the table below) evenly on stainless steel pieces that were weighed beforehand. The model stain was dried and weighed. After each wound wash (wound washes 1 to 4 of the present invention and comparative would washes 1 and 2) was applied to the dirt surface, the test pieces were allowed to stand for 5 minutes and washed with water for 10 seconds. The test pieces after drying were measured, and the cleaning power percentage was calculated from the ratio of the weight of the model stain before washing to the weight after washing.

The cleaning power was evaluated from the obtained cleaning power percentage according to the following criteria.

Cleaning Power

A: 75 to 100% cleaning power,
B: 50 to 74% cleaning power,
C: 25 to 49% cleaning power,
D: 0 to 24% cleaning power.

Model Stain

Model sebum stain and model blood stain were mixed at a ratio of 5:1 and used as a model stain.

Composition of Model Sebum

| | |
|---|---|
| Macadamia nut oil | 40% |
| Isopropyl myristate | 20% |
| Palmitic acid | 15% |
| Squalene | 10% |
| Oleic acid | 10% |
| Cholesterol | 5% |

Composition of Model Blood

Sterilized, defibrinated sheep blood (1-2) Wound Irritation

The cytotoxicity was evaluated using fibroblasts. First, fibroblasts were seeded in a 96-well plate to a concentration of $1\times10^4$ cells/well, and cultured in DMEM medium at 37° C., 5% $CO_2$ for 72 hours. The medium was replaced with DMEM medium containing wound washes (washes 1 to 4 of the present invention and comparative would washes 1 and 2) in an appropriate concentration, and cultured at 37° C., 5% $CO_2$ for 48 hours. After the culture, the medium was replaced with a medium containing MTT and the culture was continued for another 2 hours. Formazan (dye) was extracted from the obtained culture using isopropanol, and the absorbance was measured at 570 nm. The cell viability was obtained according to the following formula.

Cell viability (%)=(A/B)×100

A: Absorbance ($OD_{570}$) of cells treated with medium containing the wound wash
B: Absorbance ($OD_{570}$) of cells treated with medium not containing the wound wash A test was performed in the same manner using triethanolamine (TEA) as a comparative control substance (Comparative Test). The evaluation was made according to the following criteria: A: the cell viability (%) was higher than that obtained in the comparative test (i.e., the cytotoxicity was lower than TEA); B: the cell viability (%) was at an equivalent level (i.e., the cytotoxicity was equivalent to that of TEA); C: the cell viability (%) was lower than that obtained in the comparative test (i.e., the cytotoxicity was higher than TEA).

(2) Experimental Results

Table 15 shows the results.

TABLE 15

| | Wound wash of the present invention | | | | Comparative wound wash (mass %) | |
|---|---|---|---|---|---|---|
| | 1 | 2 | 3 | 4 | 1 | 2 |
| Low-toxicity SL-containing composition (Example 4) | 0.001 | 5.0 | 10.0 | 30.0 | — | — |
| Roughly purified SL-containing composition-2 (Comparative Production Example 2) | — | — | — | — | 10.0 | — |
| Polysorbate 20 | — | — | — | — | — | 5.0 |
| Glycerol | 5.0 | 5.0 | 5.0 | 5.0 | 5.0 | 5.0 |
| Dipotassium glycyrrhizinate | 0.2 | 0.2 | 0.2 | 0.2 | 0.2 | 0.2 |
| pH adjusting agents (See Note 1.) | q.s.* | q.s.* | q.s.* | q.s.* | q.s.* | q.s.* |
| Purified water | Balance | Balance | Balance | Balance | Balance | Balance |
| Total | 100.0 | 100.0 | 100.0 | 100.0 | 100.0 | 100.0 |
| Cleaning power | B | B | A | A | C | D |
| Wound irritation | A | A | A | A | D | D |

Note 1.:
pH adjusting agents: citric acid and sodium citrate
*The amount to be used was adjusted so that the final would wash had a pH of 5.5.

As is clear from the above results, the wound wash containing the low-toxicity SL-containing composition of the present invention in a concentration of 30 mass % (wound wash 3 of the present invention) had an extremely low wound irritation. The results also confirmed that the wound wash of the present invention containing the low-toxicity SL-containing composition even in an extremely low concentration of 0.001 mass % (wound wash 1 of the present invention) had good cleaning power.

These results show that using the low-toxicity SL-containing composition of the present invention as a surfactant can produce and provide a wound wash with good cleaning power and low wound irritation.

Test Example 13

Preparation and Evaluation of Wound Dressings (Irritation and Dispersibility)

Using the SL-containing composition obtained in Example 6, wound dressing gels (pH of 7) (wound dressing 1 to 8) were prepared according to the formulations shown in Table 16. Each wound dressing was evaluated for wound irritation and dispersibility. As a comparative test, comparative wound dressings (pH of 7) shown in Table 17 were also evaluated for wound irritation and dispersibility in the same manner.

(1) Experimental Method (1-1) Wound Irritation

As test samples, wound dressings 1 to 8 of the present invention and comparative wound dressings 1 to 4 were used. A cytotoxicity test using fibroblasts was performed in the same manner as in Test Example 12 to evaluate wound irritation.

(1-2) Dispersibility

Whether the components dissolved homogeneously during the production of wound dressings 1 to 8 of the present invention and comparative wound dressings 1 to 4 was evaluated on a two-point scale: A: the components homogenously dissolved; B: the components did not dissolve homogenously.

(2) Experimental Results

Tables 16 and 17 show the results.

TABLE 16

| | Wound dressing of the present invention (mass %) | | | | | | | |
|---|---|---|---|---|---|---|---|---|
| | 1 | 2 | 3 | 4 | 5 | 6 | 7 | 8 |
| Low-toxicity SL-containing composition (Example 6) | 0.01 | 0.5 | 1.0 | 5.0 | 0.01 | 0.5 | 1.0 | 10.0 |
| Lactoferrin | 0.5 | 0.5 | — | — | 0.5 | 0.5 | — | — |
| Tretinoin tocoferil | — | — | 0.25 | 0.25 | — | — | 0.25 | 0.25 |
| Carboxymethyl cellulose | 50 | 50 | 50 | 50 | — | — | — | — |
| Collagen | — | — | — | — | 50 | 50 | 50 | 50 |
| Purified water | Balance | Balance | Balance | Balance | Balance | Balance | Balance | Balance |
| Total | 100.0 | 100.0 | 100.0 | 100.0 | 100.0 | 100.0 | 100.0 | 100.0 |
| Irritation | A | A | A | A | A | A | A | A |
| Dispersibility | B | B | B | B | B | B | B | B |

TABLE 17

| | Comparative wound dressing (mass %) | | | | |
|---|---|---|---|---|---|
| | 1 | 2 | 3 | 4 | 5 |
| Low-toxicity SL-containing composition (Example 6) | — | — | — | — | — |
| sodium deoxycholate | 0.3 | — | — | — | — |
| Lactoferrin | 0.5 | 0.5 | 0.5 | — | — |
| Tretinoin tocoferil | — | — | — | 0.25 | 0.25 |
| Carboxymethyl cellulose | 50 | 50 | 80 | — | — |
| Collagen | — | — | — | 50 | 80 |
| Purified water | Balance | Balance | Balance | Balance | Balance |
| Total | 100.0 | 100.0 | 100.0 | 100.0 | 100.0 |
| Irritation | D | C | C | C | C |
| Dispersibility | D | D | D | D | D |

As is clear from the above, the wound dressings of the present invention containing the low-toxicity SL-containing composition have significantly lower irritation than the wound dressings not containing the low-toxicity SL-containing composition (wound dressings 1 to 8 of the present invention), and also had good dispersibility.

These results show that using the low-toxicity SL-containing composition of the present invention can enhance the dispersibility of components and also reduce or inhibit irritation caused by additives, such as surfactants and antimicrobial agents, so that wound dressings with low irritation can be produced and provided.

Test Example 14

Evaluation of the Low-toxicity SL-containing Composition for Moisturizing Effect and Skin Barrier Function-improving Effect Using the low-toxicity SL-containing composition obtained in Example 1, test samples (lotions 1 to 3 of the present invention) were produced according to the formulations shown in Table 18. Each lotion was evaluated for moisturizing and skin barrier function improvement. As a comparative test, comparative lotions 1 to 3 shown in Table 18 were also evaluated for moisturizing and skin barrier function improvement in the same manner.

(1) Experimental Method
(1-1) Moisturizing

An inside portion on upper arms of human subjects was marked and the water content of the stratum corneum was measured with a stratum corneum water content meter (Corneometer CM825, produced by Courage+Khazaka) (initial value). Lotions (lotions 1 to 3 of the present invention and comparative lotions 1 to 3) were applied in an amount of 20 µL/cm² to the site at which the first measurement was performed. After the inside of the naked upper arms was exposed to a room environment at a relative humidity of 50% and a temperature of 20° C. for 4 hours, the water content of stratum corneum at the site to which each lotion was applied was measured. The change in water content between before and after application of the lotion was calculated, and the moisturizing effect of each lotion was evaluated according to the following criteria.

Moisturizing
A: The change in water content of stratum corneum (%) was 120% or more.
B: The change in water content of stratum corneum (%) was 100% to less than 120%.
C: The change in water content of stratum corneum (%) was 90% to less than 100%.
D: The change in water content of stratum corneum (%) was less than 90%.

(1-2) Skin Improvement

Rough skin was artificially produced by keeping the inside portion of the human upper arm in contact with a 5% SDS solution for 1 hour. The texture of the rough skin was observed under a microscope (VHX-1000-VH-220R microscope (produced by Keyence Corporation). The transepidermal water loss was also measured using a Tewameter TM 300 (produced by Courage+Khazaka). Each lotion (lotions 1 to 3 of the present invention and comparative lotions 1 to 3) was applied to the site of measurement in an amount of 20 µL/cm² twice a day. After this operation was performed for 4 days, the skin texture was observed. The transepidermal water loss was measured using a Tewameter TM 300 (produced by Courage+Khazaka). The change (%) in texture before and after application of each lotion was determined. The skin barrier function improvement of each lotion was evaluated according to the following criteria.

Skin barrier Function Improvement
A: The change in water loss was less than 80%.
B: The change in water loss was 80 to less than 90%.
C: The change in water loss was 90 to less than 100%.
D: The change in water loss was 100% or more.

Texture of the Skin
A: The skin texture returned to normal.
B: The skin texture was slightly improved.
C: The skin texture hardly changed.
D: The skin texture deteriorated.

(2) Experimental Results

Table 18 shows the results. FIG. 1 shows microscopic images of the skin after treatment with the 5% SDS solution and of the skin after 4 days of application of the lotion of the present invention.

TABLE 18

|  | Lotion of the present invention | | | Comparative lotion (mass %) | | |
|---|---|---|---|---|---|---|
|  | 1 | 2 | 3 | 1 | 2 | 3 |
| Low-toxicity SL-containing composition (Example 1) | 1 | 10 | 30 | — | — | — |
| Glycerol | — | — | — | — | — | 5 |
| Sucrose fatty acid ester | — | — | — | — | 10 | — |
| Water | 99 | 90 | 70 | 100 | 90 | 95 |
| Moisturizing | A | A | A | D | D | A |
| Skin barrier function improvement | B | A | A | D | D | C |
| Skin texture | B | A | A | D | C | C |

These results show that the low-toxicity SL-containing composition not only has low irritation but also moisturizes the skin and improves skin barrier function. In particular, the lotion containing the low-toxicity SL-containing composition in an amount of 10 mass % has excellent moisturization as well as providing an improved skin barrier function. Accordingly, the results indicate that using the low-toxicity SL-containing composition of the present invention can produce low-irritation external agents (cosmetics, skin drugs, skin quasi-drugs) having good moisturizing and an improved skin barrier function.

Test Example 16

Evaluation of Lotions for Moisturizing and Irritation

Using the low-toxicity SL-containing composition obtained in Example 1, lotions (pH of 5.0) were produced according to the formulations shown in Table 19 (lotions 1 to 3 of the present invention). Each lotion was evaluated for moisturizing and irritation. As a comparative test, comparative lotions 1 to 3 (pH of 5.0) shown in Table 19 were also evaluated for moisturizing and irritation in the same manner.

(1) Experimental Method (1-1) Evaluation of Moisturizing Effect and Stinging

An expert panel of five people applied lotions (lotions 1 to 3 of the present invention and comparative lotions 1 to 3) to their faces after face washing, and evaluated the lotions for moisture and stinging (irritating sensation). The moisture was evaluated on a four-point scale: A: moisture; B: slight moisture; C: poor moisture; and D: no moisture. Stinging (irritating sensation) was evaluated on a three-point scale: A: no irritation; B: slight irritation; C: considerable irritation.

(1-2) Irritation (a) Skin Irritation

Using lotions 1 to 3 of the present invention and comparative lotions 1 to 3, a patch test was performed on 10 subjects in the same manner as in Test Example 6 to evaluate skin irritation of each lotion.

(2) Experimental Results

Table 19 shows the results.

TABLE 19

|  | Lotion of the present invention | | | Comparative lotion (mass %) | | |
|---|---|---|---|---|---|---|
|  | 1 | 2 | 3 | 1 | 2 | 3 |
| Low-toxicity SL-containing composition (Example 1) | 0.01 | 10.0 | 20.0 | — | — | — |
| Crudely purified SL-containing composition-2 (Comparative Production Example 2) | — | — | — | 0.5 | — | — |
| Polyoxyethylene hydrogenated castor oil | — | — | — | — | 0.5 | — |
| Polysorbate 80 | — | — | — | — | — | 0.5 |
| Glycerol | 5.0 | 5.0 | 5.0 | 5.0 | 5.0 | 5.0 |
| Sodium hyaluronate | 0.1 | 0.1 | 0.1 | 0.1 | 0.1 | 0.1 |
| pH adjusting agents (See Note 1.) | q.s.* | q.s.* | q.s.* | q.s.* | q.s.* | q.s.* |
| Purified water | Balance | Balance | Balance | Balance | Balance | Balance |
| Total | 100 | 100 | 100 | 100 | 100 | 100 |
| Moisture retention (moisture) | B | A | A | D | D | D |
| Skin irritation (patch test) | A | A | A | C | D | D |
| Stinging | B | B | B | C | D | D |

Note 1.:
pH adjusting agents: Lactic acid and sodium lactate
*The amount to be used was adjusted so that the final lotion had a pH of 5.

The results confirmed that the lotions of the present invention containing the low-toxicity SL-containing composition in a high concentration of 10 mass % or 20 mass % (lotions 2 and 3 of the present invention) have very low skin irritation, and do not reduce, but instead increase moisturization of glycerol and sodium hyaluronate.

These results show that using the low-toxicity SL-containing composition as a surfactant can produce and provide a cosmetic with good moisturization and low skin irritation.

Test Example 16

Evaluation of Skin-whitening Creams for Irritation and Storage Stability

Using the low-toxicity SL-containing composition obtained in Example 1, skin-whitening creams (pH of 5; creams 1 to 4 of the present invention) were prepared according to the formulations shown in Table 20. The creams were evaluated for storage stability, skin irritation, and feel in use. As a comparative test, comparative creams 1 and 2 (pH of 5) shown in Table 20 were also evaluated for stability, skin irritation, and feel in use in the same manner.

Each cream was produced in the following manner. First, components of phase A and components of phase B were separately mixed and heated to 70° C. After the dissolution by heating, phase B was gradually added to phase A with stirring. The mixture was emulsified using a homomixer. Subsequently, the mixture was allowed to cool to room temperature while stirring.

(1) Experimental Method
(1-1) Evaluation of Storage Stability

Skin-whitening creams (creams 1 to 4 of the present invention, and comparative creams 1 and 2) were stored at room temperature (25±5° C.), 50° C., and −5° C. for 1 month. Changes in cream condition were observed after one month. The evaluation was made on a three-point scale: A: no change; B: slight separation; and C: clear separation.

(1-2) Skin Irritation

Using creams 1 to 4 of the present invention and comparative creams 1 and 2, a patch test was performed on 10 subjects in the same manner as in Test Example 6. Each cream was evaluated for skin irritation.

(1-3) Feel in Use

An expert panel of five people applied skin-whitening creams (creams 1 to 4 of the present invention and comparative creams 1 to 2) to their faces after face washing, and evaluated the creams for feel in use (spreadability, moisture, and skin suitability). Each evaluation was made on a four-point scale: A: excellent, B: good, C: slightly poor, D: poor.

(2) Experimental Results

Table 20 shows the results.

TABLE 20

| | | Skin-whitening cream | | | | | |
| | | Cream of the present invention | | | | Comparative cream | |
| | | 1 | 2 | 3 | 4 | 1 | 2 |
|---|---|---|---|---|---|---|---|
| Phase A | Low-toxicity SL-containing composition (Example 1) | 0.01 | 1.0 | 10.0 | 20.0 | — | — |
| | Crudely purified SL-containing composition-2 (Comparative Production Example 2) | — | — | — | — | 2.0 | — |
| | Polysorbate 60 | — | — | 0.5 | — | — | 2.0 |
| | Ascorbyl tetrahexyldecanoate | 3.0 | 3.0 | 3.0 | 3.0 | 3.0 | 3.0 |
| | Behenyl alcohol | 1.0 | 1.0 | 1.0 | 1.0 | 1.0 | 1.0 |
| | Tocopherol acetate | 0.1 | 0.1 | 0.1 | 0.1 | 0.1 | 0.1 |
| | Squalane | 3.0 | 3.0 | 3.0 | 3.0 | 3.0 | 3.0 |
| Phase B | Glycerol | 5.0 | 5.0 | 5.0 | 5.0 | 5.0 | 5.0 |
| | Citric acid | 0.1 | 0.1 | 0.1 | 0.1 | 0.1 | 0.1 |
| | Purified water | Balance | Balance | Balance | Balance | Balance | Balance |
| | Total | 100 | 100 | 100 | 100 | 100 | 100 |
| Feel in use | Spreadability | A | A | A | A | C | D |
| | Moisture | A | A | A | A | C | D |
| | Skin suitability | B | A | A | A | C | D |
| | Storage stability | B | B | A | B | D | D |
| | Skin irritation | A | A | A | A | D | D |

As is clear from the above results, the skin-whitening creams of the present invention containing the low-toxicity SL-containing composition in a high concentration of 10 mass % or 20 mass % have extremely low skin irritation. All the skin-whitening creams of the present invention had an excellent feel in use. These results show that using the low-toxicity SL-containing composition of the present invention as a surfactant can produce and provide cosmetics with good storage stability and good feel in use with low skin irritation.

Test Example 18

Hair protection and Hair Restoration (1) Test Method
(1-1) Production of Hair Sample (a Bundle of Hair with a Length of 30 cm and a Weight of 10 g)
(i) Healthy Hair After healthy black human hair (30 cm) was immersed in a 10% aqueous solution of sodium alkyl ether sulfate (AES) (pH of 7, room temperature) for 1 minute, the hair was washed with running water and dried with a drier. The resulting hair was used as a healthy hair sample (10 g of a bundle of hair).

(ii) Damaged Hair

After healthy black human hair (30 cm) was bleached with a bleaching agent (a mixture of 6% hydrogen peroxide solution and 2% ammonia at a ratio of 1:2 (w/w), (30° C.) for 30 minutes (bath ratio: hair/bleaching agent=1/10 (w/w)), the hair was washed with running water. Subsequently, the hair was immersed in a buffer (pH 4.0) containing 0.1M citric acid and 0.2M disodium hydrogen phosphate for 5 minutes. After the hair was washed with running water and then immersed in distilled water (room temperature) for 5 minutes, the hair was removed and dried over a drier. This treatment was performed three times. Ten grams of a bundle of hair was used as a hair sample.

(1-2) Test Method

A fluorescein sodium salt (Sigma Batch116K 0094 EC208-253-0) was added as a fluorescent substance to a concentration of 0.08 wt. % to a 1 mass % aqueous solution of the low-toxicity SL-containing composition of the present invention (Example 1) to prepare a test solution. As comparative and control tests, the fluorescent substance was also added to a 2 mass % aqueous solution of Aqulio TXF-875 (produced by Nippon Fine Chemical Co., Ltd.) and water, in place of addition to the low-toxicity SL-containing composition (Example 1), to prepare test solutions. Aqulio TXF-875 retains moisture and is known to promote the permeation of active ingredients. Each of the hair samples (healthy hair and damaged hair) was immersed in these liquids for 30 minutes. The cross-section of each sample hair was then observed under a fluorescent microscope.

(2) Test Result

FIG. 3(A) shows the results of healthy hair. FIG. 3(B) shows the results of damaged hair. These results clearly confirmed that, regardless of whether healthy or damaged hair, the surface of sample hair treated with the low-toxicity SL-containing composition was protected and the test solution penetrated the hair. It can thus be expected that using the low-toxicity SL-containing composition of the present invention can not only protect hair surface with coating but can also restore damaged hair through penetration into the hair.

Formulation Example

The formulations of drugs and quasi-drugs containing a low-toxicity SL-containing composition of the present invention are as follows.

The formulations of various products containing a low-toxicity SL-containing composition of the invention are as follows.

Formulation Example 1

Oil Cleansing Agent

| | |
|---|---|
| Polyglyceryl-6 myristate | 12.0 (mass %) |
| Polyglyceryl-6 oleate | 2.0 |
| Polyglyceryl-10 laurate | 2.0 |
| Polyglyceryl-10 pentaisostearate | 4.0 |
| Lauric acid | 2.0 |
| Ethylhexyl palmitate | 10.0 |
| Triethylhexanoyne | 45.0 |
| Low-toxicity SL-containing composition (Examples 1 to 10) | 5.0 |
| Butylene glycol | 10.0 |
| Purified water | Balance |
| Total amount | 100.0 mass % |

Formulation Example 2

Out Bath Treatment

| | |
|---|---|
| Ethanol | 5 (mass %) |
| Starch hydroxypropyltrimonium chloride | 0.3 |
| Low-toxicity SL-containing composition (Examples 1 to 10) | 1 |
| Purified water | Balance |
| Total amount | 100.0 mass % |

Formulation Example 3

Eye Drop (pH 6.6)

| | |
|---|---|
| 1-Menthol | 0.02 (mass %) |
| D-Camphor | 0.001 |
| D-Borneol | 0.005 |
| Eucalyptus oil | 0.01 |
| Mint oil | 0.002 |
| Naphazoline hydrochloride | 0.0015 |
| Neostigmine methylsulfate | 0.004 |
| Chlorpheniramine maleate | 0.03 |
| Pyridoxine hydrochloride | 0.08 |
| Tocopherol acetate | 0.04 |
| L-Aspartic acid magnesium potassium | 1.4 |
| Aminoethylsulfonic acid | 0.8 |
| Boric acid | 0.5 |
| Borax | 0.1 |
| Benzalkonium chloride concentrated solution 50 (Japanese Pharmacopoeia) | 0.015 |
| Chlorobutanol | 0.2 |
| Low-toxicity SL-containing composition (Examples 1 to 10) | 0.3 |
| Hydrochloric acid/Sodium hydroxide | q.s. |
| Purified water | balance |
| Total | 100.00 mass % |

Formulation Example 4

Eyewash (pH 5.8)

| | |
|---|---|
| 1-Menthol | 0.01 (mass %) |
| Epsilon-aminocaproic acid | 0.1 |
| Glycyrrhizinate dipotassium | 0.1 |
| Zinc sulfate | 0.05 |
| Chlorpheniramine maleate | 0.003 |
| Potassium L-aspartate | 0.1 |
| Calcium chloride | 0.05 |
| Boric acid | 1.5 |
| Borax | 0.015 |
| Benzalkonium chloride concentrated solution 50 (Japanese Pharmacopoeia) | 0.004 |
| Chlorobutanol | 0.2 |
| Low-toxicity SL-containing composition (Examples 1 to 10) | 0.2 |

-continued

| | |
|---|---|
| Ethanol | 0.1 |
| Hydrochloric acid/sodium hydroxide | 0.01 |
| Purified water | Balance |
| Total | 100.00 mass % |

Formulation Example 5

Contact Lens Fitting Liquid (pH 7.0)

| | |
|---|---|
| 1-Menthol | 0.015 (mass %) |
| Aminoethylsulfonic acid | 0.5 |
| Potassium chloride | 0.08 |
| Sodium chloride | 0.15 |
| Boric acid | 0.9 |
| Borax | 0.2 |
| Potassium sorbate | 0.1 |
| Disodium edetate (Japanese Pharmacopoeia) | 0.05 |
| Low-toxicity SL-containing compositioin (Examples 1 to 10) | 0.5 |
| Hydrochloric acid/sodium hydroxide | q.s. |
| Purified water | Balance |
| Total | 100.0 mass % |

Formulation Example 6

Contact Lens Fitting Liquid (pH 7.5)

| | |
|---|---|
| 1-Menthol | 0.01 (mass %) |
| Potassium chloride | 0.05 |
| Sodium chloride | 1 |
| Disodium hydrogen phosphate | 0.15 |
| Sodium dihydrogen phosphate | 0.01 |
| Low-toxicity SL-containing composition (Examples 1 to 10) | 0.02 |
| 20% polyhexamethylene biguanide solution (trade name: Cosmosil CQ) | 0.0005 |
| Hydrochloric acid/sodium hydroxide | q.s. |
| Purified water | Balance |
| Total | 100.0 mass % |

Formulation Example 7

Wound Cleanser (pH 6.5)

| | |
|---|---|
| Sodium chloride | 0.9 (mass %) |
| Low-toxicity SL-containing composition (Examples 1 to 10) | 0.05 |
| Hydrochloric acid/sodium hydroxide | q.s. |
| Purified water | Balance |
| Total | 100.0 mass % |

INDUSTRIAL APPLICABILITY

The production method and the toxicity reduction method according to the present invention can produce a low-toxicity SL-containing composition in a simple manner with safety and less energy. The low-toxicity SL-containing composition of the present invention, which is less toxic to cells and also less irritating, is suitable for use not only in foods or beverages but also in cosmetics, drugs, or quasi-drugs, which are externally applied (e.g., applied to wound sites) or applied to the mucosa.

The invention claimed is:

1. A low-toxicity sophorolipid-containing composition comprising at least a coloring component, an acidic sophorolipid, a fatty acid, and a hydroxy fatty acid that are derived from an SL-producing yeast culture,
the following components being in the following proportions, in terms of dry weight, based on the total amount of the acidic sophorolipid, a lactonic sophorolipid, the fatty acid, and the hydroxy fatty acid in the composition taken as 100 mass %:
(1) acidic sophorolipid: not less than 94 mass % and less than 99.99 mass %,
(2) lactonic sophorolipid: more than 0% but not more than 2 mass %, and
(3) fatty acid and hydroxy fatty acid in total: 0.01 to 4 mass %.

2. The low-toxicity sophorolipid-containing composition according to claim 1, wherein the proportion of the lactonic sophorolipid and the total proportion of the fatty acid and hydroxy fatty acid satisfy at least one of the following (i) and (ii), based on the total amount of the acidic sophorolipid, lactonic sophorolipid, fatty acid, and hydroxy fatty acid in the composition taken as 100 mass %:
(i) lactonic sophorolipid: more than 0 mass % but not more than 2 mass %; and
(ii) fatty acid and hydroxy fatty acid in total: 0.01 to 2.4 mass %.

3. The low-toxicity sophorolipid-containing composition according to claim 1, wherein the proportion of the lactonic sophorolipid is 0.1 to 1.5 mass %, based on the total amount of the acidic sophorolipid, lactonic sophorolipid, fatty acid, and hydroxy fatty acid in the composition taken as 100 mass %.

4. The low-toxicity sophorolipid-containing composition according to claim 1, wherein the low-toxicity sophorolipid-containing composition is provided in an aqueous solution so that the solution has an ethanol-soluble content of 10 mass %, and has an absorbance at a wavelength of 440 nm, hue: OD440of 0.001 to 1.

5. The low-toxicity sophorolipid-containing composition according to claim 1, wherein the composition in an amount corresponding to 1 g of its ethanol-soluble content has a hydroxyl value of 460 to 630 mg KOH/g.

6. The low-toxicity sophorolipid-containing composition according to claim 1, wherein the composition has a HeLa cell lethal concentration ($IC_{50}$) of 2,000 ppm to 60,000 ppm.

7. The low-toxicity sophorolipid-containing composition according to claim 1, wherein the composition has a HeLa cell lethal concentration ($IC_{50}$)/critical micelle concentration (CMC) ratio ($IC_{50}$/CMC) of 6.7 to 200.

8. An anionic surfactant comprising as an active component the low-toxicity sophorolipid-containing composition according to claim 1.

9. A fragrance or cosmetic, a food or beverage, a drug, a quasi-drug, a medical device, a household supply item, or an additive for fragrances or cosmetics, foods or beverages, drugs, quasi-drugs, medical devices, or household supply items, comprising the low-toxicity SL-containing composition according to claim 1.

10. The fragrance or cosmetic, food or beverage, drug, quasi-drug, or additive for fragrances or cosmetics, foods or beverages, drugs, or quasi-drugs, according to claim 9, wherein the fragrance or cosmetic, food or beverage, drug, or quasi-drug is applied to the mucosa, a wound, or a site of inflammation.

11. The low-toxicity sophorolipid-containing composition according to claim 2, wherein the low-toxicity sophorolipid-containing composition is provided in an aqueous solution so that the solution has an ethanol-soluble content of 10 mass %, and has an absorbance at a wavelength of 440 nm, hue:OD440of 0.001 to 1.

12. The low-toxicity sophorolipid-containing composition according to claim 2, wherein the composition in an amount corresponding to 1 g of its ethanol-soluble content has a hydroxyl value of 460 to 630 mg KOH/g.

13. The low-toxicity sophorolipid-containing composition according to claim 2, wherein the composition has a HeLa cell lethal concentration ($IC_{50}$) of 2,000 ppm to 60,000 ppm.

14. The low-toxicity sophorolipid-containing composition according to claim 2, wherein the composition has a HeLa cell lethal concentration ($IC_{50}$)/critical micelle concentration (CMC) ratio ($IC_{50}$/CMC) of 6.7 to 200.

15. A method for reducing the toxicity of a sophorolipid-containing composition, the method comprising subjecting a sophorolipid-containing culture obtained by culturing a sophorolipid-producing yeast, or a treated product thereof, to a step of (1) removing fatty acids and/or hydroxy fatty acids to produce a low-toxicity sophorolipid-containing composition in which the following components are in the following proportions, in terms of dry weight, based on the total amount of acidic sophorolipid, lactonic sophorolipid, fatty acid, and hydroxy fatty acid in the composition taken as 100 mass %:

(a) acidic sophorolipid: not less than 94 mass % and less than 99.99 mass %;
(b) lactonic sophorolipid: more than 0% but not more than 2 mass %; and
(c) fatty acid and hydroxy fatty acid in total: 0.01 to 4 mass %.

16. The method according to claim 15, wherein the method produces a low-toxicity sophorolipid-containing composition in which the proportion of the lactonic sophorolipid and the total proportion of the fatty acid and hydroxy fatty acid satisfy at least one of the following (i) and (ii), based on the total amount of the acidic sophorolipid, lactonic sophorolipid, fatty acid, and hydroxy fatty acid in the composition taken as 100 mass %:

(i) lactonic sophorolipid: more than 0 mass % but not more than 2 mass %; and
(ii) fatty acid and hydroxy fatty acid in total: 0.01 to 2.4 mass %.

17. The method according to claim 15, wherein the method produces a low-toxicity sophorolipid-containing composition in which the proportion of the lactonic sophorolipid is 0.1 to 1.5 mass %, based on the total amount of the acidic sophorolipid, lactonic sophorolipid, fatty acid, and hydroxy fatty acid in the composition taken as 100 mass %.

18. The method according to claim 16, wherein the method produces a low-toxicity sophorolipid-containing composition in which the proportion of the lactonic sophorolipid is 0.1 to 1.5 mass %, based on the total amount of the acidic sophorolipid, lactonic sophorolipid, fatty acid, and hydroxy fatty acid in the composition taken as 100 mass %.

* * * * *